United States Patent
Abraham et al.

(10) Patent No.: US 9,427,456 B2
(45) Date of Patent: Aug. 30, 2016

(54) PEPTIDE THERAPY FOR INCREASING PLATELET LEVELS

(75) Inventors: Michal Abraham, Mevasseret Zion (IL); Amnon Peled, Tel-Aviv (IL); Orly Eizenberg, Rechovot (IL)

(73) Assignee: Biokine Therapeutics Ltd., Nes Ziona (IL)

( * ) Notice: Subject to any disclaimer, the term of this patent is extended or adjusted under 35 U.S.C. 154(b) by 0 days.

(21) Appl. No.: 13/378,061

(22) PCT Filed: Jun. 13, 2010

(86) PCT No.: PCT/IL2010/000466
§ 371 (c)(1),
(2), (4) Date: Dec. 14, 2011

(87) PCT Pub. No.: WO2010/146578
PCT Pub. Date: Dec. 23, 2010

(65) Prior Publication Data
US 2012/0094907 A1  Apr. 19, 2012

Related U.S. Application Data

(60) Provisional application No. 61/186,857, filed on Jun. 14, 2009.

(51) Int. Cl.
*A61K 38/19* (2006.01)
*A61P 7/04* (2006.01)
*A61K 38/10* (2006.01)

(52) U.S. Cl.
CPC ............. *A61K 38/10* (2013.01); *A61K 38/196* (2013.01)

(58) Field of Classification Search
CPC . A61K 2300/00; A61K 38/10; A61K 38/196
See application file for complete search history.

(56) References Cited

U.S. PATENT DOCUMENTS

| | | | |
|---|---|---|---|
| 4,179,337 A | 12/1979 | Davis et al. | |
| 4,342,828 A | 8/1982 | Takaku et al. | |
| 5,206,018 A | 4/1993 | Sehgal et al. | |
| 5,250,732 A | 10/1993 | Kogan et al. | |
| 5,492,126 A | 2/1996 | Hennige et al. | |
| 5,595,756 A | 1/1997 | Bally et al. | |
| 6,128,522 A | 10/2000 | Acker et al. | |
| 6,365,583 B1 | 4/2002 | MacFarland et al. | |
| 6,576,875 B1 | 6/2003 | Kleffner et al. | |
| 6,747,036 B2 | 6/2004 | Gourdeau et al. | |
| 6,875,738 B1 | 4/2005 | Clark-Lewis et al. | |
| 6,946,445 B1 | 9/2005 | Clark-Lewis et al. | |
| 7,138,488 B2 | 11/2006 | Fujii | |
| 7,169,750 B2 | 1/2007 | Bridger et al. | |
| 7,291,631 B2 | 11/2007 | Bridger et al. | |
| 7,419,667 B2 | 9/2008 | Hatake et al. | |
| 7,423,007 B2 | 9/2008 | Fujii et al. | |
| 7,595,298 B2 | 9/2009 | Fujii | |
| 7,630,750 B2 | 12/2009 | Liang et al. | |
| 8,017,585 B2 | 9/2011 | Fujii et al. | |
| 2002/0156034 A1 | 10/2002 | Tudan et al. | |
| 2002/0159996 A1 | 10/2002 | Hariharan et al. | |
| 2004/0116655 A1 | 6/2004 | Fujii | |
| 2004/0197305 A1 | 10/2004 | Garzino-Demo et al. | |
| 2004/0209921 A1 | 10/2004 | Bridger et al. | |
| 2005/0002939 A1 | 1/2005 | Zlotnik et al. | |
| 2005/0043367 A1 | 2/2005 | Bridger et al. | |
| 2005/0265969 A1 | 12/2005 | Clark-Lewis et al. | |
| 2006/0008465 A1 | 1/2006 | Steinaa et al. | |
| 2006/0035829 A1 | 2/2006 | Bridger et al. | |
| 2006/0079492 A1 | 4/2006 | Ahlem et al. | |
| 2006/0264378 A1 | 11/2006 | Fujii et al. | |
| 2006/0264605 A1 | 11/2006 | Fujii | |
| 2007/0119969 A1 | 5/2007 | Collins, Jr. et al. | |
| 2007/0129760 A1 | 6/2007 | Demarais et al. | |
| 2007/0167459 A1 | 7/2007 | Habashita et al. | |
| 2008/0233053 A1 | 9/2008 | Gross et al. | |
| 2009/0181897 A1 | 7/2009 | Fujii et al. | |
| 2010/0143334 A1 | 6/2010 | Peled et al. | |
| 2010/0166715 A1 | 7/2010 | Peled et al. | |
| 2010/0184694 A1 | 7/2010 | Peled et al. | |
| 2010/0222256 A1 | 9/2010 | Fujii | |
| 2011/0269686 A1 | 11/2011 | Fujii et al. | |
| 2012/0082687 A1 | 4/2012 | Yeung et al. | |
| 2012/0207748 A1 | 8/2012 | Peled et al. | |
| 2013/0303460 A1 | 11/2013 | Peled | |
| 2014/0030211 A1 | 1/2014 | Peled et al. | |

(Continued)

FOREIGN PATENT DOCUMENTS

| | | |
|---|---|---|
| CA | 1297007 | 3/1992 |
| EP | 0243153 | 10/1987 |

(Continued)

OTHER PUBLICATIONS

Abraham, M., et al, "Sequential administration of the high affinity CXCR4 antagonist BKT140 promotes megakaryopoiesis and platelet production," British Journal of Haematology, 2013, 163, 248-259.*
Peled A., et al, "The High-Affinity CXCR4 At agonist BKT140 Is Safe and Induces a Robust Mobilization of Human CD34þ Cells in Patients with Multiple Myeloma," Clin Cancer Res; 20(2); 469-79.*
Notification of Office Action and Search Report Dated Mar. 6, 2013 From the State Intellectual Property Office of the People's Republic of China Re. Application No. 201080035931.5 and Its Summary in English.
Translation of Office Action Dated Feb. 1, 2013 From the Japanese Patent Office Re. Application No. 2011-060367.

(Continued)

*Primary Examiner* — Thomas S Heard

(57) ABSTRACT

The present invention is directed to novel therapeutic uses of T-140 analog peptides and compositions comprising same. Specifically, the invention relates to compositions and methods for providing improved platelet levels, useful in the treatment and prevention of thrombocytopenia, for controlling bleeding and for inducing or modulating haemostasis.

6 Claims, 5 Drawing Sheets

(56) References Cited

U.S. PATENT DOCUMENTS

| | | | |
|---|---|---|---|
| 2015/0125549 | A1 | 5/2015 | Peled et al. |
| 2016/0082071 | A1 | 3/2016 | Peled et al. |

FOREIGN PATENT DOCUMENTS

| | | |
|---|---|---|
| EP | 0396158 | 11/1990 |
| EP | 0215126 | 7/1991 |
| EP | 0220520 | 9/1991 |
| EP | 0459516 | 12/1991 |
| EP | 0459795 | 12/1991 |
| EP | 0231819 | 4/1992 |
| EP | 0355811 | 12/1993 |
| EP | 0373679 | 6/1994 |
| EP | 0331186 | 8/1994 |
| EP | 0344796 | 9/1994 |
| EP | 0263490 | 1/1995 |
| EP | 0230980 | 3/1996 |
| EP | 0401384 | 3/1996 |
| EP | 0272703 | 10/1997 |
| EP | 0370205 | 7/1998 |
| EP | 0459630 | 8/1998 |
| EP | 0217404 | 1/1999 |
| EP | 0237545 | 8/1999 |
| EP | 0169566 | 7/2000 |
| EP | 0335423 | 3/2003 |
| EP | 1323730 | 7/2003 |
| EP | 0473268 | 10/2003 |
| EP | 1541585 | 6/2005 |
| EP | 2058395 | 5/2009 |
| JP | 2001-526689 | 12/2001 |
| JP | 2002-506830 | 3/2002 |
| JP | 2002-247843 | 8/2002 |
| JP | 2003-532683 | 11/2003 |
| WO | WO 91/07988 | 6/1991 |
| WO | WO 93/15211 | 8/1993 |
| WO | WO 95/10534 | 4/1995 |
| WO | WO 98/52598 | 11/1998 |
| WO | WO 99/47158 | 9/1999 |
| WO | WO 00/06086 | 2/2000 |
| WO | WO 00/09152 | 2/2000 |
| WO | WO 01/38352 | 5/2001 |
| WO | WO 01/64716 | 9/2001 |
| WO | WO 01/85196 | 11/2001 |
| WO | WO 02/20561 | 3/2002 |
| WO | WO 03/072599 | 9/2003 |
| WO | WO 2004/020462 | 3/2004 |
| WO | WO 2004/024178 | 3/2004 |
| WO | WO 2004/087068 | 10/2004 |
| WO | WO 2007/022523 | 2/2007 |
| WO | WO 2007/067280 | 6/2007 |
| WO | WO 2007/146432 | 12/2007 |
| WO | WO 2008/017025 | 2/2008 |
| WO | WO 2008/075369 | 6/2008 |
| WO | WO 2008/075370 | 6/2008 |
| WO | WO 2008/075371 | 6/2008 |
| WO | WO 2010/146578 | 12/2010 |
| WO | WO 2010/146584 | 12/2010 |
| WO | WO 2012/095849 | 7/2012 |
| WO | WO 2013/160895 | 10/2013 |
| WO | WO 2014/155376 | 10/2014 |
| WO | WO 2015/019284 | 2/2015 |
| WO | WO 2015/063768 | 5/2015 |

OTHER PUBLICATIONS

HIV "Report of the Investigation for Development of HIV Medicaments (Year 2000)", p. 16-21, 2001. Japanese Only!
Translation of Notification of Office Action Dated Mar. 6, 2013 From the State Intellectual Property Office of the People's Republic of China Re. Application No. 201080035931.5.
Translation of Search Report Dated Mar. 6, 2013 From the State Intellectual Property Office of the People's Republic of China Re. Application No. 201080035931.5.
Official Action Dated May 6, 2013 From the US Patent and Trademark Office Re. U.S. Appl. No. 13/360,751.
Office Action Dated May 20, 2013 From the Israel Patent Office Re. Application No. 216912 and Its Translation Into English.
International Preliminary Report on Patentability Dated Jul. 18, 2013 From the International Bureau of WIPO Re. Application No. PCT/IL2012/050008.
Official Action Dated Jul. 5, 2013 From the US Patent and Trademark Office Re. U.S. Appl. No. 12/520,811.
Requisition by the Examiner Dated Jul. 8, 2013 From the Canadian Intellectual Property Office Re. Application No. 2,421,183.
Office Action Dated Jul. 28, 2013 From the Israel Patent Office Re. Application No. 199469 and Its Translation Into English.
International Search Report and the Written Opinion Dated Sep. 2, 2013 From the International Searching Authority Re. Application No. PCT/FI2013/050352.
Requisition by the Examiner Dated Jul. 4, 2013 From the Canadian Intellectual Property Office Re. Application No. 2,537,158.
Burger et al. "CXCR4 Chemokine Receptor Antagonists: Perspectives in SCLC", Expert Opinion on Investigational Drugs, XP002711650, 18(4): 481-490, Apr. 2009.
Burger et al. "Potential of CXCR4 Antagonists for the Treatment of Metastatic Lung Cancer", Expert Reviews of Anticancer Therapy, XP009152669, 1(4): 621-630, Apr. 1, 2011.
Su et al. "Differential Expression of CXCR4 Is Associated With the Metastatic Potential of Human Non-Small Cell Lung Cancer Cells", Clinical Cancer Research, XP055076137, 11(23): 8273-8280, Dec. 1, 2005.
Official Action Dated Sep. 5, 2012 From the US Patent and Trademark Office Re. U.S. Appl. No. 12/520,699.
Official Action Dated Sep. 10, 2012 From the US Patent and Trademark Office Re. U.S. Appl. No. 12/583,746.
Notice of Allowance Dated Sep. 23, 2013 From the US Patent and Trademark Office Re. U.S. Appl. No. 12/520,811.
Official Action Dated Sep. 12, 2012 From the US Patent and Trademark Office Re. U.S. Appl. No. 12/520,803.
Communication Pursuant to Article 94(3) EPC Dated Oct. 4, 2013 From the European Patent Office Re. Application No. 07849623.9.
Abraham et al. "Enhanced Unique Pattern of Hematopoietic Cell Mobilization Induced by the CXCR4 Antagonist 4F-Benzoyl-TN14003", Stem Cells, 25: 2158-2166, 2007.
Communication Pursuant to Article 94(3) EPC Dated Oct. 4, 2013 From the European Patent Office Re. Application No. 07849622.1.
Communication Pursuant to Rules 70(2) and 70a(2) EPC Dated Apr. 28, 2011 From the European Patent Office Re. Application No. 07849622.1.
Supplementary European Search Report and the European Search Opinion Dated Apr. 11, 2011 From the European Patent Office Re. Application No. 07849622.1.
Kucia et al. "Novel Direct Evidence That Adult Bone Marrow-Derived Very Small Embryonic Like (VSEL) Stem Cells Are Mobilized Into Peripheral Blood—Leukopheresis as a Potential Tool to Isolate Pluripotent Stem Cells for Therapeutic Purposes", Database BIOSIS [Online], Biosciences Information Service, XP002630526, Database Accession No. PREV200800216478, Nov. 2007. Abstract.
Liles et al. "Mobilization of Hematopoietic Progenitor Cells in Healthy Volunteers by AMD3100, a CXCR4 Antagonist", Blood, XP003001859, 102(8): 2728-2730, Oct. 15, 2003.
Ratajczak et al. "Stem Cell Plasticity Revisited: CXCR4-Positive Cells Expressing mRNA for Early Muscle, Liver and Neural Cells 'Hide Out' in the Bone Marrow", Leukemia, XP002604057, 18(1): 29-40, Jan. 1, 2004.
Advisory Action Before the Filing of an Appeal Brief Dated Nov. 16, 2012 From the US Patent and Trademark Office Re. U.S. Appl. No. 12/520,699.
Notification of Office Action and Search Report Dated Nov. 5, 2013 From the State Intellectual Property Office of the People's Republic of China Re. Application No. 201080035931.5 and Its Translation into English.
Communication Under Rule 71(3) EPC Dated Oct. 23, 2013 From the European Patent Office Re. Application No. 10789103.8.
Supplementary European Search Report and the European Search Opinion Dated Jan. 3, 2013 From the European Patent Office Re. Application No. 10789103.8.

(56) References Cited

OTHER PUBLICATIONS

Notice of Allowance Dated Feb. 8, 2013 From the US Patent and Trademark Office Re. U.S. Appl. No. 12/520,699.
Office Action Dated Mar. 13, 2013 From the Israel Patent Office Re. Application No. 199468 and Its Translation Into English.
Official Action Dated Apr. 24, 2013 From the US Patent and Trademark Office Re. U.S. Appl. No. 13/360,751.
HIV "Strategic Generation of Anti-AIDS Agents Based on HIV Secondary Receptor Antagonists and Modification of the Agents for Pharmaceutical Use", Report of the Investigation for Development of HIV Medicaments (Year 2000), p. 16-21, 2001. English Translation.
Tamamura et al. "Development of Selective Antagonists Against an HIV Second Receptor", Yakugaku Zasshi, 121(11): 781-792, 2001. English Translation.
Communication Pursuant to Article 94(3) EPC Dated May 3, 2013 From the European Patent Office Re. Application No. 10176632.7.
Requisition—Sequence Listing Dated May 9, 2013 From the Canadian Intellectual Property Office Re. Application No. 2,673,719.
Requisition by the Examiner Dated Jun. 18, 2013 From the Canadian Intellectual Property Office Re. Application No. 2,673,484.
Amendment Dated May 15, 2008 After Notice of Allowance of Apr. 14, 2008 From the US Patent and Trademark Office Re. U.S. Appl. No. 10/525,838.
Communication Pursuant to Article 94(3) EPC Dated Oct. 4, 2010 From the European Patent Office Re. Application No. 03791288.8.
Communication Pursuant to Article 94(3) EPC Dated Apr. 9, 2008 From the European Patent Office Re. Application No. 03791288.8.
Communication Pursuant to Article 94(3) EPC Dated Dec. 15, 2008 From the European Patent Office Re. Application No. 03791288.8.
Communication Pursuant to Article 94(3) EPC Dated Sep. 15, 2009 From the European Patent Office Re. Application No. 03791288.8.
Communication Pursuant to Article 96(2) EPC Dated Feb. 6, 2006 From the European Patent Office Re. Application No. 10963414.6.
Communication Pursuant to Article 96(2) EPC Dated Mar. 17, 2005 From the European Patent Office Re. Application No. 10963414.6.
Communication Pursuant to Article 96(2) EPC Dated Jul. 18, 2006 From the European Patent Office Re. Application No. 10963414.6.
Communication Pursuant to Article 96(2) EPC Dated Jul. 26, 2007 From the European Patent Office Re. Application No. 10963414.6.
Communication Pursuant to Rule 69 EPC—Reminder Concerning Payment of the Designation Fee (Art. 79(2) EPC) and of the Examination Fee (Art. 94(1) EPC)—and Invitation Pursuant to Rule 70a(1) EPC Dated Mar. 12, 2012 From the European Patent Office Re. Application No. 10176632.7.
Communication Under Rule 71(3) EPC Dated Apr. 16, 2012 From the European Patent Office Re. Application No. 03791288.8.
European Search Report and the European Search Opinion Dated Feb. 3, 2012 From the European Patent Office Re. Application No. 10176632.7.
International Preliminary Report on Patentability Dated Apr. 19, 2002 From the International Preliminary Examining Authority Re. PCT/JP2001/007668.
International Preliminary Report on Patentability Dated Aug. 19, 2004 From the International Preliminary Examining Authority Re. Application No. PCT/JP2003/010753.
International Preliminary Report on Patentability Dated Jun. 24, 2009 From the International Bureau of WIPO Re. Application No. PCT/IL2007/001596.
International Preliminary Report on Patentability Dated Jun. 24, 2009 From the International Bureau of WIPO Re. Application No. PCT/IL2007/001598.
International Search Report and the Written Opinion Dated Jun. 4, 2008 From the International Searching Authority Re. Application No. PCT/IL2007/001598.
International Search Report and the Written Opinion Dated Dec. 5, 2008 From the International Searching Authority Re. Application No. PCT/IL2007/001596.
International Search Report and the Written Opinion Dated Jun. 24, 2009 From the International Searching Authority Re. Application No. PCT/IL2007/001597.
International Search Report and the Written Opinion Dated May 30, 2012 From the International Searching Authority Re. Application No. PCT/IL2012/050008.
International Search Report Dated Nov. 4, 2003 From the International Searching Authority Re. Application No. PCT/JP2003/010753.
International Search Report Dated Dec. 11, 2001 From the International Searching Authority Re. Application No. PCT/JP2001/007668.
Interview Summary Dated May 3, 2005 From the US Patent and Trademark Office Re. U.S. Appl. No. 10/363,209.
Interview Summary Dated Feb. 21, 2006 From the US Patent and Trademark Office Re. U.S. Appl. No. 10/363,209.
Notice of Allowance Dated Mar. 9, 2006 From the US Patent and Trademark Office Re. U.S. Appl. No. 10/363,209.
Notice of Allowance Dated Apr. 11, 2011 From the US Patent and Trademark Office Re. U.S. Appl. No. 12/172,007.
Notice of Allowance Dated Apr. 14, 2008 From the US Patent and Trademark Office Re. U.S. Appl. No. 10/525,838.
Notice of Allowance DAted May 21, 2009 From the US Patent and Trademark Office Re. U.S. Appl. No. 11/497,225.
Office Action Dated May 4, 2010 From the Israel Patent Office Re. Application No. 199468.
Office Action Dated May 4, 2010 From the Israel Patent Office Re. Application No. 199469.
Office Action Dated Sep. 4, 2011 From the Israel Patent Office Re. Application No. 199468 and Its Translation Into English.
Office Action Dated Oct. 31, 2011 From the Israel Patent Office Re. Application No. 199469 and Its Translation Into English.
Official Action Dated Jul. 1, 2010 From the US Patent and Trademark Office Re. U.S. Appl. No. 12/172,007.
Official Action Dated Nov. 3, 2005 From the US Patent and Trademark Office Re. U.S. Appl. No. 10/363,209.
Official Action Dated May 4, 2012 From the US Patent and Trademark Office Re. U.S. Appl. No. 12/520,699.
Official Action Dated Mar. 5, 2012 From the US Patent and Trademark Office Re. U.S. Appl. No. 12/520,803.
Official Action Dated Jul. 11, 2007 From the US Patent and Trademark Office Re. U.S. Appl. No. 10/525,838.
Official Action Dated Jun. 15, 2005 From the US Patent and Trademark Office Re. U.S. Appl. No. 10/363,209.
Official Action Dated May 18, 2012 From the US Patent and Trademark Office Re. U.S. Appl. No. 13/178,737.
Official Action Dated Jan. 24, 2011 From the US Patent and Trademark Office Re. U.S. Appl. No. 12/172,007.
Official Action Dated Jun. 25, 2012 From the US Patent and Trademark Office Re. U.S. Appl. No. 12/520,811.
Official Action Dated Aug. 28, 2008 From the US Patent and Trademark Office Re. U.S. Appl. No. 11/497,225.
Official Action Dated Dec. 28, 2011 From the US Patent and Trademark Office Re. U.S. Appl. No. 12/583,746.
Requisition—Sequence Listing Dated Jan. 5, 2011 From the Canadian Intellectual Property Office Re. Application No. 2,673,719.
Requisition by the Examiner Dated Jul. 6, 2012 From the Canadian Intellectual Property Office Re. Application No. 2,421,183.
Requisition by the Examiner Dated Mar. 8, 2011 From the Canadian Intellectual Property Office Re. Application No. 2,421,183.
Requisition by the Examiner Dated Oct. 17, 2011 From the Canadian Intellectual Property Office Re. Application No. 2,537,158.
Requisition by the Examiner Dated May 19, 2011 From the Canadian Intellectual Property Office Re. Application No. 2,421,183.
Requisition by the Examiner Dated Aug. 25, 2009 From the Canadian Intellectual Property Office Re. Application No. 2,421,183.
Requisition by the Examiner Dated May 25, 2010 From the Canadian Intellectual Property Office Re. Application No. 2,537,158.
Responc Dated Jan. 4, 2012 to Office Action of Sep. 4, 2011 From the Israel Patent Office Re. Application No. 199468 and Its Translation Into English.

(56) References Cited

OTHER PUBLICATIONS

Response Dated Jul. 1, 2005 to Communication Pursuant to Article 96(2) EPC of Mar. 17, 2005 From the European Patent Office Re. Application No. 10963414.6.
Response Dated Nov. 1, 2010 to Official Action of Jul. 1, 2010 From the US Patent and Trademark Office Re. U.S. Appl. No. 12/172,007.
Response Dated Feb. 3, 2006 to Official Action of Nov. 3, 2005 From the US Patent and Trademark Office Re. U.S. Appl. No. 10/363,209.
Response Dated Jun. 4, 2008 to Restriction Official Action of Apr. 8, 2008 From the US Patent and Trademark Office Re. U.S. Appl. No. 11/497,225.
Response Dated Sep. 7, 2011 to Requisition by the Examiner of Mar. 8, 2011 From the Canadian Intellectual Property Office Re. Application No. 2,421,183.
Response Dated Dec. 8, 2009 to Office Action of Aug. 11, 2009 From the Japanese Patent Office Re. Application No. 2003-301176.
Response Dated Jan. 8, 2008 to Official Action of Jul. 11, 2007 From the US Patent and Trademark Office Re. U.S. Appl. No. 10/525,838.
Response Dated May 9, 2006 to Communication Pursuant to Article 96(2) EPC of Feb. 6, 2006 From the European Patent Office Re. Application No. 10963414.6.
Response Dated Jun. 10, 2009 to Restriction Official Action of Mar. 26, 2009 From the US Patent and Trademark Office Re. U.S. Appl. No. 12/172,007.
Response Dated Oct. 12, 2010 to Communication Pursuant to Article 94(3) EPC of Oct. 4, 2010 From the European Patent Office Re. Application No. 03791288.8.
Response Dated Oct. 14, 2011 to Restriction Official Action of Sep. 14, 2011 From the US Patent and Trademark Office Re. U.S. Appl. No. 12/583,746.
Response Dated Apr. 15, 2009 to Communication Pursuant to Article 94(3) EPC of Dec. 15, 2008 From the European Patent Office Re. Application No. 03791288.8.
Response Dated Oct. 15, 2008 to Communication Pursuant to Article 94(3) EPC of Apr. 9, 2008 From the European Patent Office Re. Application No. 03791288.8.
Response Dated Sep. 15, 2005 to Official Action of Jun. 15, 2005 From the US Patent and Trademark Office Re. U.S. Appl. No. 10/363,209.
Response Dated Nov. 16, 2007 to Communication Pursuant to Article 96(2) EPC of Jul. 26, 2007 From the European Patent Office Re. Application No. 10963414.6.
Response Dated Apr. 18, 2005 to Restriction Official Action of Mar. 18, 2005 From the US Patent and Trademark Office Re. U.S. Appl. No. 10/363,209.
Response Dated Jan. 21, 2010 to Communication Pursuant to Article 94(3) EPC of Sep. 15, 2009 From the European Patent Office Re. Application No. 03791288.8.
Response Dated Oct. 21, 2010 to Office Action of May 4, 2010 From the Israel Patent Office Re. Application No. 199468.
Response Dated Oct. 21, 2010 to Office Action of May 4, 2010 From the Israel Patent Office Re. Application No. 199469.
Response Dated Mar. 22, 2011 to Requisition—Sequence Listing of Jan. 5, 2011 From the Canadian Intellectual Property Office Re. Application No. 2,673,719.
Response Dated Mar. 23, 2011 to Official Action of Jan. 24, 2011 From the US Patent and Trademark Office Re. U.S. Appl. No. 12/172,007.
Response Dated Feb. 24, 2010 to Requisition by the Examiner of Aug. 25, 2009 From the Canadian Intellectual Property Office Re. Application No. 2,421,183.
Response Dated May 25, 2007 to Restriction Official Action of Feb. 6, 2007 From the US Patent and Trademark Office Re. U.S. Appl. No. 10/525,838.
Response Dated Nov. 25, 2011 to Requisition by the Examiner of May 25, 2010 From the Canadian Intellectual Property Office Re. Application No. 2,537,158.
Response Dated Jan. 26, 2009 to Official Action of Aug. 28, 2008 From the US Patent and Trademark Office Re. U.S. Appl. No. 11/497,225.
Response Dated Jan. 29, 2007 to Communication Pursuant to Article 96(2) EPC of Jul. 18, 2006 From the European Patent Office Re. Application No. 10963414.6.
Response Dated Jun. 30, 2010 to Requisition by the Examiner of May 19, 2011 From the Canadian Intellectual Property Office Re. Application No. 2,421,183.
Response Dated Jan. 31, 2011 to Office Action of Oct. 19, 2010 From the Japanese Patent Office Re. Application No. 2003-301176.
Restriction Official Action Dated Mar. 1, 2012 From the US Patent and Trademark Office Re. U.S. Appl. No. 12/520,699.
Restriction Official Action Dated Feb. 6, 2007 From the US Patent and Trademark Office Re. U.S. Appl. No. 10/525,838.
Restriction Official Action Dated Apr. 8, 2008 From the US Patent and Trademark Office Re. U.S. Appl. No. 11/497,225.
Restriction Official Action Dated Sep. 14, 2011 From the US Patent and Trademark Office Re. U.S. Appl. No. 12/583,746.
Restriction Official Action Dated Feb. 16, 2012 From the US Patent and Trademark Office Re. U.S. Appl. No. 13/178,737.
Restriction Official Action Dated Mar. 18, 2005 From the US Patent and Trademark Office Re. U.S. Appl. No. 10/363,209.
Restriction Official Action Dated Mar. 26, 2009 From the US Patent and Trademark Office Re. U.S. Appl. No. 12/172,007.
Restriction Official Action Dated Dec. 28, 2011 From the US Patent and Trademark Office Re. U.S. Appl. No. 12/520,803.
Restriction Official Action Dated Mar. 28, 2012 From the US Patent and Trademark Office Re. U.S. Appl. No. 12/520,811.
Second Amendment Dated Jul. 14, 2008 to Amendment of May 15, 2008 After Notice of Allowance of Apr. 14, 2008 From the US Patent and Trademark Office Re. U.S. Appl. No. 10/525,838.
Supplementary European Search Report Dated Nov. 19, 2004 From the European Patent Office Re. Application No. 01963414.6.
Supplementary Partial European Search Report Dated Nov. 28, 2007 From the European Patent Office Re. Application No. 03791288.8.
Translation of Office Action Dated Aug. 11, 2009 From the Japanese Patent Office Re. Application No. 2003-301176.
Translation of Office Action Dated Oct. 19, 2010 From the Japanese Patent Office Re. Application No. 2003-301176.
AACR "97th Annual Meeting 2006: Publications", AACR, American Association of Cancer Research, Retreived From the Internet, 2006.
Arakaki et al. "T134, A Small-Molecule CXCR4 Inhibitor, Has No Cross-Drug Resistance With AMD3100, A CXCR4 Antagonist With a Different Structure", Journal of Virology, XP002199036, 73(2): 1719-1723, Feb. 1999.
Auerbach et al. "Angiogenesis Assays: Problems, Pitfalls and Potential", Cancer and Metastasis Reviews, 19: 167-172, 2000.
Avniel et al. "Involvement of the CXCL12/CXCR4 Pathway in the Recovery of Skin Following Burns", Journal of Investigative Dermatology, 126(2): 468-476, 2006.
Balkwill "The Significance of Cancer Cell Expression of the Chemokine Receptor CXCR4", Seminars in Cancer Biology, 14: 171-179, 2004.
Bork "Powers and Pitfalls in Sequence Analysis: The 70% Hurdle", Genome Research, 10: 398-400, 2000.
Brenner "Errors in Genome Annotation", Trends in Genetics, TIG, 15(4): 132-133, Apr. 1999.
Broxmeyer et al. "Rapid Mobilization of Murine and Human Hematopoietic Stem and Progenitor Cells With AMD3100, a CXCR4 Antagonist", The Journal of Experimental Medicine, 201(8): 1307-1318, Apr. 18, 2005.
Burger et al. "Small Peptide Inhibitors of the CXCR4 Chemokine Receptor (CD184) Antagonize the Activation, Migration, and Antiapoptotic Responses of CXCL12 in Chronic Lymphocytic Leukemia B Cells", Blood, 106(5): 1824-1830, Sep. 1, 2005.
Dar et al. "Chemokine Receptor CXCR4-Dependent Internalization and Re secretion of Functional Chemokine SDF-1 by Bone Marrow Endothelial and Stromal Cells", Nature Immunology, 6(10): 1038-1046, Oct. 2005.

(56) References Cited

OTHER PUBLICATIONS

Darash-Yahana et al. "Role of High Expression Levels of CXCR4 in Tumor Growth, Vascularization, and Metastatis", The FASEB Journal, 18: 1240-1242, 2004. p. 1242, Last Para.
Di Cesare et al. "In Vitro Characterization and Inhibition of the CXCR4/CXCL12 Chemokine Axis in Human Uveal Melanoma Cell Lines", Cancer Cell International, XP021036445, 7(17): 1-8, Nov. 14, 2007. Abstract, Last Para, Title, p. 5, Right Col., Last Para.
Doerks et al. "Protein Annotation: Detective Work for Function Predicition", Trends in Genetics, 14(6): 248-250, Jun. 1998.
Esler et al. "Renal Sympathetic Denervation in Patients With Treatment-Resistant Hypertension (The Symplicity HTN-2 Trial): A Randomised Controlled Trial", The Lancet, 376: 1903-1909, Published Online Nov. 17, 2010.
Flomenberg et al. "The Use of AMD3100 Plus G-CSF for Autologous Hematopoietic Progenitor Cell Mobilization Is Superior to G-CSF Alone", Blood, 106(5): 1867-1874, 2005.
Fransen et al. "Suppression of Dualtropic Human Immunodeficiency Virus Type 1 by the CXCR4 Antagonist AMD3100 Is Associated With Efficiency of CXCR4 Use and Baseline Virus Composition", Antimicrobial Agents and Chemotherapy, 52(7): 2608-2615, Apr. 28, 2008.
Fujii.
Fujii et al. "Peptide-Lead CXCR4 Antagonists With High Anti-HIV Activity", Current Opinion in Investigational Drugs, 2(9): 1198-1202, 2001.
Ghobrial et al. "Molecular Mechanisms Involved in Homing and Migration of Plasma Cells in Response to CXCR4", Blood, XP002629051, 104(11): 1-33, Apr. 12, 2005.
Gotoh et al. "Increase of R5 HIV-1 Infection and CCR5 Expression in T Cells Treated With High Concentrations of CXCR4 Antagonists and SDF-1", Journal of Infection and Chemotherapy, 7(1): 28-36, 2001.
Gura "Cancer Models: Systems for Identifying New Drugs Are Often Faulty", Science, 278(5340): 1041-1042, Nov. 7, 1997.
Hatse et al. "CXC-ChemokineReceptor 4 as a Potential New Therapeutic Target for Neuroblastoma and Breast Cancer", International Journal of Cancer, XP001156644, Supplement, 13: 349, Abstract # P 669, Jul. 2002.
Hendrix et al. "Safety, Pharmacokinetics, and Antiviral Activity of AMD3100, A Selective CXCR4 Receptor Inhibitor, in HIV-1 Infection", Journal of Aquired Immune Deficiency Syndromes, JAIDS, 37(2): 1253-1261, Oct. 1, 2004.
Heredia et al. "Rapamycin Causes Down-Regulation of CCR5 and Accumulation of Anti-HIV Beta-Chemokines: An Approach to Suppress R5 Strains of HIV-1", Proc. Natl. Acad. Sci. USA, PNAS, 100(18): 10411-10416, Sep. 2, 2003.
Hesselgesser et al. "Neuronal Apoptosis Induced by HIV-1 Gp120 and the Chemokine SDF-1Alpha Is Mediated by the Chemokine Receptor CXCR4", Current Biology, 8: 595-598, Apr. 27, 1998.
Hiramatsu et al. "Synthesis of CXCR4 Antagonists, T140 Derivatives With Improved Biostability, and Their SAR Study", Peptide Science, XP009092185, 203: 213-216, 2002. Abstract, Fig.1.
Jain "Barriers to Drug Delivery in Solid Tumors. Many Tumors Resist Full Penetration by Anticancer Agents. Such Resistance May Help Explain Why Drugs That Eradicate Tumor Cells in Laboratory Dishes Often Fail to Eliminate Malignancies in the Body", Scientific American, p. 58-65, Jul. 1994.
Kim et al. "In Vitro Behavior of Hematopoietic Progenitor Cells Under the Influence of Chemoattractants: Stromal Cell-DErived Factor-1, Steel Factor, and the Bone Marrow Environment", Blood, 91(1): 100-110, 1998.
Kollet et al. "Human CD34+CXCR4-Sorted Cells Harbor Intracellular CXCR4, Which Can Be Functionally Expressed and Provide NOD/SCID Repopulation", Blood, 100(8): 2778-2786, 2002.
Koshiba et al. "Expression of Stromal Cell-Derived Factor 1 and CXCR4 Ligand Receptor System in Pancreatic Cancer: A Possible Role for Tumor Progression", Clinical Cancer Research, 6(9): 3530-3535, Sep. 2000.
Lack et al. "A Pharmacokinetic-Pharmacodynamic Model for the Mobilization of CD34+ Hematopoietic Progenitor Cells by AMD3100", Clinical Pharmacology and Therapeutics, 77(5): 427-436, 2005.
Lapidot et al. "How Do Stem Cells Find Their Way Home?", Blood, 106(6): 1901-1910, 2005.
Lapidot et al. "The Essential Roles of the Chemokine SDF-1 and Its Receptor CXCR4 in Human Stem Cell Homing and Repopulation of Transplanted Immune-Deficient NOD/SCID and NOD/SCID/B2m<Null> Mice", Leukemia, 16(10): 1992-2003, 2002.
Levesque et al. "Disruption of the CXCR4/CXCL12 Chemotactic Interaction During Hematopoietic Stem Cell Mobilization Induced by GCSF or Cyclophosphamide", Journal of Clinical Investigation, 111(2): 187-196, Jan. 2003.
Martin et al. "Chemokines Acting Via CXCR2 and CXCR4 Control the Release of Neutrophils From the Bone Marrow and Their Return Following Senescence", Immunity, 19(4): 583-593, Oct. 2003.
Matthys et al. "AMD3100, A Potent and Specific Antagonist of the Stromal Cell-Derived Factor-1 Chemokine Receptor CXCR4, Inhibits Autoimmune Joint Inflammation in IFN-Gamma Receptor-Deficient Mice", The Journal of Immunology, 167(8): 4686-4692, 2001.
Menu et al. "The Involvement of Stromal Derived Factor 1Alpha in Homing and Progression of Multiple Myeloma in the 5TMM Model", Haematologica/The Hematology Journal, 91(5): 605-612, 2006.
Merck "Clinical Aspects of Cancer", The Merck Manual, Jun. 26, 2007.
Merck "Introduction: Overview of Cancer", The Merck Manual, Jun. 26, 2007.
Merck "Rheumatoid Arthritis (RA)", The Merck Manual, 18th Ed., 2005.
Mori et al. "Involvement of Stromal Cell-Derived Factor 1 and CXCR4 Receptor System in Pancreatic Cancer", Gastroenterology, XP009021758, 122(4/Suppl.1): A490, Abstract # T1608, Apr. 2002.
Mueller et al. "Involvement of Chemokine Receptors in Breast. Cancer Metastasis", Nature, 410: 50-56, Mar. 2001.
Nagasawa et al. "Molecular Cloning and Structure of a Pre-B-Cell Growth-Stimulating Factor", Proc. Natl. Acad. sci. USA, 91: 2305-2309, Mar. 1994.
Nakashima et al. "Anti-Human Immunodeficiency Virus Activity of A Novel Synthetic Peptide, T22 ([Tyr-5,12, Lys-7]Polyphemusin II): A Possible Inhibitor of Virus-Cell Fusion", Antimicrobial Agents and Chemotherapy, 36(6): 1249-1255, Jun. 1992.
Neidl "Failure Modes in the Discovery Process", Cancer Drug Design and Discovery, Chap.18.2.2: 427-431, 2008.
Ngo et al. "Computational Complexity, Protein Structure Prediction, and the Levinthal Paradox", The Protein Folding Problem and Tertiary Structure Prediction, Chap.14: 433-440, 492-495, 1994.
Omagari et al. "Development of Specific CXCR4 Inhibitors Based on an Anti-HIV Peptide, T140, and Their Structure-Activity Relationships Study", Peptide Science, 2000(37): 129-132, 2001.
Peled et al. "Dependence of Human Stem Cell Engraftment and Repopulation of NOD/SCID Mice on CXCR4", Science, 283(5403): 845-848, 1999.
Phillips et al. "Epidermal Growth Factor and Hypoxia-Induced Expression of CXC Chemokine Receptor 4 on Non-Small Cell Lung Cancer Cells Is Regulated by the Phosphatidylinositol 3-Kinasc/PTEN/AKT/Mammalian Target of Rapamycin Signaling Pathway and Activation of Hypoxia Inducible Factor-1Alpha", The Journal of Biological Chemistry, 280(23): 22473-22481, 2005.
Phillips et al. "The Stromal Derived Factor-1/CXCL12-CXC Chemokine Receptor 4 Biological Axis in Non-Small Cell Lung Cancer Metastasis", 167: 1676-1686, 2003.
Princen et al. "HIV Chemokine Receptor Inhibitors as Novel Anti-HIV Drugs", Cytokine & Growth Factor Reviews, 16(6): 659-677, 2005.
Ratajczak et al. "T140 Enhances G-CSF-Induced Mobilization of Hematopoietic Stem Cells", Experimental Hematology, 31: 154, Abstract #280, 2003.
Rossi et al. "The Biology of Chemokines and Their Receptors", Annual Reviews of Immunology, 18: 217-242, 2000.

(56) References Cited

OTHER PUBLICATIONS

Skolnick et al. "From Genes to Protein Structure and Function: Novel Applications of Computational Approaches in the Genomic Era", Trends in Biotechnology, TIBTECH, 18(1): 34-39, Jan. 2000.
Sporn et al. "Chemoprevention of Cancer", Carcinogenesis, 21(3): 525-530, 2000.
Tamamura "Development of Selective Antagonists Against An HIV Second Receptor", Yakugaku Zasshi, 121(11): 781-792, 2001. Abstract in English.
Tamamura et al. "A Future Perspective on the Development of Chemokine Receptor CXCR4 Antagonists", Database EMBASE [Online], XP002675634, Database Accession No. EMB-2008509452, Oct. 2008. & Expert Opinion on Drug Discovery, 3(10): 1155-1166, Oct. 2008.
Tamamura et al. "A Low-Molecular-Weight Inhibitor Against the Chemokine Receptor CXCR4: A Strong Anti-HIV Paptide T140", Biochemical and Biophysical Research Communications, 253(3): 877-882, 1998.
Tamamura et al. "A Low-Molecular-Weight Inhibitor Against the Chemokine Receptor CXCR4: A Strong Anti-HIV Peptide T140", Biochemic and Biophysical Research Communications, XP002169961, 253(3): 877-882, Jan. 1, 1998. Abstract, Fig.1.
Tamamura et al. "A Low-Molecular-Weight Inhibitor Against the Chemokine Receptor CXCR4: A Strong Anti-HIV Peptide T140", Biochemical and Biophysical Research Communications, 253(3): 877-882, 1998.
Tamamura et al. "Certification of the Critical Importance of L-3-(2-Naphtyl)Alanine at Position 3 of A Specific CXCR4 Inhibitor, T140, Leads to An Exploratory Performance of Its Downsizing Study", Bioorganic & Medicinal Chemistry, 10: 1417-1426, 2002.
Tamamura et al. "Development of Specific CXCR4 Inhibitors Possessing High Selectivity Indexes as Well as Complete Stability in Serum Based on an Anti-HIV Peptide T140", Bioorganic & Medicinal Chemistry Letters, XP002265743, 11(14): 1897-1902, Jul. 23, 2001. Abstract, Fig.1, p. 1901, r-h Col., Last Sentence Before 'Acknowledgements'.
Tamamura et al. "Downsizing of An HIV-Cell Fusion Inhibitor, T22 ([Tyr5,12, Lys7]-Polyphemusin II), With the Maintenance of Anti-HIV Activity and Solution Structure", Bioorganic & Medicinal Chemistry, 6: 473-479, 1998.
Tamamura et al. "Downsizing of an HIV-Cell Fusion Inhibitor, T22 ([Tyr5,12, Lys7]-Polyphemusin II), With the Maintenance of Anti-HIV Activity and Solution Structure", Bioorganic & Medicinal Chemistry, XP002458598, 6(4): 473-479, Apr. 1998. Abstract, Fig.1.
Tamamura et al. "Effective Lowly Cytotoxic Analogs of An HIV-Cell Fusion Inhibitor, T22 ([Tyr5,12, Lys7]-Polyphemusin II)", Bioorganic & Medicinal Chemistry, 6(2): 231-238, 1998.
Tamamura et al. "Effective Lowly Cytotoxic Analogs of An HIV-Cell Fusion Inhibitor, T22 ([Tyr5,12, Lys7]-Polyphemusin II)", Bioorganic & Medicinal Chemistry, XP002906341, 6(2): 231-238, Jan. 1, 1998. Abstract, Fig.1.
Tamamura et al. "Efficient Analogs of An Anti-HIV Peptide, T22 ([Tyr5,12, Lys7]-Polyphemusin II), Having Low Cytotoxicity", Peptide Science—Present and Future, Proceedings of the 1st International Peptide Symposium, XP002973954, 1997: 427-429, Jan. 1, 1999. Abstract, Fig.2.
Tamamura et al. "Enhancement of the T140-Based Pharmacophores Leads to the Development of More Potent and Bio-Stable CXCR4 Antagonists", Organic Biomolecular Chemistry, 1: 3663-3669, 2003.
Tamamura et al. "HIV-Cell Fusion Inhibitors Targeted to the HIV Second Receptor: T22 and Its Downsized Analogs With High Activity", Peptide Science, 1998(35): 49-52, 1999.
Tamamura et al. "Pharmacophore Identification of A Specific CXCR4 Inhibitor, T140, Leads to Development of Effective Anti-HIV Agents With Very High Selectivity Indexes", Bioorganic & Medicinal Chemistry Letters, 10(23): 2633-2637, 2000.
Tamamura ct al. "Pharmacphorc Identification of A Specific CXCR4 Inhibitor, T140, Leads to Development of Effective Anti-HIV Agents With Very High Selectivity Indexes", Bioorganic & Medicinal Chemistry Letters, 10(23): 2633-2637, 2000.
Tamamura et al. "T140 Analogs as CXCR4 Antagonists Identified as Anti-Metastatic Agents in the Treatment of Breast Cancer", FEBS Letters, 550: 79-83, 2003.
Tamamura et al. "T140 Analogs as CXCR4 Antagonists Identified as Anti-Metastatic Agents in the Treatment of Breast Cancer", FEBS Letters, XP004448372, 550: 79-83, Aug. 28, 2003.
Tamamura et al. "The Therapeutic Potential of CXCR4 Antagonists in the Treatment of HIV Infection, Cancer Metastasis and Rheumatoid Arthritis", Expert Opinion of Therapeutic Targets, 9(6): 1267-1282, 2005.
Tsutsumi et al. "Therapeutic Potential of the Chemokine Receptor CXCR4 Antagonists as Multifunctional Agents", Biopolymers (Peptide Science), XP002629052, 88(2): 279-289, 2006.
Ulvatne et al. "Short Antibacterial Peptides and Erythromycin Act Synergically Against *Escherichia coli*", Journal of Antimicrobial Chemotherapy, 48: 203-208, 2001.
Weekes et al. "Stromal Derived FactorlAlpha Mediates Resistance to mTOR Inhibition by the Preservation of Hypoxia Inducible Factor-1Alpha (HIF-1Alpha) Expression", Proceedings of the Annual Meeting of the American Association for Cancer Research, AACR, 47: 553, Abstract #2341, 2006.
Wells "Additivity of Mutational Effects in Proteins", Biochemistry, 29(37): 8509-8517, Sep. 18, 1990.
Zannettino et al. "Elevated Serum Levels of Stromal-Derived Factor-1Alpha Are Associated With Increased Osteoclast Activity and Osteolytic Bone Disease in Multiple Myeloma Patients", Cancer Research, 65(5): 1700-1709, Mar. 1, 2005. Abstract, p. 1707, Last Para—p. 1708, First Para.
Zhou et al. "CXCR4 Is a Major Chemokine Receptor on Glioma Cells and Mediates Their Survival", The Journal of Biological Chemistry, 277(51): 49481-49487, Dec. 29, 2002.
Zuluaga et al. "Neutropenia Induced in Outbred Mice by A Simplified Low-Dose Cyclophosphamide Regimen: Characterization and Applicability to Diverse Experimental Models of Infectious Diseases", BMC Infectious Diseases, 6(55): 1-10, Mar. 17, 2006.
Communication Pursuant to Article 94(3) EPC Dated Sep. 11, 2013 From the European Patent Office Re. Application No. 10176632.7.
Completion Requirement Letter Dated Oct. 24, 2013 From the Canadian Intellectual Property Office Re. Application No. 2,765,345.
Official Action Dated Dec. 7, 2012 From the US Patent and Trademark Office Re. U.S. Appl. No. 12/520,699.
Notice of Allowance Dated Dec. 10, 2012 From the US Patent and Trademark Office Re. U.S. Appl. No. 13/178,737.
Kucia et al. "Trafficking of Normal Stem Cells and Metastasis of Cancer Stem Cells Involve Similar Mechanisms: Pivotal Role of the SDF-1—CXCR4 Axis", Stem Cells, 23(7): 879-894, Aug. 2005.
Voermans et al. "Migratory Behavior of Leukemic Cells From Acute Myeloid Leukemia Patients", Leukemia, 16(4): 650-657, Apr. 2002.
International Search Report and the Written Opinion Dated Oct. 15, 2010 From the International Searching Authority Re. Application No. PCT/IL2010/000466.
Communication Pursuant to Rules 70(2) and 70a(2) EPC Dated Jan. 22, 2013 From the European Patent Office Re. Application No. 10789103.8.
Official Action Dated Jan. 29, 2013 From the US Patent and Trademark Office Re. U.S. Appl. No. 13/360,751.
Official Action Dated Jan. 31, 2013 From the US Patent and Trademark Office Re. U.S. Appl. No. 12/520,811.
Notice of Allowance Dated Jan. 4, 2013 From the US Patent and Trademark Office Re. U.S. Appl. No. 12/583,746.
International Preliminary Report on Patentability Dated Dec. 29, 2011 From the International Bureau of WIPO Re. Application No. PCT/IL2010/000466.
Restriction Official Action Dated Feb. 4, 2014 From the US Patent and Trademark Office Re. U.S. Appl. No. 13/978,740.
Notice of Allowance Dated Jan. 7, 2014 From the US Patent and Trademark Office Re. U.S. Appl. No. 13/360,751.
Office Action Dated Jul. 30, 2014 From the Israel Patent Office Re. Application No. 216912 and Its Translation Into English.

(56) References Cited

OTHER PUBLICATIONS

Partial European Search Report Dated Jun. 4, 2014 From the European Patent Office Re. Application No. 14153703.5.
Coiffier et al. "Chop Chemotherapy Plus Rituximab Compared With Chop Alone in Elderly Patients With Diffuse Large-B-Cell Lymphoma", The New England Journal of Medicine, XP055117777, 346(4): 235-242, Jan. 24, 2002.
Kaufman et al. "The Effect of Rituximab on Mobilization With AMD3100 Plus G-CSF in Patients With Relapsed or Refractory NHL or HD", Blood, ASH Annual Meeting Abstracts, 110(11/Pt.1): 568A, # 1912, 49th Annual Meeting of the American-Society-of-Hematology, Atlanta, GA, USA, Dec. 8-10, 2007.
Kaufman et al. "The Effect of Rituximab on Mobilization With AMD3100 Plus G-CSF in Patients With Relapsed or Refractory NHL or HD", Database BIOSIS [Online], XP002724332, Databse Accession No. PREV200800217184, 4 P., Nov. 16, 2007. Abstract.
Sehn et al. "Treatment of Aggressive Non-Hodgkin's Lymphoma: A North American Perspective", Oncology, XP009177924, 19(4/Suppl.1): 26-34, Apr. 2005.
European Search Report and the European Search Opinion Dated Oct. 21, 2014 From the European Patent Office Re. Application No. 14153703.5.
International Preliminary Report on Patentability Dated Nov. 6, 2014 From the International Bureau of WIPO Re. Application No. PCT/IL2013/050352.
Notice of Reason for Rejection Dated Nov. 11, 2014 From the Japanese Patent Office Re. Application No. 2012-515626 and Its Translation Into English.
Official Action Dated Sep. 15, 2014 From the US Patent and Trademark Office Re. U.S. Appl. No. 13/889,442.
Office Action Dated Apr. 9, 2014 From the Israel Patent Office Re. Application No. 229151 and Its Translation Into English.
Notice of Reason for Rejection Dated Jul. 8, 2014 From the Japanese Patent Office Re. Application No. 2012-515626 and Its Translation Into English.
Office Action Dated May 15, 2014 From the Israel Patent Office Re. Application No. 199468 and Its Translation Into English.
Official Action Dated Jun. 18, 2014 From the US Patent and Trademark Office Re. U.S. Appl. No. 13/978,740. (Part I).
Official Action Dated Jun. 18, 2014 From the US Patent and Trademark Office Re. U.S. Appl. No. 13/978,740. (Part II).
Official Action Dated Jun. 18, 2014 From the US Patent and Trademark Office Re. U.S. Appl. No. 13/978,740. (Part III).
Official Action Dated Jun. 18, 2014 From the US Patent and Trademark Office Re. U.S. Appl. No. 13/978,740. (Part IV).
Official Action Dated Jun. 18, 2014 From the US Patent and Trademark Office Re. U.S. Appl No. 13/978,740. (Part V).
Requisition by the Examiner on May 26, 2014 From the Canadian Intellectual Property Office Re. Application No. 2,673,484.
Restriction Official Action Dated Jul. 9, 2014 From the US Patent and Trademark Office Re. U.S. Appl. No. 13/889,442.
Carlisle et al. "CXCR4 Expression Heterogeneity in Neuroblastoma Cells Due to Ligand-Independent Regulation", Molecular Cancer, 8(126): 1-14, Dec. 22, 2009.
Munk Pedersen et al. "The Chimeric Anti-CD20 Antibody Rituximab Induces Apoptosis in B-Cell Chronic Lymphocytic Leukemia Cells Through A P38 Mitogen Activated Protein-Kinase-Dependent Mechanism", Blood, 99(4): 1314-1319, Feb. 15, 2002.
Rubin et al. "A Small-Molecule Antagonist of CXCR4 Inhibits Intracranial Growth of Primary Brain Tumors", Proc. Natl. Acad. Sci. USA, PNAS, 100(23): 13513-13518, Nov. 11, 2003.
Shim et al. "Chemokine Receptor CXCR4 as a Therapeutic Target for Neuroectodermal Tumors", Seminars in Cancer Biology, 19: 123-134, 2009.
Zhang et al. "Primitive Neuroectodermal Tumors of Adrenal Gland", Japanese Journal of Clinical Oncology, 40(8): 800-804, 2010.
Communication Pursuant to Article 94(3) EPC Dated Mar. 4, 2015 From the European Patent Office Re. Application No. 12702887.6.

Gross et al. "Chemokines in Neuroectodermal Cancers: The Crucial Growth Signal From the Soil", Seminars in Cancer Biology, 19(2): 103-110, Apr. 2009.
Russell et al. "CXCR4 Expression in Neuroblastoma Primary Tumors Is Associated With Clinical Presentation of Bone and Bone Marrow Metastases", Journal of Pediatric Surgery, 39(10): 1506-1511, Oct. 2004.
Zagozdzon et al. "Csk Homologous Kinase Inhibits CXCL12-CXCR4 Signaling in Neuroblastoma", International Journal of Oncology, 32(3): 619-623, Mar. 2008.
Official Action Dated Feb. 27, 2015 From the US Patent and Trademark Office Re. U.S. Appl. No. 13/978,740.
Summons to Attend Oral Proceedings Pursuant to Rule 115(1) EPC Dated Feb. 12, 2015 From the European Patent Office Re. Application No. 07849622.1.
Summons to Attend Oral Proceedings Pursuant to Rule 115(1) EPC Dated Dec. 9, 2014 From the European Patent Office Re. Application No. 07849622.1.
European Search Report and the European Search Opinion Dated Aug. 3, 2015 From the European Patent Office Re. Application No. 15166376.2.
Office Action Dated Jun. 22, 2015 From the Israel Patent Office Re. Application No. 229151 and Its Translation Into English.
Requisition by the Examiner Dated Jun. 25, 2015 From the Canadian Intellectual Property Office Re. Application No. 2,765,345.
Ghobrial el al. "Molecular Mechanisms Involved in Homing and Migration of Plasma Cells in Response to CXCR4 Stimulation and Downstream Activation of the P13K Pathway", Database Biosis [Online], XP002629050, Retrieved From Biosis, Database Accession No. PREV200510270159, Nov. 16, 2004. Abstract.
Martin et al. "Tumor Angiogenesis Is Associated With Plasma Levels of Stromal-Derived Factor-1[Alpha] in Patients With Multiple Myeloma", Clinical Cancer Research, XP055204518, 12(23): 6973-6977, Dec. 1, 2006. p. 6973.
Pitchford et al. "Differential Mobilization of Subsets of Progenitor Cells From the Bone Marrow", Cell Stem Cell, 4: 62-72, Jan. 9, 2009.
Ringe et al. "Towards In Situ Tissue Repair: Human Mesenchymal Stem Cells Express Chemokine Receptors CXCR1, CXCR2 and CCR2, and Migrate Upon Stimulation With CXCL8 But Not CCL2", Journal of Cellular Biochemistry, 101(1): 135-146, May 1, 2007.
Wynn et al. "A Small Proportion of Mesenchymal Stem Cells Strongly Expresses Functionally Active CXCR4 Receptor Capable of Promoting Migration to Bone Marrow", Blood, 104(9): 2643-2645, Prepublished Online Jul. 13, 2004.
Office Action Dated Sep. 8, 2015 From the Israel Patent Office Re. Application No. 218405.
Office Action Dated Aug. 12, 2015 From the Israel Patent Office Re. Application No. 199468.
Office Action Dated Aug. 13, 2015 From the Israel Patent Office Re. Application No. 199468 and Its Translation Into English.
Office Action Dated Aug. 13, 2015 From the Israel Patent Office Re. Application No. 218405 and Its Translation Into English.
Official Action Dated Dec. 21, 2015 From the US Patent and Trademark Office Re. U.S. Appl. No. 14/395,842.
Pottgen et al. "Intensified High-Dose Chemoradiotherapy With Induction Chemotherapy in Patients With Locally Advanced Non-Small-Cell Lung Cancer—Safety and Toxicity Results Within a Prospective Trial", International Journal of Radiation Oncology Biology Physics, 76(3): 809-815, Mar. 1, 2010.
Stewart et al. "World Cancer Report", International Agency for Research on Cancer, IARC Press, 5 Pages, Lyon, 2003.
Office Action Dated Feb. 15, 2016 From the Israel Patent Office Re. Application No. 240924 and Its Translation Into English.
Notice of Reexamination Dated Mar. 11, 2016 From the Patent Reexamination Board of State Intellectual Property Office of the People's Republic of China Re. Application No. 201080035931.5 and Its Translation Into English.

(56) References Cited

OTHER PUBLICATIONS

Restriction Official Action Dated Mar. 22, 2016 From the US Patent and Trademark Office Re. U.S. Appl. No. 14/771,513.
European Search Report and the European Search Opinion Dated Oct. 20, 2015 From the European Patent Office Re. Application No. 15169576.4.
International Preliminary Report on Patentability Dated Oct. 8, 2015 From the International Bureau of WIPO Re. Application No. PCT/IL2014/050303.
Requisition by the Examiner Dated Sep. 22, 2015 From the Canadian Intellectual Property Office Re. Application No. 2,673,484.
Abraham et al. "Enhanced Unique Pattern of Hematopoietic Cell Mobilization Induced by the CXCR4 Antagonist 4F-Benzoyl-TN14003", Online Supplement Figure 1, XP055155144, 1 P., May 24, 2007. Fig.1.
Chen et al. "CXCR4 Inhibition in Tumor Microenvironment Facilitates Anti-Programmed Death Receptor-1 Immunotherapy in Sorafenib-Treated Hepatocellular Carcinoma in Mice", Hepatology, 61: 1591-1602, May 2015.

Topalian et al. "Safety, Activity, and Immune Correlates of Anti-PD-1 Antibody in Cancer", The New England Journal of Medicine, 366(26): 2443-2454, Jun. 28, 2012.
Requisition by the Examiner Dated Apr. 15, 2015 From the Canadian Intellectual Property Office Re. Application No. 2,673,719.
Communication Pursuant to Article 94(3) EPC Dated Nov. 6, 2015 From the European Patent Office Re. Application No. 12702887.6.
Peled et al. "The High-Affinity CXCR4 Antagonist BKT140 Is Safe and Induces A Robust Mobilization of Human CD34+ Cells in Patients With Multiple Myeloma", Clinical Cancer Research, 20(2): 469-479, Published Online Nov. 18, 2013.
Notification of the Decision of Rejection Dated Mar. 31, 2014 From the State Intellectual Property Office of the People's Republic of China Re. Application No. 201080035931.5 and Its Translation Into English.
Communication Under Rule 71(3) EPC Dated Apr. 15, 2014 From the European Patent Office Re. Application No. 10176632.7.
Office Action Dated Apr. 3, 2014 From the Israel Patent Office Re. Application No. 218405 and Its Translation Into English.

\* cited by examiner

SEQUENCE LISTING

```
<160> NUMBER OF SEQ ID NOS: 77

<210> SEQ ID NO 1
<211> LENGTH: 14
<212> TYPE: PRT
<213> ORGANISM: Artificial
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: 4-fluorobenzoyl-arginine
<220> FEATURE:
<221> NAME/KEY: MOD_RES
<222> LOCATION: (3)..(3)
<223> OTHER INFORMATION: 3-((2-naphthyl) alanine
<220> FEATURE:
<221> NAME/KEY: MOD_RES
<222> LOCATION: (6)..(6)
<223> OTHER INFORMATION: citrulline
<220> FEATURE:
<221> NAME/KEY: MOD_RES
<222> LOCATION: (8)..(8)
<223> OTHER INFORMATION: D-lysine
<220> FEATURE:
<221> NAME/KEY: MOD_RES
<222> LOCATION: (12)..(12)
<223> OTHER INFORMATION: citrulline
<220> FEATURE:
<221> NAME/KEY: MOD_RES
<222> LOCATION: (14)..(14)
<223> OTHER INFORMATION: C' AMIDATED

<400> SEQUENCE: 1

Xaa Arg Xaa Cys Tyr Xaa Lys Xaa Pro Tyr Arg Xaa Cys Arg
1               5                   10

<210> SEQ ID NO 2
<211> LENGTH: 14
<212> TYPE: PRT
<213> ORGANISM: Artificial
<220> FEATURE:
<223> OTHER INFORMATION: SYNTHETIC PEPTIDE
<220> FEATURE:
<221> NAME/KEY: MOD_RES
<222> LOCATION: (1)..(1)
<223> OTHER INFORMATION: N' ACETYLATION
<220> FEATURE:
<221> NAME/KEY: MOD_RES
<222> LOCATION: (3)..(3)
<223> OTHER INFORMATION: 3-((2-naphthyl) alanine
<220> FEATURE:
<221> NAME/KEY: MOD_RES
<222> LOCATION: (6)..(6)
<223> OTHER INFORMATION: citrulline
<220> FEATURE:
<221> NAME/KEY: MOD_RES
<222> LOCATION: (8)..(8)
<223> OTHER INFORMATION: D-lysine
<220> FEATURE:
```

-continued

```
<221> NAME/KEY: MOD_RES
<222> LOCATION: (12)..(12)
<223> OTHER INFORMATION: citrulline

<400> SEQUENCE: 2

Arg Arg Xaa Cys Tyr Xaa Lys Xaa Pro Tyr Arg Xaa Cys Arg
1               5                   10

<210> SEQ ID NO 3
<211> LENGTH: 14
<212> TYPE: PRT
<213> ORGANISM: Artificial
<220> FEATURE:
<223> OTHER INFORMATION: SYNTHETIC PEPTIDE
<220> FEATURE:
<221> NAME/KEY: MOD_RES
<222> LOCATION: (1)..(1)
<223> OTHER INFORMATION: N' ACETYLATION
<220> FEATURE:
<221> NAME/KEY: MOD_RES
<222> LOCATION: (3)..(3)
<223> OTHER INFORMATION: 3-((2-naphthyl) alanine
<220> FEATURE:
<221> NAME/KEY: MOD_RES
<222> LOCATION: (8)..(8)
<223> OTHER INFORMATION: D-citrulline
<220> FEATURE:
<221> NAME/KEY: MOD_RES
<222> LOCATION: (12)..(12)
<223> OTHER INFORMATION: citrulline

<400> SEQUENCE: 3

Arg Arg Xaa Cys Tyr Arg Lys Xaa Pro Tyr Arg Xaa Cys Arg
1               5                   10

<210> SEQ ID NO 4
<211> LENGTH: 14
<212> TYPE: PRT
<213> ORGANISM: Artificial
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: N' ACETYLATED
<220> FEATURE:
<221> NAME/KEY: MOD_RES
<222> LOCATION: (3)..(3)
<223> OTHER INFORMATION: 3-((2-naphthyl) alanine
<220> FEATURE:
<221> NAME/KEY: MOD_RES
<222> LOCATION: (6)..(6)
<223> OTHER INFORMATION: citrulline
<220> FEATURE:
<221> NAME/KEY: MOD_RES
<222> LOCATION: (8)..(8)
<223> OTHER INFORMATION: D-citrulline
<220> FEATURE:
<221> NAME/KEY: MOD_RES
<222> LOCATION: (12)..(12)
<223> OTHER INFORMATION: citrulline

<400> SEQUENCE: 4

Arg Arg Xaa Cys Tyr Xaa Lys Xaa Pro Tyr Arg Xaa Cys Arg
1               5                   10

<210> SEQ ID NO 5
<211> LENGTH: 14
<212> TYPE: PRT
<213> ORGANISM: Artificial
<220> FEATURE:
<223> OTHER INFORMATION: synthetic peptide
<220> FEATURE:
```

```
<221> NAME/KEY: MOD_RES
<222> LOCATION: (1)..(1)
<223> OTHER INFORMATION: N' ACETYLATED
<220> FEATURE:
<221> NAME/KEY: MOD_RES
<222> LOCATION: (3)..(3)
<223> OTHER INFORMATION: 3-((2-naphthyl) alanine
<220> FEATURE:
<221> NAME/KEY: MOD_RES
<222> LOCATION: (6)..(6)
<223> OTHER INFORMATION: citrulline
<220> FEATURE:
<221> NAME/KEY: MOD_RES
<222> LOCATION: (8)..(8)
<223> OTHER INFORMATION: D-lysine
<220> FEATURE:
<221> NAME/KEY: MOD_RES
<222> LOCATION: (11)..(12)
<223> OTHER INFORMATION: citrulline

<400> SEQUENCE: 5

Arg Arg Xaa Cys Tyr Xaa Lys Xaa Pro Tyr Xaa Xaa Cys Arg
1               5                   10

<210> SEQ ID NO 6
<211> LENGTH: 14
<212> TYPE: PRT
<213> ORGANISM: Artificial
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: N' acetylated citrulline
<220> FEATURE:
<221> NAME/KEY: MOD_RES
<222> LOCATION: (3)..(3)
<223> OTHER INFORMATION: 3-((2-naphthyl) alanine
<220> FEATURE:
<221> NAME/KEY: MOD_RES
<222> LOCATION: (6)..(6)
<223> OTHER INFORMATION: citrulline
<220> FEATURE:
<221> NAME/KEY: MOD_RES
<222> LOCATION: (8)..(8)
<223> OTHER INFORMATION: D-lysine
<220> FEATURE:
<221> NAME/KEY: MOD_RES
<222> LOCATION: (12)..(12)
<223> OTHER INFORMATION: citrulline

<400> SEQUENCE: 6

Xaa Arg Xaa Cys Tyr Xaa Lys Xaa Pro Tyr Arg Xaa Cys Arg
1               5                   10

<210> SEQ ID NO 7
<211> LENGTH: 14
<212> TYPE: PRT
<213> ORGANISM: Artificial
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: N' acetylated citrulline
<220> FEATURE:
<221> NAME/KEY: MOD_RES
<222> LOCATION: (3)..(3)
<223> OTHER INFORMATION: 3-((2-naphthyl) alanine
<220> FEATURE:
<221> NAME/KEY: MOD_RES
<222> LOCATION: (8)..(8)
<223> OTHER INFORMATION: D-citrulline
<220> FEATURE:
<221> NAME/KEY: MOD_RES
```

<222> LOCATION: (12)..(12)
<223> OTHER INFORMATION: citrulline

<400> SEQUENCE: 7

Xaa Arg Xaa Cys Tyr Arg Lys Xaa Pro Tyr Arg Xaa Cys Arg
1               5                   10

<210> SEQ ID NO 8
<211> LENGTH: 14
<212> TYPE: PRT
<213> ORGANISM: Artificial
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: N' ACETYLATED
<220> FEATURE:
<221> NAME/KEY: MOD_RES
<222> LOCATION: (3)..(3)
<223> OTHER INFORMATION: 3-((2-naphthyl) alanine
<220> FEATURE:
<221> NAME/KEY: MOD_RES
<222> LOCATION: (8)..(8)
<223> OTHER INFORMATION: D-citrulline
<220> FEATURE:
<221> NAME/KEY: MOD_RES
<222> LOCATION: (11)..(12)
<223> OTHER INFORMATION: citrulline

<400> SEQUENCE: 8

Arg Arg Xaa Cys Tyr Arg Lys Xaa Pro Tyr Xaa Xaa Cys Arg
1               5                   10

<210> SEQ ID NO 9
<211> LENGTH: 14
<212> TYPE: PRT
<213> ORGANISM: Artificial
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: N' ACETYLATED citrulline
<220> FEATURE:
<221> NAME/KEY: MOD_RES
<222> LOCATION: (3)..(3)
<223> OTHER INFORMATION: 3-((2-naphthyl) alanine
<220> FEATURE:
<221> NAME/KEY: MOD_RES
<222> LOCATION: (8)..(8)
<223> OTHER INFORMATION: D-lysine
<220> FEATURE:
<221> NAME/KEY: MOD_RES
<222> LOCATION: (11)..(12)
<223> OTHER INFORMATION: citrulline

<400> SEQUENCE: 9

Xaa Arg Xaa Cys Tyr Arg Lys Xaa Pro Tyr Xaa Xaa Cys Arg
1               5                   10

<210> SEQ ID NO 10
<211> LENGTH: 14
<212> TYPE: PRT
<213> ORGANISM: Artificial
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: N' ACETYLATED
<220> FEATURE:
<221> NAME/KEY: MOD_RES

```
<222> LOCATION: (3)..(3)
<223> OTHER INFORMATION: 3-((2-naphthyl) alanine
<220> FEATURE:
<221> NAME/KEY: MOD_RES
<222> LOCATION: (6)..(6)
<223> OTHER INFORMATION: citrulline
<220> FEATURE:
<221> NAME/KEY: MOD_RES
<222> LOCATION: (8)..(8)
<223> OTHER INFORMATION: D-citrulline
<220> FEATURE:
<221> NAME/KEY: MOD_RES
<222> LOCATION: (12)..(12)
<223> OTHER INFORMATION: citrulline
<220> FEATURE:
<221> NAME/KEY: MOD_RES
<222> LOCATION: (14)..(14)
<223> OTHER INFORMATION: C' AMIDATED

<400> SEQUENCE: 10

Arg Arg Xaa Cys Tyr Xaa Lys Xaa Pro Tyr Arg Xaa Cys Arg
1               5                   10

<210> SEQ ID NO 11
<211> LENGTH: 14
<212> TYPE: PRT
<213> ORGANISM: Artificial
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: N' ACETYLATED
<220> FEATURE:
<221> NAME/KEY: MOD_RES
<222> LOCATION: (3)..(3)
<223> OTHER INFORMATION: 3-((2-naphthyl) alanine
<220> FEATURE:
<221> NAME/KEY: MOD_RES
<222> LOCATION: (6)..(6)
<223> OTHER INFORMATION: citrulline
<220> FEATURE:
<221> NAME/KEY: MOD_RES
<222> LOCATION: (8)..(8)
<223> OTHER INFORMATION: D-lysine
<220> FEATURE:
<221> NAME/KEY: MOD_RES
<222> LOCATION: (11)..(12)
<223> OTHER INFORMATION: citrulline
<220> FEATURE:
<221> NAME/KEY: MOD_RES
<222> LOCATION: (14)..(14)
<223> OTHER INFORMATION: C' AMIDATED

<400> SEQUENCE: 11

Arg Arg Xaa Cys Tyr Xaa Lys Xaa Pro Tyr Xaa Xaa Cys Arg
1               5                   10

<210> SEQ ID NO 12
<211> LENGTH: 14
<212> TYPE: PRT
<213> ORGANISM: Artificial
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: N' ACETYLATED citrulline
<220> FEATURE:
<221> NAME/KEY: MOD_RES
<222> LOCATION: (3)..(3)
<223> OTHER INFORMATION: 3-((2-naphthyl) alanine
<220> FEATURE:
<221> NAME/KEY: MOD_RES
<222> LOCATION: (6)..(6)
```

```
<223> OTHER INFORMATION: citrulline
<220> FEATURE:
<221> NAME/KEY: MOD_RES
<222> LOCATION: (8)..(8)
<223> OTHER INFORMATION: D-lysine
<220> FEATURE:
<221> NAME/KEY: MOD_RES
<222> LOCATION: (12)..(12)
<223> OTHER INFORMATION: citrulline
<220> FEATURE:
<221> NAME/KEY: MOD_RES
<222> LOCATION: (14)..(14)
<223> OTHER INFORMATION: AMIDATED

<400> SEQUENCE: 12

Xaa Arg Xaa Cys Tyr Xaa Lys Xaa Pro Tyr Arg Xaa Cys Arg
1               5                   10

<210> SEQ ID NO 13
<211> LENGTH: 14
<212> TYPE: PRT
<213> ORGANISM: Artificial
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: N' ACETYLATED citrulline
<220> FEATURE:
<221> NAME/KEY: MOD_RES
<222> LOCATION: (3)..(3)
<223> OTHER INFORMATION: 3-((2-naphthyl) alanine
<220> FEATURE:
<221> NAME/KEY: MOD_RES
<222> LOCATION: (8)..(8)
<223> OTHER INFORMATION: D-citrulline
<220> FEATURE:
<221> NAME/KEY: MOD_RES
<222> LOCATION: (12)..(12)
<223> OTHER INFORMATION: citrulline
<220> FEATURE:
<221> NAME/KEY: MOD_RES
<222> LOCATION: (14)..(14)
<223> OTHER INFORMATION: C' AMIDATED

<400> SEQUENCE: 13

Xaa Arg Xaa Cys Tyr Arg Lys Xaa Pro Tyr Arg Xaa Cys Arg
1               5                   10

<210> SEQ ID NO 14
<211> LENGTH: 14
<212> TYPE: PRT
<213> ORGANISM: Artificial
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: N' ACETYLATED
<220> FEATURE:
<221> NAME/KEY: MOD_RES
<222> LOCATION: (3)..(3)
<223> OTHER INFORMATION: 3-((2-naphthyl) alanine
<220> FEATURE:
<221> NAME/KEY: MOD_RES
<222> LOCATION: (8)..(8)
<223> OTHER INFORMATION: D-citrulline
<220> FEATURE:
<221> NAME/KEY: MOD_RES
<222> LOCATION: (11)..(12)
<223> OTHER INFORMATION: citrulline
<220> FEATURE:
<221> NAME/KEY: MOD_RES
<222> LOCATION: (14)..(14)
<223> OTHER INFORMATION: C' AMIDATED
```

<400> SEQUENCE: 14

Arg Arg Xaa Cys Tyr Arg Lys Xaa Pro Tyr Xaa Xaa Cys Arg
1               5                   10

<210> SEQ ID NO 15
<211> LENGTH: 14
<212> TYPE: PRT
<213> ORGANISM: Artificial
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: N' ACETYLATED citrulline
<220> FEATURE:
<221> NAME/KEY: MOD_RES
<222> LOCATION: (3)..(3)
<223> OTHER INFORMATION: 3-((2-naphthyl) alanine
<220> FEATURE:
<221> NAME/KEY: MOD_RES
<222> LOCATION: (8)..(8)
<223> OTHER INFORMATION: D-lysine
<220> FEATURE:
<221> NAME/KEY: MOD_RES
<222> LOCATION: (11)..(12)
<223> OTHER INFORMATION: citrulline
<220> FEATURE:
<221> NAME/KEY: MOD_RES
<222> LOCATION: (14)..(14)
<223> OTHER INFORMATION: C' AMIDATED

<400> SEQUENCE: 15

Xaa Arg Xaa Cys Tyr Arg Lys Xaa Pro Tyr Xaa Xaa Cys Arg
1               5                   10

<210> SEQ ID NO 16
<211> LENGTH: 14
<212> TYPE: PRT
<213> ORGANISM: Artificial
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: D-glutamic acid
<220> FEATURE:
<221> NAME/KEY: MOD_RES
<222> LOCATION: (3)..(3)
<223> OTHER INFORMATION: 3-((2-naphthyl) alanine
<220> FEATURE:
<221> NAME/KEY: MOD_RES
<222> LOCATION: (8)..(8)
<223> OTHER INFORMATION: D-lysine
<220> FEATURE:
<221> NAME/KEY: MOD_RES
<222> LOCATION: (12)..(12)
<223> OTHER INFORMATION: citrulline

<400> SEQUENCE: 16

Xaa Arg Xaa Cys Tyr Arg Lys Xaa Pro Tyr Arg Xaa Cys Arg
1               5                   10

<210> SEQ ID NO 17
<211> LENGTH: 14
<212> TYPE: PRT
<213> ORGANISM: Artificial
<220> FEATURE:
<223> OTHER INFORMATION: synthetic peptide
<220> FEATURE:
<221> NAME/KEY: MOD_RES
<222> LOCATION: (3)..(3)
<223> OTHER INFORMATION: 3-((2-naphthyl) alanine

```
<220> FEATURE:
<221> NAME/KEY: MOD_RES
<222> LOCATION: (8)..(8)
<223> OTHER INFORMATION: D-lysine
<220> FEATURE:
<221> NAME/KEY: MOD_RES
<222> LOCATION: (12)..(12)
<223> OTHER INFORMATION: citrulline

<400> SEQUENCE: 17

Arg Glu Xaa Cys Tyr Arg Lys Xaa Pro Tyr Arg Xaa Cys Arg
1               5                   10

<210> SEQ ID NO 18
<211> LENGTH: 14
<212> TYPE: PRT
<213> ORGANISM: Artificial
<220> FEATURE:
<223> OTHER INFORMATION: synthetic peptide
<220> FEATURE:
<221> NAME/KEY: MOD_RES
<222> LOCATION: (3)..(3)
<223> OTHER INFORMATION: 3-((2-naphthyl) alanine
<220> FEATURE:
<221> NAME/KEY: MOD_RES
<222> LOCATION: (8)..(8)
<223> OTHER INFORMATION: D-lysine
<220> FEATURE:
<221> NAME/KEY: MOD_RES
<222> LOCATION: (12)..(12)
<223> OTHER INFORMATION: citrulline

<400> SEQUENCE: 18

Arg Arg Xaa Cys Tyr Glu Lys Xaa Pro Tyr Arg Xaa Cys Arg
1               5                   10

<210> SEQ ID NO 19
<211> LENGTH: 14
<212> TYPE: PRT
<213> ORGANISM: Artificial
<220> FEATURE:
<223> OTHER INFORMATION: synthetic peptide
<220> FEATURE:
<221> NAME/KEY: MOD_RES
<222> LOCATION: (3)..(3)
<223> OTHER INFORMATION: 3-((2-naphthyl) alanine
<220> FEATURE:
<221> NAME/KEY: MOD_RES
<222> LOCATION: (8)..(8)
<223> OTHER INFORMATION: D-lysine
<220> FEATURE:
<221> NAME/KEY: MOD_RES
<222> LOCATION: (12)..(12)
<223> OTHER INFORMATION: citrulline

<400> SEQUENCE: 19

Arg Arg Xaa Cys Tyr Arg Glu Xaa Pro Tyr Arg Xaa Cys Arg
1               5                   10

<210> SEQ ID NO 20
<211> LENGTH: 14
<212> TYPE: PRT
<213> ORGANISM: Artificial
<220> FEATURE:
<223> OTHER INFORMATION: synthetic peptide
<220> FEATURE:
<221> NAME/KEY: MOD_RES
<222> LOCATION: (3)..(3)
<223> OTHER INFORMATION: 3-((2-naphthyl) alanine
<220> FEATURE:
<221> NAME/KEY: MOD_RES
<222> LOCATION: (8)..(8)
<223> OTHER INFORMATION: D-glutamic acid
```

-continued

```
<220> FEATURE:
<221> NAME/KEY: MOD_RES
<222> LOCATION: (12)..(12)
<223> OTHER INFORMATION: citrulline

<400> SEQUENCE: 20

Arg Arg Xaa Cys Tyr Arg Lys Xaa Pro Tyr Arg Xaa Cys Arg
1               5                   10

<210> SEQ ID NO 21
<211> LENGTH: 14
<212> TYPE: PRT
<213> ORGANISM: Artificial
<220> FEATURE:
<223> OTHER INFORMATION: synthetic peptide
<220> FEATURE:
<221> NAME/KEY: MOD_RES
<222> LOCATION: (3)..(3)
<223> OTHER INFORMATION: 3-((2-naphthyl) alanine
<220> FEATURE:
<221> NAME/KEY: MOD_RES
<222> LOCATION: (8)..(8)
<223> OTHER INFORMATION: D-lysine
<220> FEATURE:
<221> NAME/KEY: MOD_RES
<222> LOCATION: (12)..(12)
<223> OTHER INFORMATION: citrulline

<400> SEQUENCE: 21

Arg Arg Xaa Cys Tyr Arg Lys Xaa Pro Tyr Glu Xaa Cys Arg
1               5                   10

<210> SEQ ID NO 22
<211> LENGTH: 14
<212> TYPE: PRT
<213> ORGANISM: Artificial
<220> FEATURE:
<223> OTHER INFORMATION: synthetic peptide
<220> FEATURE:
<221> NAME/KEY: MOD_RES
<222> LOCATION: (3)..(3)
<223> OTHER INFORMATION: 3-((2-naphthyl) alanine
<220> FEATURE:
<221> NAME/KEY: MOD_RES
<222> LOCATION: (8)..(8)
<223> OTHER INFORMATION: D-lysine
<220> FEATURE:
<221> NAME/KEY: MOD_RES
<222> LOCATION: (12)..(12)
<223> OTHER INFORMATION: citrulline

<400> SEQUENCE: 22

Arg Arg Xaa Cys Tyr Arg Lys Xaa Pro Tyr Arg Xaa Cys Glu
1               5                   10

<210> SEQ ID NO 23
<211> LENGTH: 14
<212> TYPE: PRT
<213> ORGANISM: Artificial
<220> FEATURE:
<223> OTHER INFORMATION: synthetic peptide
<220> FEATURE:
<221> NAME/KEY: MOD_RES
<222> LOCATION: (3)..(3)
<223> OTHER INFORMATION: 3-((2-naphthyl) alanine
<220> FEATURE:
<221> NAME/KEY: MOD_RES
<222> LOCATION: (6)..(6)
<223> OTHER INFORMATION: citrulline
<220> FEATURE:
<221> NAME/KEY: MOD_RES
<222> LOCATION: (8)..(8)
<223> OTHER INFORMATION: D-glutamic acid
```

```
<220> FEATURE:
<221> NAME/KEY: MOD_RES
<222> LOCATION: (12)..(12)
<223> OTHER INFORMATION: citrulline
<220> FEATURE:
<221> NAME/KEY: MOD_RES
<222> LOCATION: (14)..(14)
<223> OTHER INFORMATION: C' amidated

<400> SEQUENCE: 23

Arg Arg Xaa Cys Tyr Xaa Lys Xaa Pro Tyr Arg Xaa Cys Arg
1               5                   10

<210> SEQ ID NO 24
<211> LENGTH: 14
<212> TYPE: PRT
<213> ORGANISM: Artificial
<220> FEATURE:
<223> OTHER INFORMATION: synthetic peptide
<220> FEATURE:
<221> NAME/KEY: MOD_RES
<222> LOCATION: (3)..(3)
<223> OTHER INFORMATION: 3-((2-naphthyl) alanine
<220> FEATURE:
<221> NAME/KEY: MOD_RES
<222> LOCATION: (6)..(6)
<223> OTHER INFORMATION: D-glutamic acid
<220> FEATURE:
<221> NAME/KEY: MOD_RES
<222> LOCATION: (8)..(8)
<223> OTHER INFORMATION: D-citrulline
<220> FEATURE:
<221> NAME/KEY: MOD_RES
<222> LOCATION: (12)..(12)
<223> OTHER INFORMATION: citrulline
<220> FEATURE:
<221> NAME/KEY: MOD_RES
<222> LOCATION: (14)..(14)
<223> OTHER INFORMATION: c' amidated

<400> SEQUENCE: 24

Arg Arg Xaa Cys Tyr Xaa Lys Xaa Pro Tyr Arg Xaa Cys Arg
1               5                   10

<210> SEQ ID NO 25
<211> LENGTH: 14
<212> TYPE: PRT
<213> ORGANISM: Artificial
<220> FEATURE:
<223> OTHER INFORMATION: synthetic peptide
<220> FEATURE:
<221> NAME/KEY: MOD_RES
<222> LOCATION: (3)..(3)
<223> OTHER INFORMATION: 3-((2-naphthyl) alanine
<220> FEATURE:
<221> NAME/KEY: MOD_RES
<222> LOCATION: (6)..(6)
<223> OTHER INFORMATION: D-glutamic acid
<220> FEATURE:
<221> NAME/KEY: MOD_RES
<222> LOCATION: (8)..(8)
<223> OTHER INFORMATION: D-glutamic acid
<220> FEATURE:
<221> NAME/KEY: MOD_RES
<222> LOCATION: (12)..(12)
<223> OTHER INFORMATION: citrulline
<220> FEATURE:
<221> NAME/KEY: MOD_RES
<222> LOCATION: (14)..(14)
<223> OTHER INFORMATION: c' amidated

<400> SEQUENCE: 25

Arg Arg Xaa Cys Tyr Xaa Lys Xaa Pro Tyr Arg Xaa Cys Arg
1               5                   10
```

-continued

```
<210> SEQ ID NO 26
<211> LENGTH: 14
<212> TYPE: PRT
<213> ORGANISM: Artificial
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: D-glutamic acid
<220> FEATURE:
<221> NAME/KEY: MOD_RES
<222> LOCATION: (3)..(3)
<223> OTHER INFORMATION: 3-((2-naphthyl) alanine
<220> FEATURE:
<221> NAME/KEY: MOD_RES
<222> LOCATION: (6)..(6)
<223> OTHER INFORMATION: citrulline
<220> FEATURE:
<221> NAME/KEY: MOD_RES
<222> LOCATION: (8)..(8)
<223> OTHER INFORMATION: D-glutamic acid
<220> FEATURE:
<221> NAME/KEY: MOD_RES
<222> LOCATION: (12)..(12)
<223> OTHER INFORMATION: citrulline
<220> FEATURE:
<221> NAME/KEY: MOD_RES
<222> LOCATION: (14)..(14)
<223> OTHER INFORMATION: c' amidated

<400> SEQUENCE: 26

Xaa Arg Xaa Cys Tyr Xaa Lys Xaa Pro Tyr Arg Xaa Cys Arg
1               5                   10

<210> SEQ ID NO 27
<211> LENGTH: 14
<212> TYPE: PRT
<213> ORGANISM: Artificial
<220> FEATURE:
<223> OTHER INFORMATION: synthetic peptide
<220> FEATURE:
<221> NAME/KEY: MOD_RES
<222> LOCATION: (3)..(3)
<223> OTHER INFORMATION: 3-((2-naphthyl) alanine
<220> FEATURE:
<221> NAME/KEY: MOD_RES
<222> LOCATION: (6)..(6)
<223> OTHER INFORMATION: citrulline
<220> FEATURE:
<221> NAME/KEY: MOD_RES
<222> LOCATION: (8)..(8)
<223> OTHER INFORMATION: D-glutamic acid
<220> FEATURE:
<221> NAME/KEY: MOD_RES
<222> LOCATION: (10)..(10)
<223> OTHER INFORMATION: D-glutamic acid
<220> FEATURE:
<221> NAME/KEY: MOD_RES
<222> LOCATION: (12)..(12)
<223> OTHER INFORMATION: citrulline
<220> FEATURE:
<221> NAME/KEY: MOD_RES
<222> LOCATION: (14)..(14)
<223> OTHER INFORMATION: c' amidated

<400> SEQUENCE: 27

Arg Arg Xaa Cys Tyr Xaa Lys Xaa Pro Xaa Arg Xaa Cys Arg
1               5                   10

<210> SEQ ID NO 28
<211> LENGTH: 14
<212> TYPE: PRT
```

<213> ORGANISM: Artificial
<220> FEATURE:
<223> OTHER INFORMATION: synthetic peptide
<220> FEATURE:
<221> NAME/KEY: MOD_RES
<222> LOCATION: (3)..(3)
<223> OTHER INFORMATION: 3-((2-naphthyl) alanine
<220> FEATURE:
<221> NAME/KEY: MOD_RES
<222> LOCATION: (6)..(6)
<223> OTHER INFORMATION: citrulline
<220> FEATURE:
<221> NAME/KEY: MOD_RES
<222> LOCATION: (8)..(8)
<223> OTHER INFORMATION: D-glutamic acid
<220> FEATURE:
<221> NAME/KEY: MOD_RES
<222> LOCATION: (12)..(12)
<223> OTHER INFORMATION: D-glutamic acid
<220> FEATURE:
<221> NAME/KEY: MOD_RES
<222> LOCATION: (14)..(14)
<223> OTHER INFORMATION: c' amidated

<400> SEQUENCE: 28

Arg Arg Xaa Cys Tyr Xaa Lys Xaa Pro Tyr Arg Xaa Cys Arg
1               5                   10

<210> SEQ ID NO 29
<211> LENGTH: 14
<212> TYPE: PRT
<213> ORGANISM: Artificial
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: N' ACETYLATED D-glutamic acid
<220> FEATURE:
<221> NAME/KEY: MOD_RES
<222> LOCATION: (3)..(3)
<223> OTHER INFORMATION: 3-((2-naphthyl) alanine
<220> FEATURE:
<221> NAME/KEY: MOD_RES
<222> LOCATION: (6)..(6)
<223> OTHER INFORMATION: citrulline
<220> FEATURE:
<221> NAME/KEY: MOD_RES
<222> LOCATION: (8)..(8)
<223> OTHER INFORMATION: D-glutamic acid
<220> FEATURE:
<221> NAME/KEY: MOD_RES
<222> LOCATION: (12)..(12)
<223> OTHER INFORMATION: citrulline
<220> FEATURE:
<221> NAME/KEY: MOD_RES
<222> LOCATION: (14)..(14)
<223> OTHER INFORMATION: c' amidated

<400> SEQUENCE: 29

Xaa Arg Xaa Cys Tyr Xaa Lys Xaa Pro Tyr Arg Xaa Cys Arg
1               5                   10

<210> SEQ ID NO 30
<211> LENGTH: 14
<212> TYPE: PRT
<213> ORGANISM: Artificial
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: N' ACETYLATED
<220> FEATURE:
<221> NAME/KEY: MOD_RES

```
<222> LOCATION: (3)..(3)
<223> OTHER INFORMATION: 3-((2-naphthyl) alanine
<220> FEATURE:
<221> NAME/KEY: MOD_RES
<222> LOCATION: (6)..(6)
<223> OTHER INFORMATION: citrulline
<220> FEATURE:
<221> NAME/KEY: MOD_RES
<222> LOCATION: (8)..(8)
<223> OTHER INFORMATION: D-glutamic acid
<220> FEATURE:
<221> NAME/KEY: MOD_RES
<222> LOCATION: (10)..(10)
<223> OTHER INFORMATION: D-glutamic acid
<220> FEATURE:
<221> NAME/KEY: MOD_RES
<222> LOCATION: (12)..(12)
<223> OTHER INFORMATION: citrulline
<220> FEATURE:
<221> NAME/KEY: MOD_RES
<222> LOCATION: (14)..(14)
<223> OTHER INFORMATION: c' amidated

<400> SEQUENCE: 30

Arg Arg Xaa Cys Tyr Xaa Lys Xaa Pro Xaa Arg Xaa Cys Arg
1               5                   10

<210> SEQ ID NO 31
<211> LENGTH: 14
<212> TYPE: PRT
<213> ORGANISM: Artificial
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: N' ACETYLATED
<220> FEATURE:
<221> NAME/KEY: MOD_RES
<222> LOCATION: (3)..(3)
<223> OTHER INFORMATION: 3-((2-naphthyl) alanine
<220> FEATURE:
<221> NAME/KEY: MOD_RES
<222> LOCATION: (6)..(6)
<223> OTHER INFORMATION: citrulline
<220> FEATURE:
<221> NAME/KEY: MOD_RES
<222> LOCATION: (8)..(8)
<223> OTHER INFORMATION: D-glutamic acid
<220> FEATURE:
<221> NAME/KEY: MOD_RES
<222> LOCATION: (12)..(12)
<223> OTHER INFORMATION: D-glutamic acid
<220> FEATURE:
<221> NAME/KEY: MOD_RES
<222> LOCATION: (14)..(14)
<223> OTHER INFORMATION: c' amidated

<400> SEQUENCE: 31

Arg Arg Xaa Cys Tyr Xaa Lys Xaa Pro Tyr Arg Xaa Cys Arg
1               5                   10

<210> SEQ ID NO 32
<211> LENGTH: 14
<212> TYPE: PRT
<213> ORGANISM: Artificial
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: N' ACETYLATED
<220> FEATURE:
<221> NAME/KEY: MOD_RES
<222> LOCATION: (3)..(3)
```

```
<223> OTHER INFORMATION: 3-((2-naphthyl) alanine
<220> FEATURE:
<221> NAME/KEY: MOD_RES
<222> LOCATION: (6)..(6)
<223> OTHER INFORMATION: citrulline
<220> FEATURE:
<221> NAME/KEY: MOD_RES
<222> LOCATION: (8)..(8)
<223> OTHER INFORMATION: D-glutamic acid
<220> FEATURE:
<221> NAME/KEY: MOD_RES
<222> LOCATION: (12)..(12)
<223> OTHER INFORMATION: citrulline
<220> FEATURE:
<221> NAME/KEY: MOD_RES
<222> LOCATION: (14)..(14)
<223> OTHER INFORMATION: c' amidated

<400> SEQUENCE: 32

Arg Arg Xaa Cys Tyr Xaa Lys Xaa Pro Tyr Arg Xaa Cys Arg
1               5                   10

<210> SEQ ID NO 33
<211> LENGTH: 14
<212> TYPE: PRT
<213> ORGANISM: Artificial
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: Guanyl-arginine
<220> FEATURE:
<221> NAME/KEY: MOD_RES
<222> LOCATION: (3)..(3)
<223> OTHER INFORMATION: 3-((2-naphthyl) alanine
<220> FEATURE:
<221> NAME/KEY: MOD_RES
<222> LOCATION: (6)..(6)
<223> OTHER INFORMATION: citrulline
<220> FEATURE:
<221> NAME/KEY: MOD_RES
<222> LOCATION: (8)..(8)
<223> OTHER INFORMATION: D-glutamic acid
<220> FEATURE:
<221> NAME/KEY: MOD_RES
<222> LOCATION: (12)..(12)
<223> OTHER INFORMATION: citrulline
<220> FEATURE:
<221> NAME/KEY: MOD_RES
<222> LOCATION: (14)..(14)
<223> OTHER INFORMATION: c' amidated

<400> SEQUENCE: 33

Xaa Arg Xaa Cys Tyr Xaa Lys Xaa Pro Tyr Arg Xaa Cys Arg
1               5                   10

<210> SEQ ID NO 34
<211> LENGTH: 14
<212> TYPE: PRT
<213> ORGANISM: Artificial
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: Tetramethylguanyl-arginine
<220> FEATURE:
<221> NAME/KEY: MOD_RES
<222> LOCATION: (3)..(3)
<223> OTHER INFORMATION: 3-((2-naphthyl) alanine
<220> FEATURE:
<221> NAME/KEY: MOD_RES
<222> LOCATION: (6)..(6)
<223> OTHER INFORMATION: citrulline
```

```
<220> FEATURE:
<221> NAME/KEY: MOD_RES
<222> LOCATION: (8)..(8)
<223> OTHER INFORMATION: D-glutamic acid
<220> FEATURE:
<221> NAME/KEY: MOD_RES
<222> LOCATION: (12)..(12)
<223> OTHER INFORMATION: citrulline
<220> FEATURE:
<221> NAME/KEY: MOD_RES
<222> LOCATION: (14)..(14)
<223> OTHER INFORMATION: c' amidated

<400> SEQUENCE: 34

Xaa Arg Xaa Cys Tyr Xaa Lys Xaa Pro Tyr Arg Xaa Cys Arg
1               5                   10

<210> SEQ ID NO 35
<211> LENGTH: 13
<212> TYPE: PRT
<213> ORGANISM: Artificial
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: Tetramethylguanyl-arginine
<220> FEATURE:
<221> NAME/KEY: MOD_RES
<222> LOCATION: (2)..(2)
<223> OTHER INFORMATION: 3-((2-naphthyl) alanine
<220> FEATURE:
<221> NAME/KEY: MOD_RES
<222> LOCATION: (5)..(5)
<223> OTHER INFORMATION: citrulline
<220> FEATURE:
<221> NAME/KEY: MOD_RES
<222> LOCATION: (7)..(7)
<223> OTHER INFORMATION: D-glutamic acid
<220> FEATURE:
<221> NAME/KEY: MOD_RES
<222> LOCATION: (11)..(11)
<223> OTHER INFORMATION: citrulline
<220> FEATURE:
<221> NAME/KEY: MOD_RES
<222> LOCATION: (13)..(13)
<223> OTHER INFORMATION: c' amidated

<400> SEQUENCE: 35

Xaa Xaa Cys Tyr Xaa Lys Xaa Pro Tyr Arg Xaa Cys Arg
1               5                   10

<210> SEQ ID NO 36
<211> LENGTH: 14
<212> TYPE: PRT
<213> ORGANISM: Artificial
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: 4-fluorobenzoyl-arginine
<220> FEATURE:
<221> NAME/KEY: MOD_RES
<222> LOCATION: (3)..(3)
<223> OTHER INFORMATION: 3-((2-naphthyl) alanine
<220> FEATURE:
<221> NAME/KEY: MOD_RES
<222> LOCATION: (6)..(6)
<223> OTHER INFORMATION: citrulline
<220> FEATURE:
<221> NAME/KEY: MOD_RES
<222> LOCATION: (8)..(8)
<223> OTHER INFORMATION: D-glutamic acid
<220> FEATURE:
```

```
<221> NAME/KEY: MOD_RES
<222> LOCATION: (12)..(12)
<223> OTHER INFORMATION: citrulline
<220> FEATURE:
<221> NAME/KEY: MOD_RES
<222> LOCATION: (14)..(14)
<223> OTHER INFORMATION: amidated

<400> SEQUENCE: 36

Xaa Arg Xaa Cys Tyr Xaa Lys Xaa Pro Tyr Arg Xaa Cys Arg
1               5                   10

<210> SEQ ID NO 37
<211> LENGTH: 14
<212> TYPE: PRT
<213> ORGANISM: Artificial
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: 2-fluorobenzoyl-arginine
<220> FEATURE:
<221> NAME/KEY: MOD_RES
<222> LOCATION: (3)..(3)
<223> OTHER INFORMATION: 3-((2-naphthyl) alanine
<220> FEATURE:
<221> NAME/KEY: MOD_RES
<222> LOCATION: (6)..(6)
<223> OTHER INFORMATION: citrulline
<220> FEATURE:
<221> NAME/KEY: MOD_RES
<222> LOCATION: (8)..(8)
<223> OTHER INFORMATION: D-glutamic acid
<220> FEATURE:
<221> NAME/KEY: MOD_RES
<222> LOCATION: (12)..(12)
<223> OTHER INFORMATION: citrulline
<220> FEATURE:
<221> NAME/KEY: MOD_RES
<222> LOCATION: (14)..(14)
<223> OTHER INFORMATION: c' amidated

<400> SEQUENCE: 37

Xaa Arg Xaa Cys Tyr Xaa Lys Xaa Pro Tyr Arg Xaa Cys Arg
1               5                   10

<210> SEQ ID NO 38
<211> LENGTH: 13
<212> TYPE: PRT
<213> ORGANISM: Artificial
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: 5-aminopentanoyl-arginine
<220> FEATURE:
<221> NAME/KEY: MOD_RES
<222> LOCATION: (2)..(2)
<223> OTHER INFORMATION: 3-((2-naphthyl) alanine
<220> FEATURE:
<221> NAME/KEY: MOD_RES
<222> LOCATION: (5)..(5)
<223> OTHER INFORMATION: citrulline
<220> FEATURE:
<221> NAME/KEY: MOD_RES
<222> LOCATION: (7)..(7)
<223> OTHER INFORMATION: D-glutamic acid
<220> FEATURE:
<221> NAME/KEY: MOD_RES
<222> LOCATION: (11)..(11)
<223> OTHER INFORMATION: citrulline
<220> FEATURE:
<221> NAME/KEY: MOD_RES
```

```
<222> LOCATION: (13)..(13)
<223> OTHER INFORMATION: c' amidated

<400> SEQUENCE: 38

Xaa Xaa Cys Tyr Xaa Lys Xaa Pro Tyr Arg Xaa Cys Arg
1               5                   10

<210> SEQ ID NO 39
<211> LENGTH: 14
<212> TYPE: PRT
<213> ORGANISM: Artificial
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: 2-desamino-arginyl
<220> FEATURE:
<221> NAME/KEY: MOD_RES
<222> LOCATION: (3)..(3)
<223> OTHER INFORMATION: 3-((2-naphthyl) alanine
<220> FEATURE:
<221> NAME/KEY: MOD_RES
<222> LOCATION: (6)..(6)
<223> OTHER INFORMATION: citrulline
<220> FEATURE:
<221> NAME/KEY: MOD_RES
<222> LOCATION: (8)..(8)
<223> OTHER INFORMATION: D-glutamic acid
<220> FEATURE:
<221> NAME/KEY: MOD_RES
<222> LOCATION: (12)..(12)
<223> OTHER INFORMATION: citrulline
<220> FEATURE:
<221> NAME/KEY: MOD_RES
<222> LOCATION: (14)..(14)
<223> OTHER INFORMATION: c' amidated

<400> SEQUENCE: 39

Xaa Arg Xaa Cys Tyr Xaa Lys Xaa Pro Tyr Arg Xaa Cys Arg
1               5                   10

<210> SEQ ID NO 40
<211> LENGTH: 13
<212> TYPE: PRT
<213> ORGANISM: Artificial
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: Guanyl-arginine
<220> FEATURE:
<221> NAME/KEY: MOD_RES
<222> LOCATION: (2)..(2)
<223> OTHER INFORMATION: 3-((2-naphthyl) alanine
<220> FEATURE:
<221> NAME/KEY: MOD_RES
<222> LOCATION: (5)..(5)
<223> OTHER INFORMATION: citrulline
<220> FEATURE:
<221> NAME/KEY: MOD_RES
<222> LOCATION: (7)..(7)
<223> OTHER INFORMATION: D-glutamic acid
<220> FEATURE:
<221> NAME/KEY: MOD_RES
<222> LOCATION: (11)..(11)
<223> OTHER INFORMATION: citrulline
<220> FEATURE:
<221> NAME/KEY: MOD_RES
<222> LOCATION: (13)..(13)
<223> OTHER INFORMATION: c' amidated

<400> SEQUENCE: 40
```

```
Xaa Xaa Cys Tyr Xaa Lys Xaa Pro Tyr Arg Xaa Cys Arg
1               5                   10
```

<210> SEQ ID NO 41
<211> LENGTH: 13
<212> TYPE: PRT
<213> ORGANISM: Artificial
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: Succinyl-arginine
<220> FEATURE:
<221> NAME/KEY: MOD_RES
<222> LOCATION: (2)..(2)
<223> OTHER INFORMATION: 3-((2-naphthyl) alanine
<220> FEATURE:
<221> NAME/KEY: MOD_RES
<222> LOCATION: (5)..(5)
<223> OTHER INFORMATION: citrulline
<220> FEATURE:
<221> NAME/KEY: MOD_RES
<222> LOCATION: (7)..(7)
<223> OTHER INFORMATION: D-glutamic acid
<220> FEATURE:
<221> NAME/KEY: MOD_RES
<222> LOCATION: (11)..(11)
<223> OTHER INFORMATION: citrulline
<220> FEATURE:
<221> NAME/KEY: MOD_RES
<222> LOCATION: (13)..(13)
<223> OTHER INFORMATION: c' amidated

<400> SEQUENCE: 41

```
Xaa Xaa Cys Tyr Xaa Lys Xaa Pro Tyr Arg Xaa Cys Arg
1               5                   10
```

<210> SEQ ID NO 42
<211> LENGTH: 13
<212> TYPE: PRT
<213> ORGANISM: Artificial
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: Glutaryl-arginine
<220> FEATURE:
<221> NAME/KEY: MOD_RES
<222> LOCATION: (2)..(2)
<223> OTHER INFORMATION: 3-((2-naphthyl) alanine
<220> FEATURE:
<221> NAME/KEY: MOD_RES
<222> LOCATION: (5)..(5)
<223> OTHER INFORMATION: citrulline
<220> FEATURE:
<221> NAME/KEY: MOD_RES
<222> LOCATION: (7)..(7)
<223> OTHER INFORMATION: D-glutamic acid
<220> FEATURE:
<221> NAME/KEY: MOD_RES
<222> LOCATION: (11)..(11)
<223> OTHER INFORMATION: citrulline
<220> FEATURE:
<221> NAME/KEY: MOD_RES
<222> LOCATION: (13)..(13)
<223> OTHER INFORMATION: c' amidated

<400> SEQUENCE: 42

```
Xaa Xaa Cys Tyr Xaa Lys Xaa Pro Tyr Arg Xaa Cys Arg
1               5                   10
```

<210> SEQ ID NO 43

```
<211> LENGTH: 14
<212> TYPE: PRT
<213> ORGANISM: Artificial
<220> FEATURE:
<223> OTHER INFORMATION: synthetic peptide
<220> FEATURE:
<221> NAME/KEY: MISC_FEATURE
<222> LOCATION: (1)..(1)
<223> OTHER INFORMATION: desaminoTMG-APA (formula IV in the
      specification)
<220> FEATURE:
<221> NAME/KEY: MOD_RES
<222> LOCATION: (3)..(3)
<223> OTHER INFORMATION: 3-((2-naphthyl) alanine
<220> FEATURE:
<221> NAME/KEY: MOD_RES
<222> LOCATION: (6)..(6)
<223> OTHER INFORMATION: citrulline
<220> FEATURE:
<221> NAME/KEY: MOD_RES
<222> LOCATION: (8)..(8)
<223> OTHER INFORMATION: D-glutamic acid
<220> FEATURE:
<221> NAME/KEY: MOD_RES
<222> LOCATION: (12)..(12)
<223> OTHER INFORMATION: citrulline
<220> FEATURE:
<221> NAME/KEY: MOD_RES
<222> LOCATION: (14)..(14)
<223> OTHER INFORMATION: c' amidated

<400> SEQUENCE: 43

Xaa Arg Xaa Cys Tyr Xaa Lys Xaa Pro Tyr Arg Xaa Cys Arg
 1               5                  10

<210> SEQ ID NO 44
<211> LENGTH: 14
<212> TYPE: PRT
<213> ORGANISM: Artificial
<220> FEATURE:
<223> OTHER INFORMATION: synthetic peptide
<220> FEATURE:
<221> NAME/KEY: MISC_FEATURE
<222> LOCATION: (1)..(1)
<223> OTHER INFORMATION: R-CH2 - formula (V) in the specification
<220> FEATURE:
<221> NAME/KEY: MOD_RES
<222> LOCATION: (3)..(3)
<223> OTHER INFORMATION: 3-((2-naphthyl) alanine
<220> FEATURE:
<221> NAME/KEY: MOD_RES
<222> LOCATION: (6)..(6)
<223> OTHER INFORMATION: citrulline
<220> FEATURE:
<221> NAME/KEY: MOD_RES
<222> LOCATION: (8)..(8)
<223> OTHER INFORMATION: D-glutamic acid
<220> FEATURE:
<221> NAME/KEY: MOD_RES
<222> LOCATION: (12)..(12)
<223> OTHER INFORMATION: citrulline
<220> FEATURE:
<221> NAME/KEY: MOD_RES
<222> LOCATION: (14)..(14)
<223> OTHER INFORMATION: c' amidated

<400> SEQUENCE: 44

Xaa Arg Xaa Cys Tyr Xaa Lys Xaa Pro Tyr Arg Xaa Cys Arg
 1               5                  10

<210> SEQ ID NO 45
<211> LENGTH: 13
<212> TYPE: PRT
<213> ORGANISM: Artificial
<220> FEATURE:
```

```
<223> OTHER INFORMATION: synthetic peptide
<220> FEATURE:
<221> NAME/KEY: MOD_RES
<222> LOCATION: (2)..(2)
<223> OTHER INFORMATION: 3-((2-naphthyl) alanine
<220> FEATURE:
<221> NAME/KEY: MOD_RES
<222> LOCATION: (5)..(5)
<223> OTHER INFORMATION: citrulline
<220> FEATURE:
<221> NAME/KEY: MOD_RES
<222> LOCATION: (7)..(7)
<223> OTHER INFORMATION: D-glutamic acid
<220> FEATURE:
<221> NAME/KEY: MOD_RES
<222> LOCATION: (11)..(11)
<223> OTHER INFORMATION: citrulline
<220> FEATURE:
<221> NAME/KEY: MOD_RES
<222> LOCATION: (13)..(13)
<223> OTHER INFORMATION: c' amidated

<400> SEQUENCE: 45

Arg Xaa Cys Tyr Xaa Lys Xaa Pro Tyr Arg Xaa Cys Arg
1               5                   10

<210> SEQ ID NO 46
<211> LENGTH: 14
<212> TYPE: PRT
<213> ORGANISM: Artificial
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: tetramethylguanyl-arginine
<220> FEATURE:
<221> NAME/KEY: MOD_RES
<222> LOCATION: (3)..(3)
<223> OTHER INFORMATION: 3-((2-naphthyl) alanine
<220> FEATURE:
<221> NAME/KEY: MOD_RES
<222> LOCATION: (6)..(6)
<223> OTHER INFORMATION: citrulline
<220> FEATURE:
<221> NAME/KEY: MOD_RES
<222> LOCATION: (8)..(8)
<223> OTHER INFORMATION: D-citrulline
<220> FEATURE:
<221> NAME/KEY: MOD_RES
<222> LOCATION: (12)..(12)
<223> OTHER INFORMATION: citrulline
<220> FEATURE:
<221> NAME/KEY: MOD_RES
<222> LOCATION: (14)..(14)
<223> OTHER INFORMATION: C' AMIDATED

<400> SEQUENCE: 46

Xaa Arg Xaa Cys Tyr Xaa Lys Xaa Pro Tyr Arg Xaa Cys Arg
1               5                   10

<210> SEQ ID NO 47
<211> LENGTH: 14
<212> TYPE: PRT
<213> ORGANISM: Artificial
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: 6-aminohexanoyl-arginine
<220> FEATURE:
<221> NAME/KEY: MOD_RES
<222> LOCATION: (3)..(3)
<223> OTHER INFORMATION: 3-((2-naphthyl) alanine
```

```
<220> FEATURE:
<221> NAME/KEY: MOD_RES
<222> LOCATION: (6)..(6)
<223> OTHER INFORMATION: citrulline
<220> FEATURE:
<221> NAME/KEY: MOD_RES
<222> LOCATION: (8)..(8)
<223> OTHER INFORMATION: D-citrulline
<220> FEATURE:
<221> NAME/KEY: MOD_RES
<222> LOCATION: (12)..(12)
<223> OTHER INFORMATION: citrulline
<220> FEATURE:
<221> NAME/KEY: MOD_RES
<222> LOCATION: (14)..(14)
<223> OTHER INFORMATION: C' AMIDATED

<400> SEQUENCE: 47

Xaa Arg Xaa Cys Tyr Xaa Lys Xaa Pro Tyr Arg Xaa Cys Arg
1               5                   10

<210> SEQ ID NO 48
<211> LENGTH: 14
<212> TYPE: PRT
<213> ORGANISM: Artificial
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: 6-aminohexanoyl-arginine
<220> FEATURE:
<221> NAME/KEY: MOD_RES
<222> LOCATION: (3)..(3)
<223> OTHER INFORMATION: 3-((2-naphthyl) alanine
<220> FEATURE:
<221> NAME/KEY: MOD_RES
<222> LOCATION: (8)..(8)
<223> OTHER INFORMATION: D-lysine
<220> FEATURE:
<221> NAME/KEY: MOD_RES
<222> LOCATION: (12)..(12)
<223> OTHER INFORMATION: citrulline

<400> SEQUENCE: 48

Xaa Arg Xaa Cys Tyr Arg Lys Xaa Pro Tyr Arg Xaa Cys Arg
1               5                   10

<210> SEQ ID NO 49
<211> LENGTH: 14
<212> TYPE: PRT
<213> ORGANISM: Artificial
<220> FEATURE:
<223> OTHER INFORMATION: synthetic peptide
<220> FEATURE:
<221> NAME/KEY: MOD_RES
<222> LOCATION: (3)..(3)
<223> OTHER INFORMATION: 3-((2-naphthyl) alanine
<220> FEATURE:
<221> NAME/KEY: MOD_RES
<222> LOCATION: (6)..(6)
<223> OTHER INFORMATION: citrulline
<220> FEATURE:
<221> NAME/KEY: MOD_RES
<222> LOCATION: (8)..(8)
<223> OTHER INFORMATION: D-lysine
<220> FEATURE:
<221> NAME/KEY: MOD_RES
<222> LOCATION: (12)..(12)
<223> OTHER INFORMATION: citrulline
<220> FEATURE:
<221> NAME/KEY: MOD_RES
<222> LOCATION: (14)..(14)
<223> OTHER INFORMATION: C' amidated
```

```
<400> SEQUENCE: 49

Arg Arg Xaa Cys Tyr Xaa Arg Xaa Pro Tyr Arg Xaa Cys Arg
1               5                   10

<210> SEQ ID NO 50
<211> LENGTH: 14
<212> TYPE: PRT
<213> ORGANISM: Artificial
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: N' ACETYLATED
<220> FEATURE:
<221> NAME/KEY: MOD_RES
<222> LOCATION: (3)..(3)
<223> OTHER INFORMATION: 3-((2-naphthyl) alanine
<220> FEATURE:
<221> NAME/KEY: MOD_RES
<222> LOCATION: (6)..(6)
<223> OTHER INFORMATION: citrulline
<220> FEATURE:
<221> NAME/KEY: MOD_RES
<222> LOCATION: (8)..(8)
<223> OTHER INFORMATION: D-lysine
<220> FEATURE:
<221> NAME/KEY: MOD_RES
<222> LOCATION: (12)..(12)
<223> OTHER INFORMATION: citrulline
<220> FEATURE:
<221> NAME/KEY: MOD_RES
<222> LOCATION: (14)..(14)
<223> OTHER INFORMATION: C' amidated

<400> SEQUENCE: 50

Arg Arg Xaa Cys Tyr Xaa Arg Xaa Pro Tyr Arg Xaa Cys Arg
1               5                   10

<210> SEQ ID NO 51
<211> LENGTH: 14
<212> TYPE: PRT
<213> ORGANISM: Artificial
<220> FEATURE:
<223> OTHER INFORMATION: SYNTHETIC PEPTIDE
<220> FEATURE:
<221> NAME/KEY: MOD_RES
<222> LOCATION: (1)..(1)
<223> OTHER INFORMATION: N' ACETYLATED
<220> FEATURE:
<221> NAME/KEY: MOD_RES
<222> LOCATION: (3)..(3)
<223> OTHER INFORMATION: 3-((2-naphthyl) alanine
<220> FEATURE:
<221> NAME/KEY: MOD_RES
<222> LOCATION: (6)..(6)
<223> OTHER INFORMATION: citrulline
<220> FEATURE:
<221> NAME/KEY: MOD_RES
<222> LOCATION: (8)..(8)
<223> OTHER INFORMATION: D-lysine
<220> FEATURE:
<221> NAME/KEY: MOD_RES
<222> LOCATION: (12)..(12)
<223> OTHER INFORMATION: citrulline
<220> FEATURE:
<221> NAME/KEY: MOD_RES
<222> LOCATION: (14)..(14)
<223> OTHER INFORMATION: C' AMIDATED

<400> SEQUENCE: 51

Arg Arg Xaa Cys Tyr Xaa Lys Xaa Pro Tyr Arg Xaa Cys Arg
1               5                   10
```

```
<210> SEQ ID NO 52
<211> LENGTH: 14
<212> TYPE: PRT
<213> ORGANISM: Artificial
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: N' ACETYLATED
<220> FEATURE:
<221> NAME/KEY: MOD_RES
<222> LOCATION: (3)..(3)
<223> OTHER INFORMATION: 3-((2-naphthyl) alanine
<220> FEATURE:
<221> NAME/KEY: MOD_RES
<222> LOCATION: (8)..(8)
<223> OTHER INFORMATION: D-citrulline
<220> FEATURE:
<221> NAME/KEY: MOD_RES
<222> LOCATION: (12)..(12)
<223> OTHER INFORMATION: citrulline
<220> FEATURE:
<221> NAME/KEY: MOD_RES
<222> LOCATION: (14)..(14)
<223> OTHER INFORMATION: C' AMIDATED

<400> SEQUENCE: 52

Arg Arg Xaa Cys Tyr Arg Lys Xaa Pro Tyr Arg Xaa Cys Arg
1               5                   10

<210> SEQ ID NO 53
<211> LENGTH: 14
<212> TYPE: PRT
<213> ORGANISM: Artificial
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: 4-fluorobenzoyl-arginine
<220> FEATURE:
<221> NAME/KEY: MOD_RES
<222> LOCATION: (3)..(3)
<223> OTHER INFORMATION: 3-((2-naphthyl) alanine
<220> FEATURE:
<221> NAME/KEY: MOD_RES
<222> LOCATION: (6)..(6)
<223> OTHER INFORMATION: citrulline
<220> FEATURE:
<221> NAME/KEY: MOD_RES
<222> LOCATION: (8)..(8)
<223> OTHER INFORMATION: D-glutamic acid
<220> FEATURE:
<221> NAME/KEY: MOD_RES
<222> LOCATION: (12)..(12)
<223> OTHER INFORMATION: citrulline
<220> FEATURE:
<221> NAME/KEY: MISC_FEATURE
<222> LOCATION: (14)..(14)
<223> OTHER INFORMATION: derivatization by a NH-methyl group

<400> SEQUENCE: 53

Xaa Arg Xaa Cys Tyr Xaa Lys Xaa Pro Tyr Arg Xaa Cys Arg
1               5                   10

<210> SEQ ID NO 54
<211> LENGTH: 14
<212> TYPE: PRT
<213> ORGANISM: Artificial
<220> FEATURE:
<223> OTHER INFORMATION: synthetic peptide
<220> FEATURE:
<221> NAME/KEY: MOD_RES
```

```
<222> LOCATION: (1)..(1)
<223> OTHER INFORMATION: 4-fluorobenzoyl-arginine
<220> FEATURE:
<221> NAME/KEY: MOD_RES
<222> LOCATION: (3)..(3)
<223> OTHER INFORMATION: 3-((2-naphthyl) alanine
<220> FEATURE:
<221> NAME/KEY: MOD_RES
<222> LOCATION: (6)..(6)
<223> OTHER INFORMATION: citrulline
<220> FEATURE:
<221> NAME/KEY: MOD_RES
<222> LOCATION: (8)..(8)
<223> OTHER INFORMATION: D-glutamic acid
<220> FEATURE:
<221> NAME/KEY: MOD_RES
<222> LOCATION: (12)..(12)
<223> OTHER INFORMATION: citrulline
<220> FEATURE:
<221> NAME/KEY: MISC_FEATURE
<222> LOCATION: (14)..(14)
<223> OTHER INFORMATION: derivatization by a NH-ethyl group

<400> SEQUENCE: 54

Xaa Arg Xaa Cys Tyr Xaa Lys Xaa Pro Tyr Arg Xaa Cys Arg
1               5                   10

<210> SEQ ID NO 55
<211> LENGTH: 14
<212> TYPE: PRT
<213> ORGANISM: Artificial
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: 4-fluorobenzoyl-arginine
<220> FEATURE:
<221> NAME/KEY: MOD_RES
<222> LOCATION: (3)..(3)
<223> OTHER INFORMATION: 3-((2-naphthyl) alanine
<220> FEATURE:
<221> NAME/KEY: MOD_RES
<222> LOCATION: (6)..(6)
<223> OTHER INFORMATION: citrulline
<220> FEATURE:
<221> NAME/KEY: MOD_RES
<222> LOCATION: (8)..(8)
<223> OTHER INFORMATION: D-glutamic acid
<220> FEATURE:
<221> NAME/KEY: MOD_RES
<222> LOCATION: (12)..(12)
<223> OTHER INFORMATION: citrulline
<220> FEATURE:
<221> NAME/KEY: MISC_FEATURE
<222> LOCATION: (14)..(14)
<223> OTHER INFORMATION: derivatization by NH-isopropyl

<400> SEQUENCE: 55

Xaa Arg Xaa Cys Tyr Xaa Lys Xaa Pro Tyr Arg Xaa Cys Arg
1               5                   10

<210> SEQ ID NO 56
<211> LENGTH: 14
<212> TYPE: PRT
<213> ORGANISM: Artificial
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: 4-fluorobenzoyl-arginine
<220> FEATURE:
<221> NAME/KEY: MOD_RES
<222> LOCATION: (3)..(3)
```

```
<223> OTHER INFORMATION: 3-((2-naphthyl) alanine
<220> FEATURE:
<221> NAME/KEY: MOD_RES
<222> LOCATION: (6)..(6)
<223> OTHER INFORMATION: citrulline
<220> FEATURE:
<221> NAME/KEY: MOD_RES
<222> LOCATION: (8)..(8)
<223> OTHER INFORMATION: D-glutamic acid
<220> FEATURE:
<221> NAME/KEY: MOD_RES
<222> LOCATION: (12)..(12)
<223> OTHER INFORMATION: citrulline
<220> FEATURE:
<221> NAME/KEY: MISC_FEATURE
<222> LOCATION: (14)..(14)
<223> OTHER INFORMATION: derivatization with a tyramine residue

<400> SEQUENCE: 56

Xaa Arg Xaa Cys Tyr Xaa Lys Xaa Pro Tyr Arg Xaa Cys Arg
1               5                   10

<210> SEQ ID NO 57
<211> LENGTH: 14
<212> TYPE: PRT
<213> ORGANISM: Artificial
<220> FEATURE:
<223> OTHER INFORMATION: synthetic peptide
<220> FEATURE:
<221> NAME/KEY: MOD_RES
<222> LOCATION: (3)..(3)
<223> OTHER INFORMATION: 3-((2-naphthyl) alanine
<220> FEATURE:
<221> NAME/KEY: MOD_RES
<222> LOCATION: (8)..(8)
<223> OTHER INFORMATION: D-lysine
<220> FEATURE:
<221> NAME/KEY: MOD_RES
<222> LOCATION: (12)..(12)
<223> OTHER INFORMATION: citrulline

<400> SEQUENCE: 57

Ala Arg Xaa Cys Tyr Arg Lys Xaa Pro Tyr Arg Xaa Cys Arg
1               5                   10

<210> SEQ ID NO 58
<211> LENGTH: 14
<212> TYPE: PRT
<213> ORGANISM: Artificial
<220> FEATURE:
<223> OTHER INFORMATION: synthetic peptide
<220> FEATURE:
<221> NAME/KEY: MOD_RES
<222> LOCATION: (3)..(3)
<223> OTHER INFORMATION: 3-((2-naphthyl) alanine
<220> FEATURE:
<221> NAME/KEY: MOD_RES
<222> LOCATION: (8)..(8)
<223> OTHER INFORMATION: D-lysine
<220> FEATURE:
<221> NAME/KEY: MOD_RES
<222> LOCATION: (12)..(12)
<223> OTHER INFORMATION: citrulline

<400> SEQUENCE: 58

Arg Arg Xaa Cys Tyr Ala Lys Xaa Pro Tyr Arg Xaa Cys Arg
1               5                   10

<210> SEQ ID NO 59
<211> LENGTH: 14
<212> TYPE: PRT
<213> ORGANISM: Artificial
<220> FEATURE:
```

```
<223> OTHER INFORMATION: synthetic peptide
<220> FEATURE:
<221> NAME/KEY: MOD_RES
<222> LOCATION: (3)..(3)
<223> OTHER INFORMATION: 3-((2-naphthyl) alanine
<220> FEATURE:
<221> NAME/KEY: MOD_RES
<222> LOCATION: (8)..(8)
<223> OTHER INFORMATION: D-lysine
<220> FEATURE:
<221> NAME/KEY: MOD_RES
<222> LOCATION: (12)..(12)
<223> OTHER INFORMATION: citrulline

<400> SEQUENCE: 59

Arg Arg Xaa Cys Tyr Arg Ala Xaa Pro Tyr Arg Xaa Cys Arg
1               5                   10

<210> SEQ ID NO 60
<211> LENGTH: 14
<212> TYPE: PRT
<213> ORGANISM: Artificial
<220> FEATURE:
<223> OTHER INFORMATION: synthetic peptide
<220> FEATURE:
<221> NAME/KEY: MOD_RES
<222> LOCATION: (3)..(3)
<223> OTHER INFORMATION: 3-((2-naphthyl) alanine
<220> FEATURE:
<221> NAME/KEY: MOD_RES
<222> LOCATION: (8)..(8)
<223> OTHER INFORMATION: D-alanine
<220> FEATURE:
<221> NAME/KEY: MOD_RES
<222> LOCATION: (12)..(12)
<223> OTHER INFORMATION: citrulline

<400> SEQUENCE: 60

Arg Arg Xaa Cys Tyr Arg Lys Xaa Pro Tyr Arg Xaa Cys Arg
1               5                   10

<210> SEQ ID NO 61
<211> LENGTH: 14
<212> TYPE: PRT
<213> ORGANISM: Artificial
<220> FEATURE:
<223> OTHER INFORMATION: synthetic peptide
<220> FEATURE:
<221> NAME/KEY: MOD_RES
<222> LOCATION: (3)..(3)
<223> OTHER INFORMATION: 3-((2-naphthyl) alanine
<220> FEATURE:
<221> NAME/KEY: MOD_RES
<222> LOCATION: (8)..(8)
<223> OTHER INFORMATION: D-lysine
<220> FEATURE:
<221> NAME/KEY: MOD_RES
<222> LOCATION: (12)..(12)
<223> OTHER INFORMATION: citrulline

<400> SEQUENCE: 61

Arg Arg Xaa Cys Tyr Arg Lys Xaa Ala Tyr Arg Xaa Cys Arg
1               5                   10

<210> SEQ ID NO 62
<211> LENGTH: 14
<212> TYPE: PRT
<213> ORGANISM: Artificial
<220> FEATURE:
<223> OTHER INFORMATION: synthetic peptide
<220> FEATURE:
<221> NAME/KEY: MOD_RES
<222> LOCATION: (3)..(3)
```

```
<223> OTHER INFORMATION: 3-((2-naphthyl) alanine
<220> FEATURE:
<221> NAME/KEY: MOD_RES
<222> LOCATION: (8)..(8)
<223> OTHER INFORMATION: D-lysine
<220> FEATURE:
<221> NAME/KEY: MOD_RES
<222> LOCATION: (12)..(12)
<223> OTHER INFORMATION: citrulline

<400> SEQUENCE: 62

Arg Arg Xaa Cys Tyr Arg Lys Xaa Pro Ala Arg Xaa Cys Arg
1               5                   10

<210> SEQ ID NO 63
<211> LENGTH: 14
<212> TYPE: PRT
<213> ORGANISM: Artificial
<220> FEATURE:
<223> OTHER INFORMATION: synthetic peptide
<220> FEATURE:
<221> NAME/KEY: MOD_RES
<222> LOCATION: (3)..(3)
<223> OTHER INFORMATION: 3-((2-naphthyl) alanine
<220> FEATURE:
<221> NAME/KEY: MOD_RES
<222> LOCATION: (8)..(8)
<223> OTHER INFORMATION: D-lysine
<220> FEATURE:
<221> NAME/KEY: MOD_RES
<222> LOCATION: (12)..(12)
<223> OTHER INFORMATION: citrulline

<400> SEQUENCE: 63

Arg Arg Xaa Cys Tyr Arg Lys Xaa Pro Tyr Ala Xaa Cys Arg
1               5                   10

<210> SEQ ID NO 64
<211> LENGTH: 14
<212> TYPE: PRT
<213> ORGANISM: Artificial
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: citrulline
<220> FEATURE:
<221> NAME/KEY: MOD_RES
<222> LOCATION: (3)..(3)
<223> OTHER INFORMATION: 3-((2-naphthyl) alanine
<220> FEATURE:
<221> NAME/KEY: MOD_RES
<222> LOCATION: (8)..(8)
<223> OTHER INFORMATION: D-lysine
<220> FEATURE:
<221> NAME/KEY: MOD_RES
<222> LOCATION: (12)..(12)
<223> OTHER INFORMATION: citrulline

<400> SEQUENCE: 64

Xaa Arg Xaa Cys Tyr Arg Lys Xaa Pro Tyr Arg Xaa Cys Arg
1               5                   10

<210> SEQ ID NO 65
<211> LENGTH: 14
<212> TYPE: PRT
<213> ORGANISM: Artificial
<220> FEATURE:
<223> OTHER INFORMATION: synthetic peptide
<220> FEATURE:
<221> NAME/KEY: MOD_RES
<222> LOCATION: (3)..(3)
```

```
<223> OTHER INFORMATION: 3-((2-naphthyl) alanine
<220> FEATURE:
<221> NAME/KEY: MOD_RES
<222> LOCATION: (6)..(6)
<223> OTHER INFORMATION: citrulline
<220> FEATURE:
<221> NAME/KEY: MOD_RES
<222> LOCATION: (8)..(8)
<223> OTHER INFORMATION: D-lysine
<220> FEATURE:
<221> NAME/KEY: MOD_RES
<222> LOCATION: (12)..(12)
<223> OTHER INFORMATION: citrulline

<400> SEQUENCE: 65

Arg Arg Xaa Cys Tyr Xaa Lys Xaa Pro Tyr Arg Xaa Cys Arg
1               5                   10

<210> SEQ ID NO 66
<211> LENGTH: 14
<212> TYPE: PRT
<213> ORGANISM: Artificial
<220> FEATURE:
<223> OTHER INFORMATION: synthetic peptide
<220> FEATURE:
<221> NAME/KEY: MOD_RES
<222> LOCATION: (3)..(3)
<223> OTHER INFORMATION: 3-((2-naphthyl) alanine
<220> FEATURE:
<221> NAME/KEY: MOD_RES
<222> LOCATION: (6)..(6)
<223> OTHER INFORMATION: citrulline
<220> FEATURE:
<221> NAME/KEY: MOD_RES
<222> LOCATION: (8)..(8)
<223> OTHER INFORMATION: D-lysine
<220> FEATURE:
<221> NAME/KEY: MOD_RES
<222> LOCATION: (12)..(12)
<223> OTHER INFORMATION: citrulline
<220> FEATURE:
<221> NAME/KEY: MOD_RES
<222> LOCATION: (14)..(14)
<223> OTHER INFORMATION: C' AMIDATED

<400> SEQUENCE: 66

Arg Arg Xaa Cys Tyr Xaa Lys Xaa Pro Tyr Arg Xaa Cys Arg
1               5                   10

<210> SEQ ID NO 67
<211> LENGTH: 14
<212> TYPE: PRT
<213> ORGANISM: Artificial
<220> FEATURE:
<223> OTHER INFORMATION: synthetic peptide
<220> FEATURE:
<221> NAME/KEY: MOD_RES
<222> LOCATION: (3)..(3)
<223> OTHER INFORMATION: 3-((2-naphthyl) alanine
<220> FEATURE:
<221> NAME/KEY: MOD_RES
<222> LOCATION: (7)..(7)
<223> OTHER INFORMATION: citrulline
<220> FEATURE:
<221> NAME/KEY: MOD_RES
<222> LOCATION: (8)..(8)
<223> OTHER INFORMATION: D-lysine
<220> FEATURE:
<221> NAME/KEY: MOD_RES
<222> LOCATION: (12)..(12)
<223> OTHER INFORMATION: citrulline

<400> SEQUENCE: 67

Arg Arg Xaa Cys Tyr Arg Xaa Xaa Pro Tyr Arg Xaa Cys Arg
```

```
<210> SEQ ID NO 68
<211> LENGTH: 14
<212> TYPE: PRT
<213> ORGANISM: Artificial
<220> FEATURE:
<223> OTHER INFORMATION: synthetic peptide
<220> FEATURE:
<221> NAME/KEY: MOD_RES
<222> LOCATION: (3)..(3)
<223> OTHER INFORMATION: 3-((2-naphthyl) alanine
<220> FEATURE:
<221> NAME/KEY: MOD_RES
<222> LOCATION: (6)..(6)
<223> OTHER INFORMATION: citrulline
<220> FEATURE:
<221> NAME/KEY: MOD_RES
<222> LOCATION: (8)..(8)
<223> OTHER INFORMATION: D-citrulline
<220> FEATURE:
<221> NAME/KEY: MOD_RES
<222> LOCATION: (12)..(12)
<223> OTHER INFORMATION: citrulline
<220> FEATURE:
<221> NAME/KEY: MOD_RES
<222> LOCATION: (14)..(14)
<223> OTHER INFORMATION: C' AMIDATED

<400> SEQUENCE: 68

Arg Arg Xaa Cys Tyr Xaa Lys Xaa Pro Tyr Arg Xaa Cys Arg
1               5                   10

<210> SEQ ID NO 69
<211> LENGTH: 14
<212> TYPE: PRT
<213> ORGANISM: Artificial
<220> FEATURE:
<223> OTHER INFORMATION: synthetic peptide designed based on tachyplesin
      family polypeptide of horseshoe crab
<220> FEATURE:
<221> NAME/KEY: MOD_RES
<222> LOCATION: (3)..(3)
<223> OTHER INFORMATION: 3-((2-naphthyl) alanine
<220> FEATURE:
<221> NAME/KEY: MOD_RES
<222> LOCATION: (8)..(8)
<223> OTHER INFORMATION: D-lysine
<220> FEATURE:
<221> NAME/KEY: MOD_RES
<222> LOCATION: (12)..(12)
<223> OTHER INFORMATION: citrulline

<400> SEQUENCE: 69

Arg Arg Xaa Cys Tyr Arg Lys Xaa Pro Tyr Arg Xaa Cys Arg
1               5                   10

<210> SEQ ID NO 70
<211> LENGTH: 14
<212> TYPE: PRT
<213> ORGANISM: Artificial
<220> FEATURE:
<223> OTHER INFORMATION: synthetic peptide
<220> FEATURE:
<221> NAME/KEY: MOD_RES
<222> LOCATION: (3)..(3)
<223> OTHER INFORMATION: 3-((2-naphthyl) alanine
<220> FEATURE:
<221> NAME/KEY: MOD_RES
<222> LOCATION: (6)..(6)
<223> OTHER INFORMATION: citrulline
<220> FEATURE:
<221> NAME/KEY: MOD_RES
<222> LOCATION: (8)..(8)
```

```
<223> OTHER INFORMATION: D-citrulline
<220> FEATURE:
<221> NAME/KEY: MOD_RES
<222> LOCATION: (12)..(12)
<223> OTHER INFORMATION: citrulline

<400> SEQUENCE: 70

Arg Arg Xaa Cys Tyr Xaa Lys Xaa Pro Tyr Arg Xaa Cys Arg
1               5                   10

<210> SEQ ID NO 71
<211> LENGTH: 14
<212> TYPE: PRT
<213> ORGANISM: Artificial
<220> FEATURE:
<223> OTHER INFORMATION: synthetic peptide
<220> FEATURE:
<221> NAME/KEY: MOD_RES
<222> LOCATION: (3)..(3)
<223> OTHER INFORMATION: 3-((2-naphthyl) alanine
<220> FEATURE:
<221> NAME/KEY: MOD_RES
<222> LOCATION: (8)..(8)
<223> OTHER INFORMATION: D-citrulline
<220> FEATURE:
<221> NAME/KEY: MOD_RES
<222> LOCATION: (12)..(12)
<223> OTHER INFORMATION: citrulline

<400> SEQUENCE: 71

Arg Arg Xaa Cys Tyr Arg Lys Xaa Pro Tyr Arg Xaa Cys Arg
1               5                   10

<210> SEQ ID NO 72
<211> LENGTH: 14
<212> TYPE: PRT
<213> ORGANISM: Artificial
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: citrulline
<220> FEATURE:
<221> NAME/KEY: MOD_RES
<222> LOCATION: (3)..(3)
<223> OTHER INFORMATION: 3-((2-naphthyl) alanine
<220> FEATURE:
<221> NAME/KEY: MOD_RES
<222> LOCATION: (8)..(8)
<223> OTHER INFORMATION: D-citrulline
<220> FEATURE:
<221> NAME/KEY: MOD_RES
<222> LOCATION: (12)..(12)
<223> OTHER INFORMATION: citrulline
<220> FEATURE:
<221> NAME/KEY: MOD_RES
<222> LOCATION: (14)..(14)
<223> OTHER INFORMATION: C' Amidated

<400> SEQUENCE: 72

Xaa Arg Xaa Cys Tyr Arg Lys Xaa Pro Tyr Arg Xaa Cys Arg
1               5                   10

<210> SEQ ID NO 73
<211> LENGTH: 14
<212> TYPE: PRT
<213> ORGANISM: Artificial
<220> FEATURE:
<223> OTHER INFORMATION: Synthetic peptide according to Formula I
<220> FEATURE:
<221> NAME/KEY: MISC_FEATURE
<222> LOCATION: (1)..(1)
```

```
<223> OTHER INFORMATION: Xaa is Arg, Lys, ornithine, citrulline, Ala or
      Glu or is absent
<220> FEATURE:
<221> NAME/KEY: MISC_FEATURE
<222> LOCATION: (1)..(14)
<223> OTHER INFORMATION: L-amino acid or D-amino acid
<220> FEATURE:
<221> NAME/KEY: MISC_FEATURE
<222> LOCATION: (2)..(2)
<223> OTHER INFORMATION: Xaa is Arg or Glu
<220> FEATURE:
<221> NAME/KEY: MISC_FEATURE
<222> LOCATION: (3)..(3)
<223> OTHER INFORMATION: Xaa is an aromatic amino acid residue
<220> FEATURE:
<221> NAME/KEY: DISULFID
<222> LOCATION: (4)..(13)
<223> OTHER INFORMATION: Cys at 4-position and Cys at 13-position may
      form a disulfid bond.
<220> FEATURE:
<221> NAME/KEY: MISC_FEATURE
<222> LOCATION: (6)..(6)
<223> OTHER INFORMATION: Xaa is Arg, Lys, ornithine, citrulline, Ala or
      Glu.
<220> FEATURE:
<221> NAME/KEY: MISC_FEATURE
<222> LOCATION: (7)..(7)
<223> OTHER INFORMATION: Xaa is Arg, Lys, ornithine, citrulline, Ala or
      Glu.
<220> FEATURE:
<221> NAME/KEY: MISC_FEATURE
<222> LOCATION: (8)..(8)
<223> OTHER INFORMATION: Xaa is Pro, Gly, ornithine, Lys, Ala,
      citrulline, Arg or Glu.
<220> FEATURE:
<221> NAME/KEY: MISC_FEATURE
<222> LOCATION: (9)..(9)
<223> OTHER INFORMATION: Xaa is Pro, Gly, ornithine, Lys, Ala,
      citrulline or Arg
<220> FEATURE:
<221> NAME/KEY: MISC_FEATURE
<222> LOCATION: (10)..(10)
<223> OTHER INFORMATION: Xaa is Tyr, Phe, Ala, naphthyl Ala, citrulline
      or Glu.
<220> FEATURE:
<221> NAME/KEY: MISC_FEATURE
<222> LOCATION: (11)..(11)
<223> OTHER INFORMATION: Xaa is Arg, Lys, ornithine, citrulline, Ala or
      Glu.
<220> FEATURE:
<221> NAME/KEY: MISC_FEATURE
<222> LOCATION: (12)..(12)
<223> OTHER INFORMATION: Xaa is Arg, Lys, citrulline or Glu.
<220> FEATURE:
<221> NAME/KEY: MISC_FEATURE
<222> LOCATION: (14)..(14)
<223> OTHER INFORMATION: Xaa is Arg, Glu, Lys or citrulline

<400> SEQUENCE: 73

Xaa Xaa Xaa Cys Tyr Xaa Xaa Xaa Xaa Xaa Xaa Xaa Cys Xaa
1               5                   10

<210> SEQ ID NO 74
<211> LENGTH: 14
<212> TYPE: PRT
<213> ORGANISM: Artificial
<220> FEATURE:
<223> OTHER INFORMATION: Synthetic peptide according to Formula II
<220> FEATURE:
<221> NAME/KEY: MISC_FEATURE
<222> LOCATION: (1)..(1)
<223> OTHER INFORMATION: Xaa is Arg, Ala or Citrulline
<220> FEATURE:
<221> NAME/KEY: MISC_FEATURE
<222> LOCATION: (3)..(3)
<223> OTHER INFORMATION: Xaa is Trp or naphtylalanine
<220> FEATURE:
```

```
<221> NAME/KEY: MISC_FEATURE
<222> LOCATION: (6)..(6)
<223> OTHER INFORMATION: Xaa is Arg, Ala or Citrulline
<220> FEATURE:
<221> NAME/KEY: MISC_FEATURE
<222> LOCATION: (7)..(7)
<223> OTHER INFORMATION: Xaa is Lys, Ala or Citrulline
<220> FEATURE:
<221> NAME/KEY: MISC_FEATURE
<222> LOCATION: (8)..(9)
<223> OTHER INFORMATION: These positions represent a dipeptide selected
      from: D-lysyl-proline, D-alanyl-proline, D-lysyl-alanine and
      D-citrullyl-proline
<220> FEATURE:
<221> NAME/KEY: MISC_FEATURE
<222> LOCATION: (10)..(10)
<223> OTHER INFORMATION: Xaa is Tyr or Ala
<220> FEATURE:
<221> NAME/KEY: MISC_FEATURE
<222> LOCATION: (11)..(11)
<223> OTHER INFORMATION: Xaa is Arg, Ala or Citrulline
<220> FEATURE:
<221> NAME/KEY: MISC_FEATURE
<222> LOCATION: (12)..(12)
<223> OTHER INFORMATION: Xaa is Citrulline

<400> SEQUENCE: 74

Xaa Arg Xaa Cys Tyr Xaa Xaa Xaa Xaa Xaa Xaa Xaa Cys Arg
1               5                   10

<210> SEQ ID NO 75
<211> LENGTH: 13
<212> TYPE: PRT
<213> ORGANISM: Artificial
<220> FEATURE:
<223> OTHER INFORMATION: Synthetic peptide according to Formula II
<220> FEATURE:
<221> NAME/KEY: MISC_FEATURE
<222> LOCATION: (1)..(1)
<223> OTHER INFORMATION: Arg, Lys, Ala, ornithine, citrulline or is
      absent
<220> FEATURE:
<221> NAME/KEY: MISC_FEATURE
<222> LOCATION: (3)..(3)
<223> OTHER INFORMATION: Any aromatic amino acid
<220> FEATURE:
<221> NAME/KEY: MISC_FEATURE
<222> LOCATION: (6)..(7)
<223> OTHER INFORMATION: Each position independently represents Arg,
      Lys, Ala, ornithine or citrulline
<220> FEATURE:
<221> NAME/KEY: MISC_FEATURE
<222> LOCATION: (8)..(8)
<223> OTHER INFORMATION: D-citrulline, D-alanine, citrulline or alanine
<220> FEATURE:
<221> NAME/KEY: MISC_FEATURE
<222> LOCATION: (9)..(9)
<223> OTHER INFORMATION: Tyr, Phe, Ala, naphthylalanine or citrulline
<220> FEATURE:
<221> NAME/KEY: MISC_FEATURE
<222> LOCATION: (10)..(10)
<223> OTHER INFORMATION: Arg, Lys, Ala, ornithine or citrulline
<220> FEATURE:
<221> NAME/KEY: MISC_FEATURE
<222> LOCATION: (11)..(11)
<223> OTHER INFORMATION: citrulline
<220> FEATURE:
<221> NAME/KEY: MISC_FEATURE
<222> LOCATION: (13)..(13)
<223> OTHER INFORMATION: Lys or Arg

<400> SEQUENCE: 75

Xaa Arg Xaa Cys Tyr Xaa Xaa Xaa Xaa Xaa Xaa Cys Xaa
1               5                   10
```

```
<210> SEQ ID NO 76
<211> LENGTH: 14
<212> TYPE: PRT
<213> ORGANISM: Artificial
<220> FEATURE:
<223> OTHER INFORMATION: Synthetic peptide according to Formula II
<220> FEATURE:
<221> NAME/KEY: MISC_FEATURE
<222> LOCATION: (1)..(1)
<223> OTHER INFORMATION: Arg, Lys, Ala, ornithine, citrulline or is
      absent
<220> FEATURE:
<221> NAME/KEY: MISC_FEATURE
<222> LOCATION: (1)..(14)
<223> OTHER INFORMATION: this sequence is structured with the proviso
      that either of the amino acid residues at positions 1, 6, 7, 10,
      11 and 14 is Ala or citrulline
<220> FEATURE:
<221> NAME/KEY: MISC_FEATURE
<222> LOCATION: (3)..(3)
<223> OTHER INFORMATION: Any aromatic amino acid
<220> FEATURE:
<221> NAME/KEY: DISULFID
<222> LOCATION: (4)..(13)
<223> OTHER INFORMATION: Cys at 4-position and Cys at 13-position may
      form a disulfid bond.
<220> FEATURE:
<221> NAME/KEY: MISC_FEATURE
<222> LOCATION: (6)..(7)
<223> OTHER INFORMATION: Each position independently represents Arg,
      Lys, Ala, ornithine or citrulline
<220> FEATURE:
<221> NAME/KEY: MISC_FEATURE
<222> LOCATION: (8)..(9)
<223> OTHER INFORMATION: D-orn-pro, pro-D-orn, D-lys-pro, pro-D-lys,
      D-arg-pro, pro-D-arg, D-cit-pro, D-cit-ala, D-ala-cit, pro-D-cit,
      gly-orn, orn-gly, gly-lys, lys-gly, gly-arg, arg-gly, gly-cit,
      cit-gly, D-ala-pro or D-lys-ala
<220> FEATURE:
<221> NAME/KEY: MISC_FEATURE
<222> LOCATION: (10)..(10)
<223> OTHER INFORMATION: Tyr, Phe, Ala, naphthylalanine or citrulline
<220> FEATURE:
<221> NAME/KEY: MISC_FEATURE
<222> LOCATION: (11)..(11)
<223> OTHER INFORMATION: Arg, Lys, Ala, ornithine or citrulline
<220> FEATURE:
<221> NAME/KEY: MISC_FEATURE
<222> LOCATION: (14)..(14)
<223> OTHER INFORMATION: Lys or Arg

<400> SEQUENCE: 76

Xaa Arg Xaa Cys Tyr Xaa Xaa Xaa Xaa Xaa Xaa Xaa Cys Xaa
1               5                   10

<210> SEQ ID NO 77
<211> LENGTH: 18
<212> TYPE: PRT
<213> ORGANISM: Artificial
<220> FEATURE:
<223> OTHER INFORMATION: Synthetic peptide according to Formula II
<220> FEATURE:
<221> NAME/KEY: MISC_FEATURE
<222> LOCATION: (1)..(1)
<223> OTHER INFORMATION: Arg, Lys, Ala, ornithine, citrulline or is
      absent
<220> FEATURE:
<221> NAME/KEY: MISC_FEATURE
<222> LOCATION: (1)..(18)
<223> OTHER INFORMATION: this sequence is structured with the proviso
      that either of the amino acid residues at positions 1, 6, 7, 14,
      15 and 18 is Ala or citrulline
<220> FEATURE:
<221> NAME/KEY: MISC_FEATURE
<222> LOCATION: (3)..(3)
<223> OTHER INFORMATION: Any aromatic amino acid
<220> FEATURE:
```

```
<221> NAME/KEY: DISULFID
<222> LOCATION: (4)..(17)
<223> OTHER INFORMATION: Cys at 4-position and Cys at 17-position may
      form a disulfid bond.
<220> FEATURE:
<221> NAME/KEY: MISC_FEATURE
<222> LOCATION: (6)..(7)
<223> OTHER INFORMATION: Each position independently represents Arg,
      Lys, Ala, ornithine or citrulline
<220> FEATURE:
<221> NAME/KEY: MISC_FEATURE
<222> LOCATION: (8)..(8)
<223> OTHER INFORMATION: Ala, Val, Leu, Ile, Ser, Cys or Met
<220> FEATURE:
<221> NAME/KEY: DISULFID
<222> LOCATION: (8)..(13)
<223> OTHER INFORMATION: when positions 8 and 13 are Cys, they may form
      a disulfide bond
<220> FEATURE:
<221> NAME/KEY: MISC_FEATURE
<222> LOCATION: (9)..(9)
<223> OTHER INFORMATION: Any aromatic amino acid
<220> FEATURE:
<221> NAME/KEY: MISC_FEATURE
<222> LOCATION: (10)..(10)
<223> OTHER INFORMATION: Arg, Lys, Ala, ornithine or citrulline
<220> FEATURE:
<221> NAME/KEY: MISC_FEATURE
<222> LOCATION: (12)..(12)
<223> OTHER INFORMATION: Tyr, Phe, Trp, Ala, Val, Leu, Ile, Ser, Cys or
      Met
<220> FEATURE:
<221> NAME/KEY: MISC_FEATURE
<222> LOCATION: (13)..(13)
<223> OTHER INFORMATION: Ala, Val, Leu, Ile, Ser, Cys or Met

<400> SEQUENCE: 77

Xaa Arg Xaa Cys Tyr Xaa Xaa Xaa Xaa Xaa Gly Xaa Xaa Xaa Xaa Xaa
1               5                   10                  15

Cys Xaa
```

PEPTIDE THERAPY FOR INCREASING PLATELET LEVELS

RELATED APPLICATIONS

This application is a National Phase of PCT Patent Application No. PCT/IL2010/000466 having International filing date of Jun. 13, 2010, which claims the benefit of priority of U.S. Provisional Patent Application No. 61/186,857 filed on Jun. 14, 2009. The contents of the above applications are all incorporated herein by reference.

FIELD OF THE INVENTION

The present invention is directed to compositions and methods for modulating blood platelet levels.

BACKGROUND OF THE INVENTION

Platelets, also referred to as thrombocytes, are anuclear cell fragments that exist in mammalian blood and mediate blood clot formation and haemostasis. In addition, platelets release growth factors that play a significant role in the repair and regeneration of connective tissues and facilitate wound healing. Platelets are the terminal differentiation product of megakaryocytes (MK), which in turn originate from pluripotent stem cells of the bone marrow. While humoral factors such as thrombopoietin (TPO) were found to influence different cellular steps in megakaryocyte development, the complex maturation, differentiation and localization processes that begin with pluripotent stem cells and end with blood platelets remain incompletely understood.

Platelets have an average lifespan of about 5 to 10 days, and their physiological blood level is normally 150,000 to 450,000/µL. When a patient's levels of circulating platelets are depleted below the physiological range, a condition known as thrombocytopenia can follow. This condition is typically associated with defective formation of haemostatic plugs and bleeding, wherein the risk of bleeding is inversely proportional to the platelet count.

Platelet levels may be lowered by the reduction of platelet productivity in bone marrow, or by platelet consumption, promotion of platelet degradation in periphery, or abnormal platelet distribution. For example, thrombocytopenia can be due to antibody mediated platelet destruction or bone marrow failure from e.g. malignant infiltration or chemotherapy.

Pharmacological intervention is possible in some cases; for example, in certain conditions such as immune mediated thrombocytopenia (wherein the platelets are targeted and destroyed by components of the immune system), the use of immunosuppressant drugs is indicated. However, the only presently approved treatment options for many patients are platelet transfusions and bone marrow transplantation. Prophylactic transfusions are used sparingly because they may lose their effectiveness with repeated use due to the development of platelet alloantibodies. Additional potential risks of platelet transfusion include infection, anaphylaxis, and hemolytic reactions. In platelet dysfunction or thrombocytopenia caused by decreased production, transfusions are reserved for patients with active bleeding or severe thrombocytopenia (e.g., platelet count <10,000/µL). In thrombocytopenia caused by platelet destruction, transfusions are reserved for life-threatening or CNS bleeding.

Since TPO has been shown to promote MK proliferation and maturation and platelet formation (Kaushansky et al., 1994), the use of TPO in the treatment of thrombocytopenia has been suggested. It was reported that when administered intravenously to normal healthy volunteers and cancer patients, recombinant human TPO produced a dose-dependent increase in platelet counts beginning 5 days after administration and peaking 10-14 days later. However, clinical testing of early thrombopoietin analogues was stopped because antibodies cross-reacted with endogenous thrombopoietin and caused secondary thrombocytopenia and bleeding (Junzhi et al., 2001). Under certain conditions, TPO is suggested as maintenance therapy rather than for inducing remission.

Other cytokines such as IL-1, IL-3, IL-6 and GM-CSF have been shown to play a role in the generation of megakaryocytes in animals and have demonstrated thrombopoietic activity in clinical studies. However, each either exhibits unacceptable toxicity profiles or does not produce significant increases in platelet counts, and further therapeutic use of these cytokines in the treatment of thrombocytopenia has been discontinued.

It is therefore clear that an unmet need for effective agents as an alternative to platelet transfusions that prevent and/or treat thrombocytopenia exists.

The chemokine receptor CXCR4 is a G-protein coupled receptor that is expressed in a wide assortment of normal tissues, and plays a fundamental role in fetal development, mobilization of hematopoietic stem cells and trafficking of naive lymphocytes (Rossi and Zlotnik, 2000). The chemokine CXCL12 (also known as stromal-derived factor-1, or SDF-1) is CXCR4's only natural ligand. CXCL12 is expressed constitutively in a variety of tissues, including lung, liver, bone marrow and lymph nodes.

Binding of CXCL12 to CXCR4 activates a variety of intracellular signal transduction pathways and effector molecules that regulate cell chemotaxis, adhesion, survival, and proliferation. For example, the phosphatidyl-inositol-3-kinase pathway and the mitogen-activated protein (MAP) kinase pathways are regulated by CXCL12 and CXCR4.

It has been shown that mature MKs functionally express the SDF-1 receptor, CXCR4. It was also found that SDF-1 induced the migration of mature MKs through endothelial cell layers in vitro and increased their platelet production. In addition, adeno-SDF-1 injection into normal mice resulted in increased platelet counts after 3 days, which peaked at days 7 to 10 and returned to normal by day 28 (Lane et al., 2000).

Various uses of chemokine receptor modulators, including CXCR4 agonists and antagonists, have been described in the art (Princen et al., 2005; Tamamura et al., 2005; U.S. Pat. No. 7,169,750). U.S. Pat. No. 7,435,718 discloses certain SDF-1 analog peptides that act as CXCR4 antagonists, and which may be used to treat hematopoietic cells, such as progenitor or stem cells, to promote the rate of cellular multiplication, self-renewal, proliferation or expansion. The disclosure of U.S. Pat. No. 7,435,718 suggests that these SDF-1 analogs may be formulated or administered with additional active ingredients, inter alia TPO.

US Pub. No. 2007/0167459 discloses heterocyclic compounds having CXCR4 regulating activity, in particular CXCR4 antagonists. These compounds are suggested for the prevention and treatment of various diseases, inter alia a cancerous disease including thrombocytopenia. The specification also discloses the use of these compounds with additional drugs or compounds selected from a broad list including TPO.

The bicyclam drug termed AMD3100, originally discovered as an anti-HIV compound, specifically interacts with CXCR4 in an antagonistic manner. Blocking CXCR4 receptor with AMD3100 results in the mobilization of hematopoietic progenitor cells. PCT Pub. No. WO 03/011277 is directed to a method to enhance the population of progenitor and/or stem cells in a subject by administering CXCR4 antagonists such as AMD3100, optionally with co-administered TPO. AMD3100 is undergoing clinical trials to evaluate its ability to increase stem cells available for transplant and is indicated (under the trade name Mozobil) in combination with granulocyte-colony stimulating factor (G-CSF) to mobilize hematopoietic stem cells (HSC) to the peripheral blood for collection and subsequent autologous hematopoietic stem cell transplantation in patients with non-Hodgkin's lymphoma and multiple myeloma. However, as can be determined from the product insert of Mozobil, administration of this drug may result in reduced platelet levels and thrombocytopenia, and accordingly platelet levels must be monitored during Mozobil use and apheresis.

Thus, conflicting evidence exist as to the possible involvement of various CXCR4 agonists and antagonists in modulating platelet levels.

T-140 is a 14-residue synthetic peptide developed as a specific CXCR4 antagonist that suppress HIV-1 (X4-HIV-1) entry to T cells through specific binding to CXCR4 (Tamamura et al., 1998). Subsequently, peptide analogs of T-140 were developed as specific CXCR4 antagonist peptides with inhibitory activity at nanomolar levels (see Tamamura et al., 2003, WO 2002/020561 and WO 2004/020462).

WO 2002/020561 discloses novel peptide analogs and derivatives of T-140. The '561 publication demonstrates that the claimed peptides are potent CXCR4 inhibitors, manifesting high anti-HIV virus activity and low cytotoxicity.

WO 2004/020462 discloses additional novel peptide analogs and derivatives of T-140, including 4F-benzoyl-TN14003 (SEQ ID NO: 1). The '462 publication further discloses novel preventive and therapeutic compositions and methods of using same utilizing T-140 analogs for the treatment of cancer and chronic rheumatoid arthritis. The specification of '462 demonstrates the ability of these peptides to inhibit cancer cell migration, including breast cancer and leukemia cells, and to inhibit metastasis formation in vivo. Further demonstrated therein is inhibition of delayed-type hypersensitivity reaction in mice and collagen-induced arthritis, an animal model of rheumatoid arthritis.

WO 2004/087068 is directed to a method for treating or preventing a CXCR4 mediated pathology comprising administering a CXCR4 peptide antagonist to a host in an amount sufficient to inhibit CXCR4 signal transduction in a cell expressing a CXCR4 receptor or homologue thereof, wherein the CXCR4 peptide antagonist is not an antibody or fragment thereof. The '068 publication discloses that exemplary CXCR4 peptide antagonists include T140 and derivatives of T140, and that the pathology includes cancer such as breast, brain, pancreatic, ovarian, prostate, kidney, and non-small lunch cancer. Other publications directed to the use of CXCR4 antagonists in cancer therapy include, for example, WO 00/09152, US 2002/0156034, and WO 2004/024178.

A publication to some of the inventors of the present invention (Avniel et al., 2006) discloses that blocking the CXCR4/CXCL12 axis by a T-140 analog resulted in a significant reduction in eosinophil accumulation in the dermis and improved epithelialization, thus significantly improving skin recovery after burns.

Subsequently, it was discovered that under certain conditions, some of the functions of T-140 analogs may have CXCR4 super-agonistic properties, in addition to their CXCR4 antagonistic activity. WO 2008/075369 to some of the inventors of the present invention discloses compositions comprising T-140 peptide analogs having CXCR4 super-agonist activity and therapeutic uses thereof in modulating recovery of the hematopoietic system, particularly in the treatment of conditions associated with damage to the bone marrow. WO 2008/075370 to some of the inventors of the present invention discloses compositions comprising T-140 peptide analogs having CXCR4 super-agonist activity and therapeutic uses thereof in cancer therapy. WO 2008/075371 to some of the inventors of the present invention discloses compositions comprising T-140 peptide analogs having CXCR4 super-agonist activity and novel therapeutic uses thereof for immunotherapy and vaccination.

None of the prior art discloses or suggests that CXCR4 inhibitor peptides belonging to the T-140 analog family specifically promote the production of platelets in vivo, and particularly that these peptides may potentiate the ability of TPO to elevate platelet counts. There exists a long felt need for compositions and methods useful for treating and preventing platelet deficiencies. Therapeutic agents capable of enhancing platelet counts in an acute manner, useful for controlling bleeding in a subject in need thereof, would also be advantageous.

SUMMARY OF THE INVENTION

The present invention is directed to compositions and methods for enhancing platelet levels and for the treatment and prevention of conditions associated with thrombocytopenia and symptoms thereof. According to specific embodiments, the invention may be used for controlling or inhibiting bleeding in subjects having reduced platelet counts.

The instant invention is based, in part, on the surprising discovery that the known peptide 4F-benzoyl-TN14003 (4F-benzoyl-Arg-Arg-Nal-Cys-Tyr-Cit-Lys-DLys-Pro-Tyr-Arg-Cit-Cys-Arg-NH$_2$, SEQ ID NO:1) demonstrates a qualitatively and quantitatively distinct pattern of enhancing platelet levels compared to patterns characteristic of known thrombopoietic agents such as thrombopoietin (TPO). Specifically, it was surprisingly found that administration of the peptide to human subjects stimulated an immediate increase in blood platelet counts. Additionally, 4F-benzoyl-TN14003 was as potent as TPO in stimulating the production of platelets in healthy C57B1 mice, and was even more potent than TPO in enhancing platelet levels and reducing thrombocytopenia induced by chemotherapy. Moreover, 4F-benzoyl-TN14003 was surprisingly found to further stimulate the production of platelets in the blood and precursor colonies in the bone marrow induced by TPO. Thus, the peptides of the invention were unexpectedly found to have an advantageous dual effect in modulating thrombocyte levels: an immediate effect, characterized by elevation of blood platelets within minutes of administration, and a prolonged effect within days of administration, further accompanied by increased thrombopoiesis.

The present invention provides in some embodiments compositions and methods using 4F-benzoyl-TN14003 and analogs thereof, useful for stimulating the production of platelets and/or their blood circulation levels with improved efficiency and/or safety, as detailed herein.

The 4F-benzoyl-TN14003 analogs used in the novel compositions and methods of the invention (also referred to herein as "the peptides of the invention) are the structurally and functionally related peptides disclosed in patent applications WO 2002/020561 and WO 2004/020462, also known as "T-140 analogs", as detailed hereinbelow.

According to a first aspect, there is provided a method for elevating the levels of platelets in a subject in need thereof comprising administering to the subject an effective amount of a peptide of an amino acid sequence as set forth in SEQ ID NO: 1 or an analog thereof so as to elevate the levels of platelets in said subject.

In one embodiment, the method is used for elevating the levels of platelets in peripheral blood of said subject. In other embodiments, the methods of the invention may advantageously be used for increasing blood platelet levels in an acute manner, so as to induce platelet elevation within hours, or in other embodiments within minutes of administration. In one particular embodiment, the method induces a significant elevation of platelets in peripheral blood of said subject in an acute manner. In another particular embodiment said elevation occurs within one hour of administration of said peptide.

The levels of platelets may in some embodiments be elevated compared to their levels prior to initiation of treatment, or in other embodiments compared to their levels in absence of treatment (e.g. their predicted levels or their levels in a control subject).

The compositions and methods of the invention may be used in some embodiments in the treatment or prevention of conditions or symptoms associated with reduced or suboptimal platelet counts. According to some embodiments, the methods of the invention are used for treating or preventing thrombocytopenia in said subject.

In various embodiments, the methods may be used for treating or preventing the symptoms of acute or chronic thrombocytopenia, which may be accompanied by active bleeding or risk thereof. In a particular embodiment, the thrombocytopenia is characterized by platelet counts of less than 20,000/µL. In another particular embodiment, the method may be used for the treatment of severe thrombocytopenia characterized by platelet counts of less than 10,000/µL. In yet another particular embodiment said subject suffers from clinically significant bleeding.

In other embodiments, the methods may be used when a prompt or transient increase of the platelet count is required for tooth extractions, childbirth, surgery, or other invasive surgical procedures. For example, the method may be used when the subject is afflicted with thrombocytopenia and administration of said peptide is initiated within 24 hours of a surgical procedure (e.g. hours or minutes prior to surgery, during the surgical procedure or shortly thereafter).

In various embodiments, the thrombocytopenia may be selected from the group consisting of: thrombocytopenia associated with increased platelet destruction, thrombocytopenia associated with increased platelet sequestration, thrombocytopenia associated with platelet dilution and thrombocytopenia associated with impaired platelet production.

In a particular embodiment, said thrombocytopenia is associated with increased immunologic platelet destruction, e.g. idiopathic thrombocytopenic purpura or autoimmune thrombocytopenia. In another particular embodiment, said thrombocytopenia is associated with hepatitis C virus-related cirrhosis. In yet another particular embodiment, said thrombocytopenia may be associated with impaired platelet production e.g. congenital amegakaryocytic thrombocytopenia or thrombocytopenia with absent radii. In another embodiment, the thrombocytopenia is not associated with bone marrow deficiency or suppression. In yet another embodiment, said subject suffers from or is at risk of platelets reduction associated with exposure to radiation or chemotherapy.

The peptides of the invention may be administered to the subject either alone or in concurrent or sequential combination with other therapeutic agents, including but not limited to anti-cancer drugs, cytokines, hematopoietic agents, immunomodulatory drugs and coagulants or anticoagulants. Optionally, the peptide is administered to said subject in combination with at least one cytokine that stimulates platelets production, for example the peptide may be administered in combination with thrombopoietin or a thrombopoietin agonist. According to certain embodiments, the method may be used for enhancing thrombopoietin-induced elevation of platelet levels in said subject. In another embodiment the method may be used for reducing the duration of thrombocytopenia in said subject. In another embodiment said peptide is co-administered (in sequential or concurrent combination) with an additional drug or substance which would not otherwise be administered to said subject due to thrombocytopenia or risk thereof.

The peptides of the invention may be administered to the subject alone or in the form of a pharmaceutical composition comprising the peptide and at least one pharmaceutically acceptable carrier or excipient. Optionally, the peptide may be administered in the form of a pharmaceutical composition further comprising at least one cytokine that stimulates platelets production.

According to some embodiments, the peptides of the invention enhance blood platelets shortly after administration, and are thus advantageous in reducing or preventing bleeding in subjects, particularly subjects prone to bleeding due to platelet deficiency. In another aspect, there is provided a method of inhibiting bleeding in a subject in need thereof comprising administering to the subject an effective amount of a peptide of an amino acid sequence as set forth in SEQ ID NO:1 or an analog thereof so as to inhibit bleeding in said subject. In one embodiment, the method is used for reducing bleeding duration in said subject. In another embodiment, the method may be used for reducing bleeding intensity in said subject. In another embodiment, said subject is afflicted with thrombocytopenia. In another embodiment said subject suffers from clinically significant bleeding. In another particular embodiment the subject is afflicted with thrombocytopenia and administration of said peptide is initiated within 24 hours of a surgical procedure.

In another aspect, there is provided a pharmaceutical composition comprising as active ingredients effective amounts of a peptide of an amino acid sequence as set forth in SEQ ID NO: 1 or an analog thereof and at least one cytokine that stimulates platelet production, e.g. thrombopoietin or a thrombopoietin agonist.

Other objects, features and advantages of the present invention will become clear from the following description and drawings.

DETAILED DESCRIPTION OF THE INVENTION

Figure 1A:
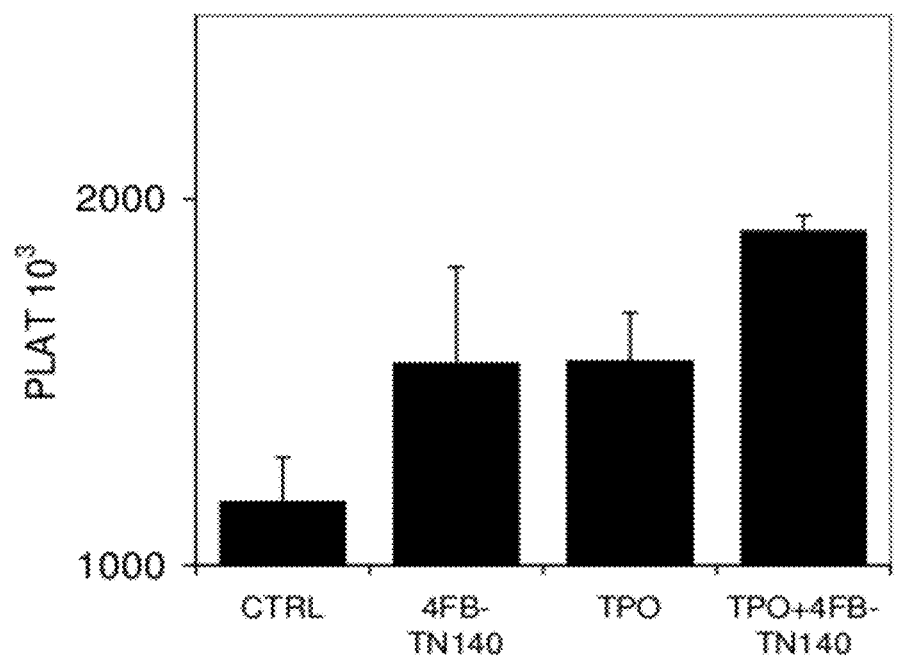
FIG. 1A demonstrates that 4F-benzoyl-TN14003 enhances the levels of platelets in blood by itself and in combination with Thrombopoietin.

The present invention is directed to novel compositions and methods wherein T-140 analog peptides are used to stimulate CXCR4-mediated platelet production and to elevate platelet levels in the blood.

The present invention is directed to novel therapeutic applications of T-140 analog peptides. The present invention discloses for the first time that 4F-benzoyl-TN14003 (SEQ ID NO:1), a known CXCR4 inhibitor belonging to the T-140 peptide family, mediates a unique pattern of stimulating platelets production and blood levels in healthy C57b1 mice as well as in thrombocytopenic mice and humans, immediately or following sequential injections. In addition, the present invention discloses for the first time that T-140 analogs stimulate the production of platelets alone or in combination with Thrombopoietin (TPO), and are thus suitable for use used in combination with TPO or analogs thereof that stimulate the thrombopoietin receptor c-MPL such as Romiplostim (AMG-531) and eltrombopag (SB-497115).

Thus, according to a first aspect of the present invention, there is provided a method for elevating the levels of platelets in a subject in need thereof, comprising administering to said subject a therapeutic agent comprising a peptide having an amino acid sequence as set forth in SEQ ID NO:1 or an analog thereof.

In another aspect, the invention provides methods for treating or preventing thrombocytopenia in a subject in need thereof, comprising administering to said subject a therapeutic agent comprising a peptide having an amino acid sequence as set forth in SEQ ID NO:1 or an analog thereof.

In another aspect there is provided a method for enhancing thrombopoietin-induced elevation of platelet levels in a subject in need thereof, comprising administering to said subject a therapeutic agent comprising a peptide having an amino acid sequence as set forth in SEQ ID NO: 1 or an analog thereof wherein said subject is concurrently treated with thrombopoietin or a thrombopoietin agonist.

In another aspect there is provided a method of inhibiting bleeding in a subject in need thereof comprising administering to said subject a therapeutic agent comprising a peptide having an amino acid sequence as set forth in SEQ ID NO:1 or an analog thereof.

In another aspect the invention provides a pharmaceutical composition comprising as active ingredients effective amounts of a peptide having an amino acid sequence as set forth in SEQ ID NO: 1 or an analog thereof and at least one cytokine that stimulates platelets production.

According to embodiments of the invention the peptide may be administered at an effective amount, so as to elevate the levels of platelets in said subject, induce an improvement of a clinical symptom of thrombocytopenia (e.g. bleeding) or prevent, delay or reduce the duration or magnitude thereof or enhance an activity of a co-administered drug or substance, as detailed herein.

Peptides

In this specification and drawings, the representations of amino acids, etc. by brevity codes are made by the use of the codes prescribed by IUPAC-IUB Commission on Biochemical Nomenclature or by the codes customarily used in the relevant art. Examples of such codes are shown below. If an optical isomer exists with respect to an amino acid, it preferably represents the L form unless otherwise expressly specified.

Gly or G: glycine; Ala or A: alanine; Val or V: valine; Leu or L: leucine; Ile or I: isoleucine; Ser or S: serine; Thr or T: threonine; Cys or C: cysteine; Met or M: methionine; Glu or E: glutamic acid; Asp or D: aspartic acid; Lys or K: lysine; Arg or R: arginine; His or H: histidine; Phe or F: phenylalanine; Tyr or Y: tyrosine; Trp or W: tryptophan; Pro or P: proline; Asn or N: asparagine; Gln or Q: glutamine; pGlu: pyroglutamic acid; Nal: 3-(2-naphthyl) alanine; Cit: citrulline; DLys: D-lysine; DCit: D-citrulline; DGlu: D-glutamic acid; Me: methyl group; Et: ethyl group; Bu: butyl group; Ph: phenyl group.

The substituents, protective group and reagents often used in this specification are indicated by the following codes.
BHA: benzhydrylamine
pMBHA: p-methylbenzhydrylamine
Tos p-toluenesulphonyl
CHO: formyl
HONB: N-hydroxy-5-norbornene-2,3-dicarboximide
OcHex: cyclohexyl ester
Bzl: benzyl
Cl$_2$-Bzl: dichloro-benzyl
Bom: benzyloxymethyl
Z: benzyloxycarbonyl
Br—Z: 2-bromobenzyloxycarbonyl
Boc: t-butyloxycarbonyl
DCM: dichloromethane
HOBt: 1-hydroxybenzotriazole
DCC: N,N'-dicyclohexylcarbodiimide
TFA: trifluoroacetic acid
DIEA: diisopropylethylamine
Fmoc: N-9-fluorenylmethoxycarbony
DNP: dinitrophenyl
Bum: tertiarybutoxymethyl
Trt: trityl
Ac: acetyl
Guanyl: guanyl
Succinyl: succinyl
glutaryl: glutaryl
TMguanyl: tetramethylguanyl
2F-benzoyl: 2-fluorobenzoyl
4F-benzoyl: 4-fluorobenzoyl
APA: 5-aminopentanoyl
ACA: 6-aminohexanoyl
desamino-Arg: 2-desamino-arginyl deamino TMG-APA: the following formula (IV):

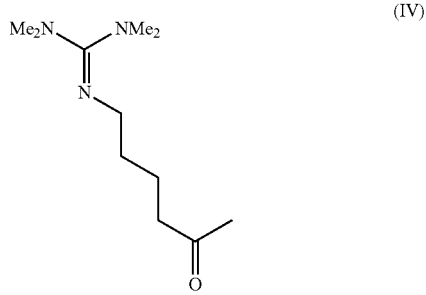

R—CH$_2$: the following formula (V):

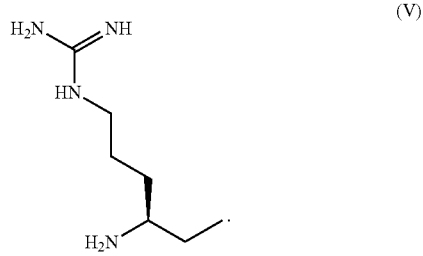

In N-terminal amino acids, [H—] indicates that the terminal amino group is not derivatized, and in C-terminal amino acids, [—OH] indicates that the terminal carboxyl group is not derivatized.

The 4F-benzoyl-TN14003 analogs of the invention belong to a family of structurally closely related peptides, also known as T-140 analogs. T-140 is a known synthetic peptide having the amino acid sequence H-Arg-Arg-Nal-Cys-Tyr-Arg-Lys-DLys-Pro-Tyr-Arg-Cit-Cys-Arg-OH (SEQ ID NO: 69, Tamamura et al., 2003), which was designed based on tachyplesin family polypeptides of the horseshoe crab. The preferable peptides of the invention include analogs and derivatives disclosed in patent applications WO 2002/020561 and WO 2004/020462. These peptides are synthetic peptides of artificial origin.

The term "analog" of SEQ ID NO: 1 as used herein thus relates to a peptide having at least 60% identity to SEQ ID NO: 1, preferably a peptide of Formulae (I) or (II) as defined herein.

In one aspect, the present invention relates to the use of pharmaceutical compositions comprising as an active ingredient a peptide indicated by the following formula (I) or a salt thereof:

```
               1  2  3   4   5   6  7  8  9 10 11 12  13  14      (I)
              A₁-A₂-A₃-Cys-Tyr-A₄-A₅-A₆-A₇-A₈-A₉-A₁₀-Cys-A₁₁
``` wherein:

$A_1$ in the above-mentioned formula (I) represents an arginine, lysine, ornithine, citrulline, alanine or glutamic acid residue (either L or D form) which may be derivatized at the N-terminus, or $A_1$ is a hydrogen atom, or it is preferable that $A_1$ is an arginine, citrulline, alanine or D-glutamic acid residue, or $A_1$ is a hydrogen atom (i.e. the amino acid at this position may be absent).

Examples of "N-terminal derivatized peptides" or "N-α-substituted derivatives" include, but are not limited to, those protected by formyl group; acyl group, e.g., acetyl group, propionyl group, butyryl group, pentanoyl group, C2-6alkanoyl group e.g. hexanoyl group, benzoyl group, arylcarbonyl group e.g. substituted benzoyl group (e.g.: 2-fluorobenzoyl, 3-fluorobenzoyl group, 4-fluorobenzoyl group, 2-bromobenzoyl group, 3-bromobenzoyl group, 4-bromobenzoyl group, 2-nitrobenzoyl group, 3-nitrobenzoyl group, 4-nitrobenzoyl group), succinyl group, glutaryl group; nicotinyl group; isonicotinyl group; alkylsulfonyl group (e.g.: methanesulfonyl group, ethanesulfonyl group, propanesulfonyl group, camphorsulfonyl group); arylsulfonyl group (e.g.: p-toluenesulfonyl group, 4-fluorobenzenesulfonyl group, mesitylenesulfonyl group, 4-aminobenzenesulfonyl group, dansyl group, 4-bromobenzenesulfonyl group) etc. Or, the N-terminal amino acid group may be absent.

Optionally and preferably, the peptide is derivatized at the N terminus with a substituted benzoyl group. In a particular embodiment, the substituted benzoyl group is a 4-fluorobenzoyl group. In another particular embodiment, the substituted benzoyl group is a 2-fluorobenzoyl group.

$A_2$ in the above-mentioned formula (I) represents an arginine or glutamic acid residue (either L or D form) if A1 is an arginine, lysine, ornithine, citrulline, alanine or glutamic acid residue (either L or D form) which may be derivatized at the N-terminus, or $A_2$ represents an arginine or glutamic acid residue (either L or D form) which may be derivatized at the N-terminus if $A_1$ is absent, or it is preferable that $A_2$ is an arginine or glutamic acid residue if $A_1$ is an arginine, citrulline, alanine or glutamic acid residue which may be derivatized at the N-terminus, or $A_2$ is an arginine or glutamic acid residue which may be derivatized at N-terminus if $A_1$ is absent. Examples of "peptides derivatized at the N-terminus" include, but are not limited to, the same ones as those mentioned in A1.

$A_3$ in the above-mentioned formula (I) represents an aromatic amino acid residue (e.g., phenylalanine, tryptophan, 3-(2-naphthyl)alanine, tyrosine, 4-fluorophenylalanine, 3-(1-naphthyl)alanine (either L or D form), or preferably, $A_3$ represents phenylalanine, tryptophan or 3-(2-naphthyl)alanine.

$A_4$ in the above-mentioned formula (I) represents an arginine, lysine, ornithine, citrulline, alanine or glutamic acid residue (either L or D form), or it is preferable that $A_4$ is an arginine, citrulline, alanine or L- or D-glutamic acid residue.

$A_5$ in the above-mentioned formula (I) represents an arginine, lysine, ornithine, citrulline, alanine or glutamic acid residue (either L or D form), or it is preferable that $A_5$ is an arginine, citrulline, alanine, lysine or glutamic acid residue.

$A_6$ in the above-mentioned formula (I) represents a proline, glycine, ornithine, lysine, alanine, citrulline, arginine or glutamic acid residue (either L or D form), or it is preferable that $A_6$ is a D-lysine, D-alanine, D-citrulline or D-glutamic acid residue.

$A_7$ in the above-mentioned formula (I) represents a proline, glycine, ornithine, lysine, alanine, citrulline or arginine residue (either L or D form), or it is preferable that $A_7$ is a proline or alanine residue.

$A_8$ in the above-mentioned formula (I) represents a tyrosine, phenylalanine, alanine, naphthylalanine, citrulline or glutamic acid residue (either L or D form), or it is preferable that $A_8$ is a tyrosine, alanine or D-glutamic acid residue.

$A_9$ in the above-mentioned formula (I) represents an arginine, lysine, ornithine, citrulline, alanine or glutamic acid residue (either L or D form), or it is preferable that $A_9$ is an arginine, citrulline or glutamic acid residue.

$A_{10}$ in the above-mentioned formula (I) represents a citrulline, glutamic acid, arginine or lysine residue (either L or D form), or it is preferable that $A_{10}$ is a citrulline or D-glutamic acid residue.

$A_{11}$ in the above-mentioned formula (I) represents an arginine, glutamic acid, lysine or citrulline residue (either L or D form) which may be derivatized at C-terminus, or it is preferable that $A_{11}$ is an arginine or glutamic acid residue which may be derivatized at the C-terminus.

"C-terminal derivatization" or "C-terminal carboxyl derivatization" includes, without limitation, amidation (—CONH$_2$, —CONHR, —CONRR') and esterification (—COOR). Herein, R and R' in amides and esters include, for example, $C_{1-6}$ alkyl group e.g. methyl, ethyl, n-propyl, isopropyl, or n-butyl, $C_{3-8}$ cycloalkyl group e.g. cyclopentyl, cyclohexyl, $C_{6-12}$ aryl group e.g. phenyl and α-naphthyl, phenyl-$C_{1-2}$ alkyl group e.g. benzyl, phenethyl or $C_{7-14}$ aralkyl group e.g. $C_{1-2}$ alkyl group e.g. α-naphthyl methyl group, and additionally, pivaloyloxymethyl group which is generally used as an oral bioavailable ester.

If a peptide of the present invention has carboxy groups (or carboxylates) at side-chain terminals other than C-terminus, the peptide having amidated or esterificated carboxy groups at side-chain terminals is included in the peptides of the present invention. As the amides and esters in this case, for example, the amides and esters exemplified in $A_{11}$ are similarly used. Also, the peptides of the present invention include peptides in which substituents (e.g. —OH, —SH, amino group, imidazole group, indole group, guanidino group, etc.) on the intramolecular amino acid side chains are protected by suitable protective group (e.g. C1-6 acyl group, C2-6 alkanoyl such as formyl group, acetyl group, etc.), or complex peptides such as glycopeptides combined with sugar chain in the above-mentioned peptides.

Salts of the peptides of the present invention include physiologically acceptable salts of acids or bases and particularly, physiologically acceptable acid addition salts are preferable. Such salts are exemplified by salts of inorganic acids (e.g. hydrochloric acid, phosphoric acid, hydrobromic acid, sulfuric acid), or salts of organic acids (e.g. acetic acid, formic acid, propionic acid, fumaric acid, maleic acid, succinic acid, tartaric acid, citric acid, malic acid, oxalic acid, benzoic acid, methanesulfonic acid, benzenesulfonic acid).

In one embodiment, the composition comprises a peptide as set forth in formula (I) as defined hereinabove, wherein $A_1$ is a glutamic acid residue or is absent (not present).

In another embodiment, the composition comprises a peptide as set forth in formula (I) as defined hereinabove, wherein $A_4$ is a glutamic acid residue.

In another embodiment, the composition comprises a peptide as set forth in formula (I) as defined hereinabove, wherein $A_6$ is a glutamic acid residue.

In another embodiment, the composition comprises a peptide as set forth in formula (I) as defined hereinabove, wherein $A_8$ is a glutamic acid residue.

In another embodiment, the composition comprises a peptide as set forth in formula (I) as defined hereinabove, wherein $A_9$ is a glutamic acid residue.

In another embodiment, the composition comprises a peptide as set forth in formula (I) as defined hereinabove, wherein $A_5$ is an arginine or glutamic acid residue.

In another embodiment, the composition comprises a peptide as set forth in formula (I) as defined hereinabove, wherein $A_{10}$ is a glutamic acid, arginine or lysine residue.

In another embodiment, the composition comprises a peptide as set forth in formula (I) as defined hereinabove, wherein $A_{11}$ is a glutamic acid, lysine or citrulline residue.

In another embodiment, the peptide has an amino acid sequence as set forth in any one of SEQ ID NOS: 1-72 presented in Table 1 herein:

TABLE 1

T-140 and currently preferred T-140 analogs

| Amino acid sequence | SEQ ID NO: | Analog |
|---|---|---|
| 4F-benzoyl-Arg-Arg-Nal-Cys-Tyr-Cit-Lys-DLys-Pro-Tyr-Arg-Cit-Cys-Arg-NH$_2$ | 1 | 4F-benzoyl-TN14003 |
| Ac-Arg-Arg-Nal-Cys-Tyr-Cit-Lys-DLys-Pro-Tyr-Arg-Cit-Cys-Arg-OH | 2 | AcTC14003 |
| Ac-Arg-Arg-Nal-Cys-Tyr-Arg-Lys-DCit-Pro-Tyr-Arg-Cit-Cys-Arg-OH | 3 | AcTC14005 |
| Ac-Arg-Arg-Nal-Cys-Tyr-Cit-Lys-DCit-Pro-Tyr-Arg-Cit-Cys-Arg-OH | 4 | AcTC14011 |
| Ac-Arg-Arg-Nal-Cys-Tyr-Cit-Lys-DLys-Pro-Tyr-Cit-Cit-Cys-Arg-OH | 5 | AcTC14013 |
| Ac-Cit-Arg-Nal-Cys-Tyr-Cit-Lys-DLys-Pro-Tyr-Arg-Cit-Cys-Arg-OH | 6 | AcTC14015 |
| Ac-Cit-Arg-Nal-Cys-Tyr-Arg-Lys-DCit-Pro-Tyr-Arg-Cit-Cys-Arg-OH | 7 | AcTC14017 |
| Ac-Arg-Arg-Nal-Cys-Tyr-Arg-Lys-DCit-Pro-Tyr-Cit-Cit-Cys-Arg-OH | 8 | AcTC14019 |
| Ac-Cit-Arg-Nal-Cys-Tyr-Arg-Lys-DLys-Pro-Tyr-Cit-Cit-Cys-Arg-OH | 9 | AcTC14021 |
| Ac-Arg-Arg-Nal-Cys-Tyr-Cit-Lys-DCit-Pro-Tyr-Arg-Cit-Cys-Arg-NH$_2$ | 10 | AcTC14012 |
| Ac-Arg-Arg-Nal-Cys-Tyr-Cit-Lys-DLys-Pro-Tyr-Cit-Cit-Cys-Arg-NH$_2$ | 11 | AcTC14014 |
| Ac-Cit-Arg-Nal-Cys-Tyr-Cit-Lys-DLys-Pro-Tyr-Arg-Cit-Cys-Arg-NH$_2$ | 12 | AcTC14016 |
| Ac-Cit-Arg-Nal-Cys-Tyr-Arg-Lys-DCit-Pro-Tyr-Arg-Cit-Cys-Arg-NH$_2$ | 13 | AcTC14018 |

TABLE 1-continued

T-140 and currently preferred T-140 analogs

| Amino acid sequence | SEQ ID NO: | Analog |
|---|---|---|
| Ac-Arg-Arg-Nal-Cys-Tyr-Arg-Lys-DCit-Pro-Tyr-Cit-Cit-Cys-Arg-NH$_2$ | 14 | AcTC14020 |
| Ac-Cit-Arg-Nal-Cys-Tyr-Arg-Lys-DLys-Pro-Tyr-Cit-Cit-Cys-Arg-NH$_2$ | 15 | AcTC14022 |
| H-DGlu-Arg-Nal-Cys-Tyr-Arg-Lys-DLys-Pro-Tyr-Arg-Cit-Cys-Arg-OH | 16 | TE14001 |
| H-Arg-Glu-Nal-Cys-Tyr-Arg-Lys-DLys-Pro-Tyr-Arg-Cit-Cys-Arg-OH | 17 | TE14002 |
| H-Arg-Arg-Nal-Cys-Tyr-Glu-Lys-DLys-Pro-Tyr-Arg-Cit-Cys-Arg-OH | 18 | TE14003 |
| H-Arg-Arg-Nal-Cys-Tyr-Arg-Glu-DLys-Pro-Tyr-Arg-Cit-Cys-Arg-OH | 19 | TE14004 |
| H-Arg-Arg-Nal-Cys-Tyr-Arg-Lys-DGlu-Pro-Tyr-Arg-Cit-Cys-Arg-OH | 20 | TE14005 |
| H-Arg-Arg-Nal-Cys-Tyr-Arg-Lys-DLys-Pro-Tyr-Glu-Cit-Cys-Arg-OH | 21 | TE14006 |
| H-Arg-Arg-Nal-Cys-Tyr-Arg-Lys-DLys-Pro-Tyr-Arg-Cit-Cys-Glu-OH | 22 | TE14007 |
| H-Arg-Arg-Nal-Cys-Tyr-Cit-Lys-DGlu-Pro-Tyr-Arg-Cit-Cys-Arg-NH$_2$ | 23 | TE14011 |
| H-Arg-Arg-Nal-Cys-Tyr-DGlu-Lys-DCit-Pro-Tyr-Arg-Cit-Cys-Arg-NH$_2$ | 24 | TE14012 |
| H-Arg-Arg-Nal-Cys-Tyr-DGlu-Lys-DGlu-Pro-Tyr-Arg-Cit-Cys-Arg-NH$_2$ | 25 | TE14013 |
| H-DGlu-Arg-Nal-Cys-Tyr-Cit-Lys-DGlu-Pro-Tyr-Arg-Cit-Cys-Arg-NH$_2$ | 26 | TE14014 |
| H-Arg-Arg-Nal-Cys-Tyr-Cit-Lys-DGlu-Pro-DGlu-Arg-Cit-Cys-Arg-NH$_2$ | 27 | TE14015 |
| H-Arg-Arg-Nal-Cys-Tyr-Cit-Lys-DGlu-Pro-Tyr-Arg-DGlu-Cys-Arg-NH$_2$ | 28 | TE14016 |
| Ac-DGlu-Arg-Nal-Cys-Tyr-Cit-Lys-DGlu-Pro-Tyr-Arg-Cit-Cys-Arg-NH$_2$ | 29 | AcTE14014 |
| Ac-Arg-Arg-Nal-Cys-Tyr-Cit-Lys-DGlu-Pro-DGlu-Arg-Cit-Cys-Arg-NH$_2$ | 30 | AcTE14015 |
| Ac-Arg-Arg-Nal-Cys-Tyr-Cit-Lys-DGlu-Pro-Tyr-Arg-DGlu-Cys-Arg-NH$_2$ | 31 | AcTE14016 |
| Ac-Arg-Arg-Nal-Cys-Tyr-Cit-Lys-DGlu-Pro-Tyr-Arg-Cit-Cys-Arg-NH$_2$ | 32 | TF1: AcTE14011 |
| guanyl-Arg-Arg-Nal-Cys-Tyr-Cit-Lys-DGlu-Pro-Tyr-Arg-Cit-Cys-Arg-NH$_2$ | 33 | TF2: guanyl-TE14011 |
| TMguanyl-Arg-Arg-Nal-Cys-Tyr-Cit-Lys-DGlu-Pro-Tyr-Arg-Cit-Cys-Arg-NH$_2$ | 34 | TF3: TMguanyl-TE14011 |
| TMguanyl-Arg-Nal-Cys-Tyr-Cit-Lys-DGlu-Pro-Tyr-Arg-Cit-Cys-Arg-NH$_2$ | 35 | TF4: TMguanyl-TE14011 (2-14) |
| 4F-benzoyl-Arg-Arg-Nal-Cys-Tyr-Cit-Lys-DGlu-Pro-Tyr-Arg-Cit-Cys-Arg-NH$_2$ | 36 | TF5: 4F-benzoyl-TE14011 |
| 2F-benzoyl-Arg-Arg-Nal-Cys-Tyr-Cit-Lys-DGlu-Pro-Tyr-Arg-Cit-Cys-Arg-NH$_2$ | 37 | TF6: 2F-benzoyl-TE14011 |
| APA-Arg-Nal-Cys-Tyr-Cit-Lys-DGlu-Pro-Tyr-Arg-Cit-Cys-Cys-Arg-NH$_2$ | 38 | TF7: APA-TE14011 (2-14) |
| desamino-R-Arg-Nal-Cys-Tyr-Cit-Lys-DGlu-Pro-Tyr-Arg-Cit-Cys-Arg-NH$_2$ | 39 | TF8: desamino-R-TE14011 (2-14) |
| Guanyl-Arg-Nal-Cys-Tyr-Cit-Lys-DGlu-Pro-Tyr-Arg-Cit-Cys-Arg-NH$_2$ | 40 | TF9: guanyl-TE14011 (2-14) |

TABLE 1-continued

T-140 and currently preferred T-140 analogs

| Amino acid sequence | SEQ ID NO: | Analog |
|---|---|---|
| succinyl-Arg-Nal-Cys-Tyr-Cit-Lys-DGlu-Pro-Tyr-Arg-Cit-Cys-Arg-NH$_2$ | 41 | TF10: succinyl-TE14011 (2-14) |
| glutaryl-Arg-Nal-Cys-Tyr-Cit-Lys-DGlu-Pro-Tyr-Arg-Cit-Cys-Arg-NH$_2$ | 42 | TF11: glutaryl-TE14011 (2-14) |
| deaminoTMG-APA-Arg-Nal-Cys-Tyr-Cit-Lys-DGlu-Pro-Tyr-Arg-Cit-Cys-Arg-NH$_2$ | 43 | TF12: deaminoTMG-APA-TE14011 (2-14) |
| R-CH2-Arg-Nal-Cis-Tyr-Cit-Lys-DGlu-Pro-Tyr-Arg-Cit-Cys-Arg-NH$_2$ | 44 | TF15: H-Arg-CH2NH-RTE14011 (2-14) |
| H-Arg-Nal-Cys-Tyr-Cit-Lys-DGlu-Pro-Tyr-Arg-Cit-Cys-Arg-NH$_2$ | 45 | TF17: TE14011 (2-14) |
| TMguanyl-Arg-Arg-Nal-Cys-Tyr-Cit-Lys-DCit-Pro-Tyr-Arg-Cit-Cys-Arg-NH$_2$ | 46 | TF18: TMguanyl-TC14012 |
| ACA-Arg-Arg-Nal-Cys-Tyr-Cit-Lys-DCit-Pro-Tyr-Arg-Cit-Cys-Arg-NH$_2$ | 47 | TF19: ACA-TC14012 |
| ACA-Arg-Arg-Nal-Cys-Tyr-Arg-Lys-DLys-Pro-Tyr-Arg-Cit-Cys-Arg-OH | 48 | TF20: ACA-T140 |
| H-Arg-Arg-Nal-Cys-Tyr-Cit-Arg-DLys-Pro-Tyr-Arg-Cit-Cys-Arg-NH$_2$ | 49 | TZ14011 |
| Ac-Arg-Arg-Nal-Cys-Tyr-Cit-Arg-DLys-Pro-Tyr-Arg-Cit-Cys-Arg-NH$_2$ | 50 | AcTZ14011 |
| Ac-Arg-Arg-Nal-Cys-Tyr-Cit-Lys-DLys-Pro-Tyr-Arg-Cit-Cys-Arg-NH$_2$ | 51 | AcTN14003 |
| Ac-Arg-Arg-Nal-Cys-Tyr-Arg-Lys-DCit-Pro-Tyr-Arg-Cit-Cys-Arg-NH$_2$ | 52 | AcTN14005 |
| 4F-benzoyl-Arg-Arg-Nal-Cys-Tyr-Cit-Lys-DGlu-Pro-Tyr-Arg-Cit-Cys-Arg-NHMe | 53 | 4F-benzoyl-TN14011-Me |
| 4F-benzoyl-Arg-Arg-Nal-Cys-Tyr-Cit-Lys-DGlu-Pro-Tyr-Arg-Cit-Cys-Arg-NHEt | 54 | 4F-benzoyl-TN14011-Et |
| 4F-benzoyl-Arg-Arg-Nal-Cys-Tyr-Cit-Lys-DGlu-Pro-Tyr-Arg-Cit-Cys-Arg-NHiPr | 55 | 4F-benzoyl-TN14011-iPr |
| 4F-benzoyl-Arg-Arg-Nal-Cys-Tyr-Cit-Lys-DGlu-Pro-Tyr-Arg-Cit-Cys-Arg-tyramine | 56 | 4F-benzoyl-TN14011-tyramine |
| H-Ala-Arg-Nal-Cys-Tyr-Arg-Lys-DLys-Pro-Tyr-Arg-Cit-Cys-Arg-OH | 57 | TA14001 |
| H-Arg-Arg-Nal-Cys-Tyr-Ala-Lys-DLys-Pro-Tyr-Arg-Cit-Cys-Arg-OH | 58 | TA14005 |
| H-Arg-Arg-Nal-Cys-Tyr-Arg-Ala-DLys-Pro-Tyr-Arg-Cit-Cys-Arg-OH | 59 | TA14006 |
| H-Arg-Arg-Nal-Cys-Tyr-Arg-Lys-DAla-Pro-Tyr-Arg-Cit-Cys-Arg-OH | 60 | TA14007 |
| H-Arg-Arg-Nal-Cys-Tyr-Arg-Lys-DLys-Ala-Tyr-Arg-Cit-Cys-Arg-OH | 61 | TA14008 |
| H-Arg-Arg-Nal-Cys-Tyr-Arg-Lys-DLys-Pro-Ala-Arg-Cit-Cys-Arg-OH | 62 | TA14009 |
| H-Arg-Arg-Nal-Cys-Tyr-Arg-Lys-DLys-Pro-Tyr-Ala-Cit-Cys-Arg-OH | 63 | TA14010 |
| H-Cit-Arg-Nal-Cys-Tyr-Arg-Lys-DLys-Pro-Tyr-Arg-Cit-Cys-Arg-OH | 64 | TC14001 |
| H-Arg-Arg-Nal-Cys-Tyr-Cit-Lys-DLys-Pro-Tyr-Arg-Cit-Cys-Arg-OH | 65 | TC14003 |

TABLE 1-continued

T-140 and currently preferred T-140 analogs

| Amino acid sequence | SEQ ID NO: | Analog |
|---|---|---|
| H-Arg-Arg-Nal-Cys-Tyr-Cit-Lys-DLys-Pro-Tyr-Arg-Cit-Cys-Arg-NH$_2$ | 66 | TN14003 |
| H-Arg-Arg-Nal-Cys-Tyr-Arg-Cit-DLys-Pro-Tyr-Arg-Cit-Cys-Arg-OH | 67 | TC14004 |
| H-Arg-Arg-Nal-Cys-Tyr-Cit-Lys-DCit-Pro-Tyr-Arg-Cit-Cys-Arg-NH$_2$ | 68 | TC14012 |
| H-Arg-Arg-Nal-Cys-Tyr-Arg-Lys-DLys-Pro-Tyr-Arg-Cit-Cys-Arg-OH | 69 | T-140 |
| H-Arg-Arg-Nal-Cys-Tyr-Cit-Lys-DCit-Pro-Tyr-Arg-Cit-Cys-Arg-OH | 70 | TC14011 |
| H-Arg-Arg-Nal-Cys-Tyr-Arg-Lys-DCit-Pro-Tyr-Arg-Cit-Cys-Arg-OH | 71 | TC14005 |
| H-Cit-Arg-Nal-Cys-Tyr-Arg-Lys-DCit-Pro-Tyr-Arg-Cit-Cys-Arg-NH$_2$ | 72 | TC14018 |

In each one of SEQ ID NOS: 1-72, two cysteine residues are preferably coupled in a disulfide bond.

Currently preferred peptides according to the present invention are peptides having an amino acid sequence as set forth in any one of SEQ ID NOS: 1-72. More preferably, it has been previously reported that the T-140 derivatives having an amino acid sequence as set forth in any one of SEQ ID NOS: 1-68 and 70-72 presented in Table 1 may have improved stability in serum and reduced cytotoxicity relative to T-140 (SEQ ID NO:69). However, T-140 may be suitable for use in the methods of the present invention according to some embodiments.

In another preferable embodiment, the peptide used in the compositions and methods of the invention consists essentially of an amino acid sequence as set forth in SEQ ID NO: 1. In another preferable embodiment, the peptide used in the compositions and methods of the invention is of an amino acid sequence as set forth in SEQ ID NO:1. In another embodiment, the peptide (analog) is at least 60%, preferably at least 70% and more preferably at least 80% homologous to SEQ ID NO: 1. In another embodiment, the peptide is at least about 90% homologous to SEQ ID NO: 1. In another embodiment, the peptide is at least about 95% homologous to SEQ ID NO: 1. Each possibility represents a separate embodiment of the present invention.

It is generally accepted, that the degree of homology between two sequences depends on both the degree of identity in their amino acid sequences and their identity with respect to their length. The peptide homologs of the invention are thus typically about 8-22 amino acids in length, more typically 14-20 amino acid in length or in other embodiments 13-15 amino acids in length, and in particular embodiments about 14 amino acids in length. In various other particular embodiments, the peptide is selected from SEQ ID NOS: 1-72, wherein each possibility represents a separate embodiment of the present invention.

In another particular embodiment, said peptide has an amino acid sequence as set forth in any one of SEQ ID NOS: 1-4, 10, 46, 47, 51-56, 65, 66, 68, 70 and 71. In another particular embodiment, said peptide has an amino acid sequence as set forth in any one of SEQ ID NOS: 4, 10, 46, 47, 68 and 70. In another particular embodiment, said peptide has an amino acid sequence as set forth in any one of SEQ ID NOS: 1, 2, 51, 65 and 66. In another particular embodiment, said peptide has an amino acid sequence as set forth in any one of SEQ ID NOS: 53-56. Each possibility represents a separate embodiment of the invention.

In a preferable particular embodiment, said peptide has an amino acid sequence as set forth in SEQ ID NO: 1. In another particular embodiment, said peptide has an amino acid sequence as set forth in SEQ ID NO:2. In another particular embodiment, said peptide has an amino acid sequence as set forth in SEQ ID NO: 51. In another particular embodiment, said peptide has an amino acid sequence as set forth in SEQ ID NO: 66. Each possibility represents a separate embodiment of the invention.

In another aspect, the invention relates to the use of a pharmaceutical composition comprising a peptide indicated by the following formula (II) or a salt thereof:

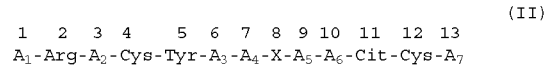

(II)

wherein:

$A_1$ represents an arginine, lysine, ornithine, citrulline or alanine residue or an N-α-substituted derivative of these amino acids or a hydrogen atom (namely may be absent);

$A_2$ represents an aromatic amino acid residue;

$A_3$, $A_4$ and $A_6$ each independently represent an arginine, lysine, ornithine, citrulline or alanine residue;

$A_5$ represents a tyrosine, phenylalanine, alanine, naphthylalanine or citrulline residue;

$A_7$ represents a lysine or arginine residue in which a carboxyl group may be amidated or esterified;

X is selected from the group consisting of:

(i) a peptide residue represented by the following formula (II):

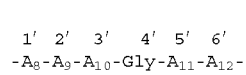

(III)

wherein $A_8$ and $A_{12}$ each independently represents an alanine, valine, leucine, isoleucine, serine, cysteine or methionine residue;

$A_9$ represents an aromatic amino acid residue, $A_{10}$ is selected from the same amino acid residues as in $A_3$, $A_{11}$ represents a tyrosine, phenylalanine, tryptophan, alanine, valine, leucine, isoleucine, serine, cysteine or methionine residue, provided that when both of the 1'-position and the 6'-position are cysteine residues, they may be bonded in a disulfide bond, (ii) a peptide selected from the group consisting of a D-ornithyl-proline, prolyl-D-ornithine, D-lysyl-proline, prolyl-D-lysine, D-arginyl-proline, prolyl-D-arginine, D-citrullyl-proline, D-citrullyl-alanine, D-alanyl-citrulline, prolyl-D-citrulline, glycyl-ornithine, ornithyl-glycine, glycyl-lysine, lysyl-glycine, glycyl-arginine, arginyl-glycine, glycyl-citrulline, citrullyl-glycine, D-alanyl-proline, and D-lysyl-alanine, and a hydrogen atom of a side chain ω-amino group of D-arginine, L-arginine, D-lysine, L-lysine, D-ornithine or L-ornithine which are constitutional amino acids of said peptide residues may be substituted by a ω-aminoacyl group, and the peptide residues of (i) and (ii) represent a peptide residue which binds amino acid residues at the 7-position and the 9-position through a peptide bond;

and the cysteine residues at the 4-position and the 12-position may be bonded in a disulfide bond;

provided that, in the above polypeptide or a salt thereof, either of the amino acid residues of $A_1$, $A_3$, $A_4$, $A_5$, $A_6$ and $A_7$ is an alanine or citrulline residue; or (iii) a peptide residue containing a D-citrulline, D-alanine, citrulline, or alanine residue) or a salt thereof.

In the polypeptides of the formula (II) of the present invention, $A_1$ is preferably an arginine, alanine or citrulline residue; $A_2$ is preferably a tryptophan or naphthylalanine residue; $A_3$ is preferably arginine, alanine or citrulline residue; $A_4$ is preferably a lysine, alanine or citrulline residue; X is preferably a D-lysyl-proline, D-alanyl-proline, D-lysyl-alanine or D-citrullyl-proline residue; $A_5$ is preferably a tyrosine or alanine residue; $A_6$ is preferably an arginine, alanine or citrulline residue; $A_7$ is preferably an arginine residue.

Exemplary peptides of the formula (II) are peptides wherein $A_1$, $A_6$ and $A_7$ are arginine residues, $A_2$ is a naphthylalanine residue, $A_3$ is a citrulline residue, $A_4$ is a lysine residue, X is a D-lysyl-proline residue, and $A_5$ is a tyrosine residue, a polypeptide of the formula (II) wherein $A_1$, $A_3$, $A_6$ and $A_7$ are arginine residues, $A_2$ is a naphthylalanine residue, $A_4$ is a lysine residue, X is a D-citrullyl-proline residue, and $A_5$ is a tyrosine residue, a polypeptide of the formula (II) wherein $A_1$, $A_6$ and $A_7$ are arginine residues, $A_2$ is a naphthylalanine residue, $A_3$ is a citrulline residue, $A_4$ is a lysine residue, X is a D-citrullyl-proline residue, $A_5$ is a tyrosine residue, and a polypeptide of the formula (II) wherein $A_1$ is a citrulline residue, $A_2$ is a naphthylalanine residue, $A_3$, $A_6$ and $A_7$ are arginine residues, $A_4$ is a lysine residue, X is a D-citrullyl-proline residue, $A_5$ is a tyrosine residue.

The peptides of formula (II) may be exemplified in another embodiment by a peptide of the formula (II) wherein $A_1$, $A_6$ and $A_7$ are arginine residues, $A_2$ is a naphthylalanine residue, $A_3$ is a alanine residue, $A_4$ is a lysine residue, X is a D-lysyl-proline residue, and $A_5$ is a tyrosine residue, a polypeptide of the formula (II) wherein $A_1$ is a citrulline residue, $A_2$ is a naphthylalanine residue, $A_3$, $A_6$ and $A_7$ are arginine residues, $A_4$ is a lysine residue, X is a D-lysyl-proline residue, and $A_5$ is a tyrosine residue, a polypeptide of the formula (II) wherein $A_1$, $A_3$ and $A_7$ are arginine residues, $A_2$ is a naphthylalanine residue, $A_4$ is a lysine residue, X is a D-lysyl-proline residue, $A_5$ is a tyrosine residue, and $A_6$ is a citrulline residue, a polypeptide of the formula (II) wherein $A_1$ and $A_3$ are citrulline residues, $A_2$ is a naphthylalanine residue, $A_4$ is a lysine residue, X is a D-lysyl-proline residue, $A_5$ is a tyrosine residue, $A_6$ and $A_7$ are arginine residues, and a polypeptide of the formula (II) wherein $A_1$, $A_3$ and $A_7$ are arginine residues, $A_2$ is a naphthylalanine residue, $A_4$ is a lysine residue, X is a D-citrullyl-proline residue, $A_5$ is a tyrosine residue, and $A_6$ is a citrulline residue.

The amino acid of $A_7$ as presented in formula II herein is preferably one in which the carboxyl group is amidated for improving stability of the polypeptide in vivo such as in serum, etc.

A peptide of the present invention includes a peptide or its amide, ester or salt containing the amino acid sequence which is substantially the same amino acid sequence as the sequence of any of the above-mentioned peptides. Here, "substantially the same amino acid sequence" means an amino acid sequence that is qualitatively identical in the activity of the peptide or the biological activity of the peptide (e.g. enhancing platelet levels) or the like. Accordingly, quantitative variances are acceptable to some extent (e.g. about 0.01 to 100 times, preferably 0.5 to 20 times, or more preferably 0.5 to 2 times). Therefore, one or more of the amino acids in the amino acid sequences indicated in any of the above-mentioned formula (I), (II) and SEQ ID NOS: 1-72 can have variances, so far as they have any of the above-mentioned properties. That is to say, in the present invention, any peptide (variant peptide) resulting from the variance in the amino acid sequence such as substitution, deletion or insertion (addition) etc. which brings about no significant change (i.e. a qualitatively different change, or a qualitatively identical but quantitatively significantly different change) in the physiological property or chemical property of the original (non-variant) peptide is deemed as substantially the same as the original (non-variant) peptide having no such variance, and, the amino acid sequence of such variant peptide is deemed as substantially the same as the amino acid sequence of the original (non-variant) peptide.

It is a well-known fact that generally, the changes such as substitution, deletion or insertion (addition) of an amino acid in a peptide sequence often do not make a significant change to physiological properties or chemical properties of such peptide. For example, it is generally considered that substitution of a certain amino acid by another amino acid of similar chemical properties results in a peptide having minimized deviation from the properties of the original peptide.

Amino acids are classified, using the similarity of their properties as to one of the criteria, into the following classes, for example: (i) nonpolar (hydrophobic) amino acids (examples: alanine, leucine, isoleucine, valine, proline, phenylalanine, tryptophan, methionine, etc.); (ii) polar (neutral) amino acids (examples: glycine, serine, threonine, cysteine, tyrosine, asparagine, glutamine, etc.); (iii) basic amino acids carrying positive electric charge (examples: arginine, lysine, histidine, etc.); (iv) acidic amino acids carrying negative electric charge (examples: asparatic acid, glutamic acid, etc.), and accordingly, amino acid substitution within each class can be conservative with regard to the property of a peptide (namely, substitution generating "substantially same" amino acid sequences). In other words, "substantially the same amino acid sequences" may include:

(i) amino acid sequences wherein 1 or more, or, in other embodiments, 1 to 3 amino acids were substituted by other amino acids in the amino acid sequences indicated in the above-mentioned formula (I), (II) and SEQ ID NOS:1-72;

(ii) amino acid sequences wherein 1 or more, or, in other embodiments, 1 to 3 amino acids were deleted in the amino acid sequences indicated in the above-mentioned formula (I), (II) and SEQ ID NOS:1-72;

(iii) amino acid sequences wherein 1 or more or, in other embodiments, 1 to 3 amino acids were added (inserted) in the amino acid sequences indicated in the above-mentioned formula (I), (II) and SEQ ID NOS:1-72; or (iv) peptides including modifications to amino acids (particularly, the side chains thereof) among the peptides having the amino acid sequences indicated in above (i), (ii) or (iii), or esters, amides or salts thereof.

A peptide of the present invention, if and when the substitution, deletion, insertion (addition), modification, etc. of above (i) to (iv) is intentionally or incidentally provided in the amino acid sequence thereof, can be varied to a stable peptide against heat or protease or a high-activity peptide having more enhanced activity. The peptides of the present invention include also these variant peptides or amides thereof, esters thereof or salts thereof.

Furthermore, among the peptides of the present invention are the peptide consisting of the amino acid sequence indicated in any of the above-mentioned formula (I), (II) and SEQ ID NOS:1-72, and the peptide containing the amino acid sequence sharing the homology of about 50 to 99.9% (preferably, 70 to 99.9%, more preferably 90 to 99.9%) with the foregoing amino acid sequence and having the activities of substantially the same nature as the peptide consisting of the amino acid sequence indicated in any of the above-mentioned formula (I), (II) and SEQ ID NOS:1-72, or amides thereof, esters thereof or salts thereof.

Peptide analogs of the invention include in other embodiments peptides which are identical to SEQ ID NO: 1 or other peptides disclosed herein with respect to their amino acid sequence but have different derivatizing groups (e.g. N' derivatization or C' derivatization), as long as they are qualitatively identical in their activity with respect to platelet levels as the peptides disclosed herein.

The amides, esters or salts of the peptide having the amino acid sequence indicated in any of the above-mentioned SEQ ID NOS: 1-72 include the same ones as are exemplified for the peptide indicated in the above-mentioned formula (I). Preferably, the peptide having the amino acid sequence indicated in any of the above-mentioned SEQ ID NOS: 1-72 is amidated at the carboxyl group of the C-terminal amino acid residue.

The peptides of the present invention including the peptide containing the amino acid sequence indicated in any of the above-mentioned SEQ ID NOS: 1-72 can be produced by conventionally known methods of synthesizing peptides. For the syntheses of peptides, either solid phase peptide synthesis or liquid phase synthesis may be utilized. Namely, an expected peptide can be produced by condensing a partial peptide able to constitute a peptide or an amino acid with remaining portions, and if the product has a protecting group, by eliminating the protecting group. As the known condensation methods and elimination of protecting groups, the following examples (1) to (5) are included:

(1) M. Bodanszky and M. A. Ondetti, Peptide Synthesis, Interscience Publishers, New York (1966).
(2) Schroeder and Luebke, The Peptide, Academic Press, New York (1965).
(3) N. Izumiya, et. al., Peptide Synthesis, Basics and Practice, Maruzen, Tokyo (1975).
(4) H. Yajima and S. Sakakibara, Seikagaku-Jikken-Koza I, Protein Chemistry IV, Tokyo Kagakudojin, Tokyo, pp 205 (1977).
(5) H. Yajima, Zoku-Iyakuhin-no-Kaihatsu, Vol. 14, Peptide Synthesis, Hirokawa Publishing Co., Tokyo (1991).

As practical methods for syntheses of peptides, the following examples can be given:

Generally, commercially available resins for synthesis of polypeptides can be used. Such resins include, for example, chloromethyl resin, hydroxymethyl resin, benzhydroxylamine resin, aminomethyl resin, 4-hydroxybenzylalcohol resin, 4-methylbenzhydroxylamine resin, PAM resin, 4-hydroxymethylmethylphenylacetoamidomethyl resin, polyacrylamide resin, 4-(2',4'-dimetoxyphenyl-hydroxymethyl) phenoxy resin, 4-2',4'-dimetoxyphenyl-Fmoc aminoethylphenoxy resin, etc. Using such resin, an amino acid with suitably protected α-amino group and side chain functional group is condensed on the resin to the sequence of the expected polypeptide in accordance with conventionally known condensation methods. In the last stage of the reaction, the polypeptide is cleared from the resin and simultaneously various protective groups are removed, and then, by carrying out intramolecular disulfide bond-forming reaction in highly diluted solution, the expected polypeptide or amide thereof is obtained. For the above-mentioned condensation of the protected amino acid, various activated reagents usable for the syntheses of polypeptides can be used, but it is particularly better to use carboxylmides. Among such carboxylmides are DCC, N,N'-diisopropylcarbodiimide, N-ethyl-N'-(3-dimethylaminopropyl)cabodiimde, etc. For the activation by these, together with racemization inhibitory additives (for example, HOBt, HOOBt), a protected amino acid is added directly to the resin, or after activating the protected amino acid as symmetric acid anhydride or HOBt ester or HOOBt ester, it can be added to ester resin.

Solvents used for the activation of protected amino acids and the condensation with resins can be chosen from among the solvents known to be usable for polypeptide condensation reactions. For example, acid amides such as N,N-dimethylformamide, N,N-dimethylacetoamide and N-methylpyrrolidone, halogenated hydrocarbons such as methylene chloride and chloroform, alcohols such as trifluoroethanol, sulfoxides such as methyl sulfoxide, ethers such as pyridine, dioxane and tetrahydrofuran, nitriles such as acetonitrile and propionitrile, esters such as methyl acetate and ethyl acetate, or appropriated mixtures of the foregoing are used. A solvent used for activation of a protected amino acid or its condensation with resin can be selected from among the solvents known to be usable for condensing reactions of polypeptides. The reaction temperature is appropriately set within the scope known to be applicable to polypeptide bond forming reactions, usually, at −20° C. to 50° C. Activated amino acid derivatives are usually used at 1.5 to 4 times excess. According to the result of tests adopting ninhydrin reaction, if the condensation is insufficient, the repetition of condensation reactions without eliminating protective groups can lead to sufficient condensation. If sufficient condensation is attained by the repetition of reactions, unreacted amino acids can be acetylated by the use of acetic anhydride or acetylimidazole.

The protective group of the amino group used as ingredients include, for example, Z, Boc, tertialypentyloxycarbony, isobornyloxycarbonyl, 4-methoxybenzyloxycabonyl, Cl—Z, Br—Z, adamantyloxycabonyl, trifluoroacetyl, phtaloyl, formyl, 2-nitrophenylsulphenyl, diphenylphosphinothioyl, Fmoc, etc. Carboxyl group can be protected, for example, by alkyl esterification (e.g. straight-chain, branching or circular alkyl esterification of methyl, ethyl, propyl, butyl, tertialbutyl, cyclopentyl, cyclohexyl, cycloheptyl, cyclooctyl, 2-adamantyl, etc.), aralkyl esterification (e.g. benzylester, 4-nitrobenzylester, 4-methoxybenzylester, 4-chlorbenzylester, benzhydryl esterification), phenacylesterification, benzylcarbonylhydrazidation, tertialybutoxycarbonylhydrazidation, tritylhydrazidation, etc. The hydroxyl group of serine can be protected, for example, by esterification or etherification. The groups suitable for this esterification include, for example, groups derivatized from carboxylic acid such as lower alkanoyl group such as acetyl group, aroyl group such as benzoyl group, benzyloxycarbonyl group, ethoxycarbonyl group. The groups suitable for etherification include, for example, benzyl group, tetrahydropiranyl group, tertiarybutyl group, etc. As the protective groups of phenolic OH group of tyrosine, for example, Bzl, Cl2-Bzl, 2-nitrobenzyl, Br—Z, tertiarlybutyl, etc. are used. As the protective groups of imidazole of histidine, for example, Tos, 4-methoxy-2,3,6-trimethylbenzenesulfonyl, DNP, benzyloxymethyl, Bum, Boc, Trt, Fmoc etc. are used.

Ingredients with activated carboxyl groups include, for example, corresponding acid anhydride, azide, active ester [ester of alcohol (e.g. pentachlorophenol, 2,4,5-trichlorophenol, 2,4-dinitrophenol, cyanomethylalcohol, p-nitrophenol, HONB, N-hydroxysuccimide, N-hydroxyphtalimide, HOBt] are used. Ingredients with activated amino group include, for example, corresponding phosphoric amide. As the methods to remove (eliminate) protective groups, for example, catalytic reduction in hydrogen airstream in the presence of a catalyst such as Pd-black or Pd-carbon, acid treatment by anhydrous hydrogen fluoride, methanesulfonic acid, trifluoromethanesulfonic acid, trifluoroacetic acid or a mixture thereof, etc, base treatment by diisopropylethylamine, triethylamine, piperidine, piperadine, etc., and reduction by natrium in liquid ammonia are used. Elimination reaction by the above-mentioned acid treatment is done generally at the temperature of about −20° C. to 40° C., but in the acid treatment, it is effective to add a cation trapping agent such as anisole, phenol, thioanisole, m-cresol, p-cresol, dimethylsulfide, 1,4-butanedithiol, 1,2-ethanedithiol. 2,4-dinitrophenyl group used as the protective group of imidazole of histidine is removed by thiophenol treatment. Formyl group used as the protective group of indole of tryptophan is removed by elimination of protection by the above-mentioned acid treatment in the presence of 1,2-ethanedithiol, 1,4-butanedithiol, etc. and also is removed by alkaline treatment by dilute sodium hydroxide solution, dilute ammonia, etc.

Protection and protective group of functional groups not to be involved in the reaction of ingredients, and elimination of such protective group, and activation of functional groups to be involved in the reaction, etc. can be appropriately selected from among conventionally known groups or conventionally known measures. As alternative methods to obtain amides of polypeptides, there is, for example, a method to manufacture, after amidating and protecting α-carboxyl group of carboxy-terminal amino acid and then extending the peptide chain to the desired chain length on the side of amino group, a polypeptide eliminating the protective group of α-amino group of the N-terminus of such peptide chain and a polypeptide eliminating the protective group of carboxyl group of the C-terminus, and then these two peptides are condensed in the above-mentioned mixed solvent. The details of the condensation reaction are the same as described above. After purifying the protected polypeptide obtained by the condensation, the desired raw polypeptide can be obtained by eliminating all the protective groups by the above-mentioned method. Having purified this raw polypeptide using various known purification methods, if the main fraction is freeze-dried, an amide type of the desired polypeptide can be obtained. To get an ester type of the polypeptide, for example, make an amino acid ester by condensing α-carboxyl group of carboxy-terminal amino acid with the desired alcohols, and then, the ester type of the desired polypeptide can be obtained in the same way as the amide type of the polypeptide.

After the reaction, the peptides of the present invention can be purified and isolated by combining usual purification methods such as solvent extraction, distillation, column chromatography, liquid chromatography, re-crystallization, etc. If a peptide obtained by the above-mentioned methods is a salt-free type, it can be converted to a suitable salt by known methods, or if such peptide is a salt, it can be converted to a salt-free type by known methods.

Pharmaceutical Compositions and Kits

As used herein, a "pharmaceutical composition" refers to a preparation of one or more of the active ingredients described herein with other chemical components such as physiologically suitable carriers and excipients. The purpose of a pharmaceutical composition is to facilitate administration of a compound to an organism.

Hereinafter, the phrases "physiologically acceptable carrier" and "pharmaceutically acceptable carrier", which may be used interchangeably, refer to a carrier or a diluent that does not cause significant irritation to an organism and does not abrogate the biological activity and properties of the administered compound.

Herein, the term "excipient" refers to an inert substance added to a pharmaceutical composition to further facilitate administration of an active ingredient. Examples, without limitation, of excipients include calcium carbonate, calcium phosphate, various sugars and types of starch, cellulose derivatives, gelatin, vegetable oils, and polyethylene glycols.

Techniques for formulation and administration of drugs may be found in the latest edition of "Remington's Pharmaceutical Sciences", Mack Publishing Co., Easton, Pa., which is herein fully incorporated by reference (Remington: The Science and Practice of Pharmacy, Gennaro, A., Lippincott, Williams & Wilkins, Philadelphia, Pa., $20^{th}$ ed, 2000).

Pharmaceutical compositions of the present invention may be manufactured by processes well known in the art, e.g., by means of conventional mixing, dissolving, granulating, dragee-making, levigating, emulsifying, encapsulating, entrapping, or lyophilizing processes.

Pharmaceutical compositions for use in accordance with the present invention thus may be formulated in conventional manner using one or more physiologically acceptable carriers comprising excipients and auxiliaries, which facilitate processing of the active ingredients into preparations that can be used pharmaceutically. Proper formulation is dependent upon the route of administration chosen.

The pharmaceutical compositions of the invention are suitable for administration systemically or in a local manner, for example, via injection of the pharmaceutical composition directly into a tissue region of a patient (e.g. intralesional injection).

For injection, the active ingredients of the pharmaceutical composition may be formulated in aqueous solutions, preferably in physiologically compatible buffers such as Hank's solution, Ringer's solution, or physiological salt buffer.

Pharmaceutical compositions for potential administration include aqueous solutions of the active preparation in water-soluble form. Additionally, suspensions of the active ingredients may be prepared as appropriate oily or water-based injection suspensions. Suitable lipophilic solvents or vehicles include fatty oils such as sesame oil, or synthetic fatty acid esters such as ethyl oleate, triglycerides, or liposomes. Aqueous injection suspensions may contain substances that increase the viscosity of the suspension, such as sodium carboxymethyl cellulose, sorbitol, or dextran. Optionally, the suspension may also contain suitable stabilizers or agents that increase the solubility of the active ingredients, to allow for the preparation of highly concentrated solutions.

Alternatively, the active ingredient may be in powder form for constitution with a suitable vehicle, e.g., a sterile, pyrogen-free, water-based solution, before use.

For oral administration, the pharmaceutical composition can be formulated readily by combining the active compounds with pharmaceutically acceptable carriers well known in the art. Such carriers enable the pharmaceutical composition to be formulated as tablets, pills, dragees, capsules, liquids, gels, syrups, slurries, suspensions, and the like, for oral ingestion by a patient. Pharmacological preparations for oral use can be made using a solid excipient, optionally grinding the resulting mixture, and processing the mixture of granules, after adding suitable auxiliaries as desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, and sodium carbomethylcellulose; and/or physiologically acceptable polymers such as polyvinylpyrrolidone (PVP). If desired, disintegrating agents, such as cross-linked polyvinyl pyrrolidone, agar, or alginic acid or a salt thereof, such as sodium alginate, may be added.

Dragee cores are provided with suitable coatings. For this purpose, concentrated sugar solutions may be used which may optionally contain gum arabic, talc, polyvinyl pyrrolidone, carbopol gel, polyethylene glycol, titanium dioxide, lacquer solutions, and suitable organic solvents or solvent mixtures. Dyestuffs or pigments may be added to the tablets or dragee coatings for identification or to characterize different combinations of active compound doses.

Pharmaceutical compositions that can be used orally include push-fit capsules made of gelatin, as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate, and, optionally, stabilizers. In soft capsules, the active ingredients may be dissolved or suspended in suitable liquids, such as fatty oils, liquid paraffin, or liquid polyethylene glycols. In addition, stabilizers may be added. All formulations for oral administration should be in dosages suitable for the chosen route of administration.

For buccal administration, the compositions may take the form of tablets or lozenges formulated in conventional manner.

Pharmaceutical compositions suitable for use in the context of the present invention include compositions wherein the active ingredients are contained in an amount effective to achieve the intended purpose. Determination of a therapeutically effective amount is well within the capability of those skilled in the art, especially in light of the detailed disclosure provided herein. Exemplary doses for human use may be in some embodiments 0.03-10 mg/kg, 0.1-10 mg/kg, 0.1-2 mg/kg, 0.1-1 mg/kg, 0.3-10 mg/kg, 0.3-2 mg/kg, 0.3-1 mg/kg or 0.3-0.9 mg/kg. For example it was found that doses of 0.3 mg/kg or more administered subcutaneously were effective in elevating blood platelet levels in human patients receiving chemotherapy.

Optionally, the peptides of the invention may be formulated, or administered in (concurrent or sequential) combination, with one or more additional active agents. In certain embodiments, the composition may further comprise, in addition to a peptide of the invention, one or more other agents that induce or enhance platelets production, e.g. TPO and TPO agonists. TPO agonists (or TPO receptor agonists) as used herein refer to molecules having a pharmacological activity characteristic of TPO and substantially similar to that of TPO. For example, such molecules may be TPO analogs or mimetics, or other molecules (such as proteins, peptides, antibodies and small molecules) that bind to the c-mp1 (TpoR) receptor, the physiological target of thrombopoietin, in an agonistic manner. Common TPO agonists have thrombopoietic activity, e.g. in increasing proliferation and differentiation of megakaryocytes. In various specific embodiments, the peptides of the invention may act in synergistic or additive manners to enhance various aspects of thrombopoiesis or blood platelet levels.

Specific examples of agents that induce or enhance platelets production including commercially available TPO agonists are Romiplostim (AMG-531, marketed under the trade name Nplate), developed by Amgen as a Thrombopoietin receptor-binding peptibody; Eltrombopag (rINN, SB-497115) marketed by GlaxoSmithKline under the trade name Promacta as a TPO receptor agonist; AKR-501 developed by AkaRx as a small molecule thrombopoietin receptor agonist; LGD-4665 developed by Ligand Pharmaceuticals as an oral thrombopoietin mimetic; N-acetylcysteine, suggested by Adherex Technologies as a chemoprotectant for the prevention of bone marrow suppression resulting from certain chemotherapy regimens; peg-TPOmp developed by Johnson & Johnson as a pegylated peptide thrombopoietin receptor agonist; and SB-559448, developed by GlaxoSmithKline and Ligand Pharmaceuticals as an oral non-peptide small molecule thrombopoietin receptor agonist. Other cytokines that may stimulate platelet production include e.g. IL-1, IL-3, IL-6 and GM-CSF.

Appropriate doses and administration schemes of such co-administered drugs e.g. TPO agonists are available and may be adapted as necessary by the skilled artisan. For example, Nplate (Romiplostim) is a thrombopoietin receptor agonist indicated for the treatment of thrombocytopenia in patients with chronic immune (idiopathic) thrombocytopenic purpura (ITP) who have had an insufficient response to corticosteroids, immunoglobulins, or splenectomy. Nplate is currently indicated at a maximal weekly dose of 10 mcg/kg.

Optionally, the additional active agent may also include other cytokines or cytokine receptor modulators. For example, it was demonstrated herein that granulocyte-colony stimulating factor (G-CSF) did not interfere with the ability of the peptide to inhibit thrombocytopenia and thus in some embodiments the peptides of the invention may be administered in combination with G-CSF or an analog or agonist thereof (having the biological activity of G-CSF as understood by the skilled artisan, e.g. filgrastim, lenograstim and nartograstim). The peptides of the invention were able, either alone or when administered with G-CSF, to elevate platelet counts in both acute and chronic manners (within minutes or days) in vivo.

In other embodiments, the peptides may be used in combination with anti-cancer treatments, e.g. with one or more chemotherapeutic drugs. For example, it was hereby demonstrated that the peptides of the invention may be safely administered with the 5-fluorouracil (5-FU) to inhibit chemotherapy-induced thrombocytopenia. 5-FU is an exemplary antimetabolite chemotherapeutic drug acting as a pyrimidine analog that is used in the treatment of cancer. In some embodiments co-administration of a peptide of the invention with a chemotherapeutic drug lowers the risk of thrombocytopenia, thus allowing chemotherapy to be continued for a prolonged duration and/or at increased doses that would otherwise be contraindicated due to adverse effects. In other embodiments, the chemotherapeutic drug and the peptide of the invention may have a synergistic effect at inhibiting cancer formation with concomitantly reducing the risk of bleeding. In another embodiment, the compositions and methods of the invention enhance the safety of chemotherapy in a subject afflicted with cancer. In another embodiment, the compositions and methods of the invention enhance the effectiveness of chemotherapy in a subject afflicted with cancer. In various embodiments, the combined treatment enhances platelet levels in both acute and chronic manners in cancer patients undergoing chemotherapy. In some cases, the use of such anti-cancer drugs and other drugs or therapeutic regimens may be excluded or restricted in thrombocytopenic patients. For example, in thrombocytopenic patients with cirrhosis due to hepatitis C, low platelet counts may preclude interferon treatment. In some embodiments the peptides of the invention may be co-administered (or co-formulated to form a pharmaceutical composition) with an additional drug or substance (e.g. a chemotherapeutic drug) to facilitate the use of the drug or substance in patients which would otherwise not receive the drug due to thrombocytopenia or risk thereof.

Chemotherapeutic drugs include but are not limited to alkylating agents (e.g. Cyclophosphamide, Ifosphamide, Melphalan, Chlorambucil, BCNU, CCNU, Decarbazine, Procarbazine, Busulfan, and Thiotepa); antimetabolites (e.g. Methotraxate, 5-Fluorouracil, Cytarabine, Gemcitabine, 6-mercaptopurine, 6-thioguanine, Fludarabine, and Cladribine); anthracyclins (e.g. daunorubicin. Doxorubicin, Idarubicin, Epirubicin and Mitoxantrone); camptothecins (e.g. irinotecan and topotecan); taxanes (e.g. paclitaxel and docetaxel); and platinums (e.g. Cisplatin, carboplatin, and Oxaliplatin).

In certain other embodiments, the peptides of the invention may be co-administered or co-formulated with other platelet modulators or coagulation modulators.

In yet other exemplary embodiments the peptides may be co-administered or co-formulated with other agents that are used in the treatment of thrombocytopenia, as known in the art. For example, immunomodulating drugs, e.g. corticosteroids or immunosuppressants that are indicated for the treatment of thrombocytopenia in certain cases may be uses according to standard protocols.

In yet another embodiment, the composition consists of a peptide of the invention as a sole active ingredient.

In another embodiment, combinations according to the invention are provided in the form of kits, comprising one or more active ingredients (a peptide of the invention and/or the additional active ingredients as specified herein) and instructions for co-administering the active ingredients in the methods of the invention. For example, in another embodiment there is provided a there kit comprising i) at least one cytokine that stimulates thrombopoiesis, preferably TPO or TPO agonists, and ii) a peptide of an amino acid sequence as set forth in SEQ ID NO:1 or an analog thereof. In another embodiment, there is provided a pharmaceutical pack containing a course of treatment for one individual mammal comprising a container having a unit of a T-140 analog of the invention in unit dosage form, and a container having a unit of TPO.

Therapeutic Use

In various embodiments, the peptides of the invention are useful for the treatment of platelet disorders. In general, platelet disorders include disorders associated with an abnormal increase in platelets (thrombocythemia, a myeloproliferative disorder), a decrease in platelets (thrombocytopenia), or platelet dysfunction. Any of these conditions may cause defective formation of haemostatic plugs and bleeding. According to embodiments of the invention, the methods and compositions of the invention are particularly useful for elevating platelet counts in conditions characterized by decreased or suboptimal platelet levels and in the treatment and prevention of thrombocytopenia.

Causes of thrombocytopenia can be classified by mechanism and include failed platelet production, increased splenic sequestration of platelets with normal platelet survival, increased platelet destruction or consumption (both immunologic and nonimmunologic causes), dilution of platelets, and a combination of these. Diagnosis of the particular condition is typically performed using peripheral blood smears and if necessary bone marrow aspiration; increased splenic sequestration is suggested by splenomegaly.

Thrombocytopenia may be caused by diminished or absent megakaryocytes in the bone marrow, e.g. in patients with aplastic anemia or leukemia, in patients receiving myelosuppressive drugs (e.g. chemotherapy), and in some patients with paroxysmal nocturnal hemoglobinuria. Thrombocytopenia may also stem from diminished platelet production despite the presence of megakaryocytes in the bone marrow, e.g. in alcohol-induced thrombocytopenia, HIV-associated thrombocytopenia, Myelodysplastic syndromes and vitamin B12 or folate (folic acid) deficiency.

For example, Congenital Amegakaryocytic Thrombocytopenia (CAMT) is a rare hereditary disease, manifested by thrombocytopenia and megakaryocytopenia (low numbers of platelets and megakaryocytes). There is an absence of megakaryocytes in the bone marrow with no associated physical abnormalities. The cause for this disorder appears to be a mutation in the gene for the TPO receptor, c-mpl, despite high levels of serum TPO. The primary treatment for CAMT is bone marrow transplantation. Frequent platelet transfusions are typically required to ensure that platelet counts do not fall to dangerous levels.

TAR Syndrome (Thrombocytopenia with Absent Radii) is a rare genetic disorder which is characterized by the absence of the radius bone in the forearm, and a dramatically reduced platelet count. Symptoms of thrombocytopenia lead to bruising and potentially life-threatening hemorrhage. The platelet abnormality reflects platelet hypoproduction, which might stem from abnormal or inhibited megakaryocytopoiesis, possibly associated with lack of response to thrombopoietin.

The main treatment for TAR patients is platelet transfusion, wherein hematopoietic stem cell transplantation (HSCT) is an option for patients who remain thrombocytopenic with bleeding despite platelet transfusions. In addition, splenectomy may be effective in adult patients. Patients with thrombocytopenia have responded to cytokine treatment with erythropoietin and interleukin-6, although no established treatment regimen has been clinically approved. javascript:showcontent('active','references');

Thrombocytopenia due to splenic sequestration may occur in various disorders that produce splenomegaly, e.g. cirrhosis with congestive splenomegaly, Gaucher's disease and myelofibrosis with myeloid metaplasia. Sequestration is expected in patients with congestive splenomegaly caused by advanced cirrhosis. The platelet count usually is >30,000/μL unless the disorder producing the splenomegaly also impairs platelet production (e.g., in myelofibrosis with myeloid metaplasia). Platelets are released from the spleen by epinephrine and therefore may be available at a time of stress. Therefore, thrombocytopenia caused only by splenic sequestration does not typically cause bleeding. Splenectomy corrects the thrombocytopenia but is not indicated unless severe thrombocytopenia from simultaneous marrow failure is present.

Immunologic destruction of platelets occurs e.g. in connective tissue disorders, drug-induced thrombocytopenia, HIV-associated thrombocytopenia, Idiopathic thrombocytopenic purpura (ITP), lymphoproliferative disorders, neonatal alloimmune thrombocytopenia, posttransfusion purpura and pregnancy (gestational thrombocytopenia). Nonimmunologic destruction of platelets characterizes e.g. disseminated intravascular coagulation, sepsis, certain systemic infections (e.g., hepatitis, Epstein-Barr virus, cytomegalovirus), thrombocytopenia in acute respiratory distress syndrome and thrombotic thrombocytopenic purpura-hemolytic-uremic syndrome. Manifestations are petechiae, purpura, and mucosal bleeding.

Idiopathic (immunologic) thrombocytopenic purpura is a bleeding disorder caused by thrombocytopenia not associated with a systemic disease. Typically, it is chronic in adults but is usually acute and self-limited in children. Idiopathic thrombocytopenic purpura (ITP) usually results from development of an autoantibody directed against a structural platelet antigen. In childhood ITP the autoantibody may be triggered by binding of viral antigen to megakaryocytes. The symptoms and signs are petechiae, purpura, and mucosal bleeding. Gross GI bleeding and hematuria are uncommon. The spleen is of normal size unless it is enlarged by a coexistent childhood viral infection.

Treatment of ITP includes corticosteroids, splenectomy, and immunosuppressants. For life-threatening bleeding, platelet transfusions, IV corticosteroids, and IV immune globulin are required. For patients in which platelet count is <10,000 to 20,000/μL and active bleeding is present, thrombopoietin-mimetic drugs, such as romiplostim and eltrombopag, may be used. However, these drugs are used for maintenance therapy rather than induction of remission and need to be administered continuously to maintain the platelet count >50,000/μL. In children or adults with ITP and life-threatening bleeding, rapid phagocytic blockade is attempted by giving IV immune globulin 1 g/kg once/day for 1 to 2 days. This treatment usually causes the platelet count to rise within 2 to 4 days, but the count remains high only for 2 to 4 weeks. Patients with ITP and life-threatening bleeding are also given platelet transfusions. Platelet transfusions are not used prophylactically.

Posttransfusion purpura causes immunologic platelet destruction with manifestation resembling ITP, and with a history of a blood transfusion within the preceding 7 to 10 days. The patient, usually a woman, lacks a platelet antigen (PLA-1) present in most people. Transfusion with PLA-1-positive platelets stimulates formation of anti-PLA-1 antibodies, which can react with the patient's PLA-1-negative platelets. Severe thrombocytopenia results, taking 2 to 6 weeks to subside.

Connective tissue (e.g., systemic lupus erythematosus, SLE) or lymphoproliferative disorders can produce immunologic thrombocytopenia. Corticosteroids and splenectomy may be effective in treatment.

Drug-induced thrombocytopenia occurs typically by causing an immune reaction in which drug bound to the platelet creates a new and "foreign" antigen. The manifestation resembles ITP in patients with a history of drug ingestion. When the drug is stopped, the platelet count typically begins to increase within 1 to 2 days and recovers to normal within 7 days. Commonly used drugs that occasionally induce thrombocytopenia include Quinine, Trimethoprim/sulfamethoxazole, Glycoprotein IIb/IIIa inhibitors (abciximab, tirofiban), Hydrochlorothiazide, Carbamazepine, Acetaminophen, Chlorpropamide, Ranitidine, Rifampin and Vancomycin.

Autoimmune thrombocytopenic purpura (AITP) is an immune-mediated disorder in which platelets are opsonized by autoantibodies and prematurely destroyed by phagocytic cells in the reticuloendothelial system. The thrombocytopenia seen in AITP is primarily the result of increased platelet clearance by the spleen and liver. While humoral abnormalities in AITP are well defined, it is increasingly apparent that T cells play a major role in the onset of AITP. Acute and chronic forms of the disease differ in that acute AITP is often preceded by an infectious illness and generally resolves spontaneously within a few weeks of initial presentation. The chronic form of the disorder, defined as persistence of thrombocytopenia for greater than 6 months, generally occurs in adults and is classed as an organ-specific autoimmune disease that is primarily mediated by IgG autoantibodies.

Up to 5% of patients receiving unfractionated heparin develop thrombocytopenia, which may occur even with very-low-dose heparin (e.g., used in flushes to keep IV or arterial lines open). The mechanism is usually immunologic. Bleeding can occur, but more commonly platelets clump excessively, causing vessel obstruction, leading to paradoxical arterial and venous thromboses, which may be life threatening (e.g., thromboembolic occlusion of limb arteries, strokes, acute MI).

HIV infection may cause immunologic thrombocytopenia with manifestation resembling ITP. The platelet count may increase with glucocorticoids, which are often withheld unless the platelet count falls to <20,000/μL, because these drugs may further depress immune function. The platelet count also usually increases after treatment with antiviral drugs. Other infections such as systemic viral infections (e.g., Epstein-Barr virus, cytomegalovirus), rickettsial infections (e.g., Rocky Mountain spotted fever), and bacterial sepsis are typically associated with thrombocytopenia.

Mild thrombocytopenia, typically asymptomatic, occurs late in gestation in about 5% of normal pregnancies (gestational thrombocytopenia); it is usually mild (platelet counts <70,000/μL are rare), requires no treatment, and resolves after delivery. However, severe thrombocytopenia may develop in pregnant women with preeclampsia and the HELLP syndrome (hemolysis, elevated liver function tests, and low platelets); such women typically require immediate delivery, platelet transfusion is considered if platelet count is <20,000/μL (or <50,000/μL if caesarean section is to be done).

Sepsis often produces nonimmunologic thrombocytopenia that parallels the severity of the infection. The thrombocytopenia has multiple causes: disseminated intravascular coagulation, formation of immune complexes that can associate with platelets, activation of complement, and deposition of platelets on damaged endothelial surfaces.

Patients with acute respiratory distress syndrome may develop nonimmunologic thrombocytopenia, possibly secondary to deposition of platelets in the pulmonary capillary bed. Thrombocytopenia is also a frequent complication of chronic liver disease and is considered an indicator of advanced disease. The low platelet count is due partly to the effects of portal hypertension and hypersplenism, decreased thrombopoietin production, and virus-induced bone marrow suppression.

Thrombocytopenia is a frequent complication of chronic liver disease in hepatitis C virus (HCV) infected patients and is considered an indicator of advanced disease. The low platelet count in thrombocytopenia associated with HCV-related cirrhosis is considered to be partly due to the effects of portal hypertension and hypersplenism, decreased thrombopoietin production, and virus-induced bone marrow suppression.

In addition, thrombocytopenia may be caused by dilution, e.g. in massive blood replacement or exchange transfusion (due to loss of platelet viability in stored blood).

As used herein, "thrombocytopenia" is a disorder in which the platelet level in the affected individual fall below a normal range of platelet numbers for that individual, e.g. due to disturbance in production, distribution and/or destruction. Typically, a normal platelet count is between 150,000 to 450,000/µL. Platelet counts of 75,000 to 150,000/µL are defined as grade 1 thrombocytopenia, 50,000 to 75,000/µL as grade 2, 25,000 to 50,000/µL as grade 3, and below 25,000/µL as grade 4 thrombocytopenia.

The risk of bleeding is inversely proportional to the platelet count. When the platelet count is lower than 50,000/µL, minor bleeding occurs easily and the risk of major bleeding increases, and counts between 20,000 and 50,000/µL predispose to bleeding with trauma, even minor trauma. With counts lower than 20,000/µL, spontaneous bleeding may occur; with counts lower than 5000/µL, severe spontaneous bleeding is more likely, and the severe thrombocytopenia is often referred to as life threatening thrombocytopenia.

In other embodiments, thrombocytopenia also refers to a decrease in platelet number in an individual when compared to the platelet number measured at a certain reference point in that individual. The decrease in platelet number in the individual can be a decrease in more than 20%, 30%, 40%, 60%, 80%, 90%, 95% or even more, compared to value at the reference point. A decrease in platelet number when compared to the platelet number measured at a certain reference point, can in certain individuals be accompanied with changes in bleeding, while in other individuals a comparable decrease will not be accompanied with changes in bleeding. The reference point mentioned can be for instance the start of a therapy such as a radiation or chemotherapy.

In certain embodiments, the peptides of the invention are used for treating thrombocytopenia. In other embodiments, the peptides of the invention are used for preventing thrombocytopenia. In other embodiments, the peptides of the invention are used for delaying the onset of thrombocytopenia. In other embodiments, the peptides of the invention are used for reducing the duration of thrombocytopenia. In other embodiments, the peptides of the invention are used for treating, preventing, reducing the duration of, or delaying symptoms of thrombocytopenia. In other embodiments, the peptides of the invention are used for decreasing thrombocytopenia (e.g. reducing the duration or intensity or delaying the onset of the disease or a symptom thereof).

In some embodiments, the thrombocytopenia is associated with increased platelet destruction. In some particular embodiments, the destruction is immunologic. In some particular embodiments, the destruction is non-immunologic. In other particular embodiments, the destruction is drug induced. In other embodiments, the thrombocytopenia is associated with increased platelet sequestration. In other embodiments, the thrombocytopenia is associated with platelet dilution. In other embodiments, the thrombocytopenia is associated with impaired platelet production.

In other embodiments the thrombocytopenia is associated with at least one of increased platelet destruction, increased platelet sequestration, platelet dilution and impaired platelet production. In other embodiments the thrombocytopenia is associated with only one of the above-mentioned conditions (e.g. increased platelet destruction, increased platelet sequestration, platelet dilution or impaired platelet production). Without wishing to be bound by any theory or mechanism of action, in some embodiments, methods of the invention may promote platelet release or reduce or counteract platelet destruction.

In certain embodiments, the subject is not otherwise treated (or in other embodiments amenable for treatment) with a hematopoietic agent or an agent used for treating bone marrow impairment. In other embodiments, the thrombocytopenia is not associated with neutropenia. In other embodiments, the thrombocytopenia is not associated with anemia. In other embodiments, the thrombocytopenia is not associated with megakaryocytopenia. In other embodiments, the thrombocytopenia is not associated with bone marrow deficiency or suppression. In additional embodiments, the subject is not afflicted with other platelet disorders such as disorders associated with impaired or abnormal platelet function or with clotting or coagulation deficiencies or abnormalities (e.g. a blood clotting factor disorder).

In other embodiments, the thrombocytopenia is severe thrombocytopenia. In a particular embodiment, the thrombocytopenia is grade 4 thrombocytopenia. In other embodiments, the thrombocytopenia is acute thrombocytopenia. In other embodiments, the thrombocytopenia is chronic thrombocytopenia. In other embodiments, the thrombocytopenia is characterized by blood platelet counts of less than 50,000/µL. In other embodiments, the thrombocytopenia is characterized by blood platelet counts of between 20,000 and 50,000/µL. In other embodiments, the thrombocytopenia is characterized by blood platelet counts of less than 20,000/µL. In other embodiments, the thrombocytopenia is characterized by blood platelet counts of less than 10,000/µL. In other embodiments, the thrombocytopenia is characterized by blood platelet counts of less than 5000/µL. In other embodiments, the thrombocytopenia is characterized by active bleeding. In a particular embodiment the platelet count is less than 10,000 to 20,000/µL and active bleeding is present. In other embodiments, the thrombocytopenia is characterized by life-threatening bleeding. In other embodiments, the thrombocytopenia is characterized by bleeding with tissue damage. In other embodiments, the thrombocytopenia is symptomatic. For example, the symptoms may include one or more of: hemorrhaging, petechiae, purpura, mucosal bleeding, Gross GI bleeding, hematuria, splenomegaly or in other embodiments thrombosis. In other embodiments, the thrombocytopenia is asymptomatic.

In another embodiment, there is provided a method for elevating the levels of platelets of a subject comprising administering to the subject an effective amount of a peptide of the invention. In certain embodiments, the peptides may be used to elevate platelets in conditions wherein such cells are depleted, e.g. due to bone marrow transplantation or chemotherapy, or irradiation in cancer patients. Thereby, the risk of death and complication due to platelets reduction in these patients is reduced. In other embodiments, the peptides may be used to elevate the levels of platelets in patients not suffering from irradiation- or chemotherapy-induced thrombocytopenia. For example, without limitation, the methods of the invention are used in some embodiments for the treatment of idiopathic thrombocytopenic purpura patients. In other embodiments, the peptides may be used to elevate the levels of platelets in patients with idiopathic thrombocytopenic purpura. In other embodiments, the peptides may be used to elevate the levels of platelets in patients with congenital amegakaryocytic thrombocytopenia. In other embodiments, the peptides may be used to for the treatment of congenital amegakaryocytic thrombocytopenia. In other embodiments, the peptides may be used to elevate the levels of platelets in patients with thrombocytopenia with absent radii. In other embodiments, the peptides may be used for the treatment of thrombocytopenia with absent radii. In other embodiments, the peptides may be used to elevate the levels of platelets in autoimmune thrombocytopenia. In other embodiments, the peptides may be used for the treatment of autoimmune thrombocytopenia. In other embodiments, the peptides may be used to elevate the levels of platelets in patients with thrombocytopenia associated with HCV-related cirrhosis. In other embodiments, the peptides may be used for the treatment of thrombocytopenia associated with HCV-related cirrhosis. In other embodiments, the peptides may be used for the treatment of essential thrombocythemia.

In other embodiments, the methods may be used for elevating the levels of platelets as measured in peripheral blood of said subject.

In various embodiments, the treatment may induce a remission in thrombocytopenia. In some embodiments, the blood platelet levels may be restored to normal levels or to those characterizing less severe grades of thrombocytopenia (e.g. from grade 4 to grade 3, 2 or 1, from grade 3 to grade 2 or 1 etc). In a particular embodiment the treatment is associated with inducing or maintaining in the subject blood platelet levels of more than 50,000/μL. In other embodiments, the treatment is associated with inducing or maintaining in the subject blood platelet levels of between 20,000 and 50,000/μL. In other embodiments, the treatment is associated with inducing or maintaining in the subject blood platelet levels of more than 20,000/μL. In other embodiments, the treatment results in increasing platelet levels in a subject by 20%, 30%, 40%, 60%, 80%, 90%, 95% or even more, compared to value at a reference point (e.g. the onset of treatment or the level in a control subject not treated by a peptide of the invention).

In other embodiments, the treatment induces a significant elevation of platelets in peripheral blood of said subject in acute and/or chronic manners. A significant elevation as used herein refers in some embodiments to a statistically significant elevation, to a clinically significant elevation (i.e. resulting in an improvement in the condition of the subject, in manifestation of the symptoms etc) and/or to a significant elevation as recognized by the skilled artisan. For example, the platelet levels (e.g. blood levels) may be enhanced by about 10%, 20%, 30%, 40%, 60%, 80%, 90%, 95% or more after a predetermined duration. An acute elevation means that the significant increase occurs after less than 24 hours and within hours or minutes of administration, e.g. within 10, 20, 30, 40, 50 or 60 minutes or within 1-24 hours e.g. 1, 2, 3, 4 or 8 hours. Chronic elevation means that the increase occurs or may be observed within days or weeks of administration (e.g. within 3, 4, 5, 6, 7, 8, 9 or 10 days)

In another embodiment the invention may be used for the treatment of a subject afflicted with thrombocytopenia wherein administration of said peptide is initiated within 24 hours of a surgical procedure (e.g. 1, 2, 3, 4 or 8 hours, or 10, 20, 30, 40 or 50 minutes prior to surgery, or in other embodiments during surgery or within 1, 2, 3, 4 or 8 hours, or 10, 20, 30, 40 or 50 minutes after surgery).

In another embodiment, the method decreases (e.g. reduces the duration or intensity or delaying the onset of) a clinical symptom of thrombocytopenia. In one embodiment, the symptom is bleeding.

The World Health Organization made a standardized grading scale to measure the severity of bleeding. Grade 0—no bleeding; Grade 1—petechial bleeding; Grade 2—mild blood loss (clinically significant); Grade 3—gross blood loss, requires transfusion (severe); Grade 4—debilitating blood loss, retinal or cerebral associated with fatality. In various embodiments, the methods may be used for decreasing, inhibiting, treating or preventing Grade 2, 3 or 4 bleeding (clinically significant bleeding, severe bleeding or debilitating bleeding), wherein each possibility represents a separate embodiment of the invention. In another embodiment, the peptide is used for elevating blood platelet levels during a bleeding episode. In another embodiment the method is used for inhibiting excessive bleeding occurring at a site.

The peptides of the invention have unexpectedly been found to potentiate the activity of Thrombopoietin in vivo, thus allowing improved thrombopoietic activity with reduced side effects. Thus, in another embodiment, there is provided a method for enhancing Thrombopoietin-induced elevation of platelet levels in a subject in need thereof, comprising administering to said subject Thrombopoietin in combination (concomitantly or sequentially) with a peptide having an amino acid sequence as set forth in SEQ ID NO:1 or an analog or derivative thereof. In another embodiment, there is provided a method for reducing the duration of thrombocytopenia in a subject in need thereof comprising administering to the subject an effective amount of TPO in concurrent or sequential combination with a peptide having an amino acid sequence as set forth in SEQ ID NO:1 or an analog or derivative thereof. In another embodiment, the peptides of the invention may be used in combination with TPO for the treatment of thrombocytopenia as detailed herein.

The administration route and dose may be adjusted according to the patient's condition, and various regimens would be apparent to a skilled artisan (e.g. the treating physician) in view of the current disclosure and examples. In some embodiments, the peptides may be administered in an acute manner, e.g. as single dose administration or short term administration, for example when acute or transient platelet elevation is required (e.g. prior to surgical procedures). For instance, as demonstrated in Example 3, a single subcutaneous injection of 4F-benzoyl-TN14003 (0.9 mg/kg) induced elevation of blood platelet levels in human thrombocytopenic patients scheduled for stem cell harvesting, measured minutes or hours after administration. In other embodiments, the peptides may be administered in a chronic manner, e.g. as repeated administration or long-term administration. For instance, Examples 1 and 2 show that once daily subcutaneous injections of 4F-benzoyl-TN14003 for several days induced a prolonged effect in elevating platelet levels. In some embodiments, the peptides are administered systemically. In other embodiments, the peptides are administered locally. In a particular embodiment, the peptides are administered parenterally. For example, the peptides may be administered subcutaneously, intravenously or intradermally.

In other embodiments, the invention relates to the use of a peptide of an amino acid sequence as set forth in SEQ ID NO: 1 or an analog thereof for the preparation of a medicament for elevating the levels of platelets in a subject in need thereof.

In other embodiments, the invention is directed to the use of a peptide of an amino acid sequence as set forth in SEQ ID NO:1 or an analog thereof for the preparation of a medicament for treating or preventing thrombocytopenia in a subject in need thereof.

In further embodiments, the invention discloses the use of a peptide of an amino acid sequence as set forth in SEQ ID NO:1 or an analog thereof for the preparation of a medicament for enhancing thrombopoietin-induced elevation of platelet levels in a subject in need thereof wherein said subject is concurrently treated with thrombopoietin or a thrombopoietin agonist.

According to other embodiments the invention provides the use of a peptide of an amino acid sequence as set forth in SEQ ID NO:1 or an analog thereof for the preparation of a medicament for inhibiting bleeding in a subject in need thereof.

In other embodiments the invention relates to a pharmaceutical composition comprising a peptide of an amino acid sequence as set forth in SEQ ID NO: 1 or an analog thereof for elevating the levels of platelets, for treating or preventing thrombocytopenia, for enhancing thrombopoietin-induced elevation of platelet levels or for inhibiting bleeding in a subject in need thereof, as detailed herein.

EXAMPLES

Materials and Methods

Reagents

Thrombopoietin was purchased from PROSPEC cat #CYT-346. 4F-benzoyl-TN14003 (SEQ ID NO: 1) was synthesized by Novotide Ltd.

Mice and Experimental Protocol

Female C57BL/6 mice (7-8 weeks old) were purchased from Harlan Israel and maintained under specific pathogen-free conditions at the Hebrew University Animal Facility (Jerusalem, Israel).

4F-benzoyl-TN14003 and Thrombopoietin were reconstituted in PBS at various concentrations. Mice were injected subcutaneously in a total volume of 200 μl. 4F-benzoyl-TN14003 (100 ug/mouse, 5 mg/Kg) was injected for 5 days, once a day and at day 5 blood was collected and tested for platelets counts and hematopoietic colonies were tested in the bone marrow. Thrombopoietin was injected 3 times once a day, at (0.5 ug/mouse), and blood was collected and tested for platelets counts and hematopoietic colonies were tested in the bone marrow at day 5. In another group 4F-benzoyl-TN14003 (100 ug/mouse) was injected for 5 days, once a day and at days 3, 4 and 5 mice were further injected with Thrombopoietin (namely 3 times once a day, at 0.5 ug/mouse). Blood was collected and tested for platelets counts and hematopoietic colonies were tested in the bone marrow at day 5. Control mice were injected with PBS at the appropriate volume and blood was collected and tested for platelets counts and hematopoietic colonies in the bone marrow at day 5.

In the chemotherapy experiments 5-fluorouracil (5FU) at 150 mg/kg was dissolved in saline and injected intraperitoneally (on day 0). The mice were treated with 4F-benzoyl-TN14003 (5 mg/Kg) for 5 days or with TPO (0.5 μg/mouse) for 3 days before treatment with 5FU. 4F-benzoyl-TN14003 treated mice were further treated daily with 4F-benzoyl-TN14003 (5 mg/Kg) one day after 5FU administration and the treatment was continued until the end of the experiment. Blood samples were collected 1 hr following 4F-benzoyl-TN14003 administration or control (PBS) injection]; total blood counts were tested by American Medical Laboratories, Israel. In some experiments, G-CSF was s.c. injected daily, one day after 5FU administration until the end of the experiment, at final concentration of 5 μg/mouse in total volume of 0.2 ml.

Hematopoietic Progenitor Cells (HPCs) Assay

In order to evaluate the number of progenitor cells in the Bone marrow, a colony-forming cell assay was used for the production of hematopoietic colonies following treatments. Colonies were assayed by plating the cells in Iscove's-modified Dulbecco's Medium (IMDM) containing 1% methylcellulose, 15% FBS, 1% bovine serum albumin (BSA), 3 U/mL rh EPO, $10^4$ M 2-mercaptoethanol, 2 mM L-glutamine, 50 ng/mL rmSCF, 10 ng/mL rmIL-3, 10 μg/mL rh Insulin, 10 ng/mL rh IL-6, and 200 μg/mL Human Transferrin (Methocult GF M3434; StemCell Technologies Inc.). The cultures were incubated at 37° C. in a humidified atmosphere containing 5% $CO_2$. Seven days later, typical colonies were visually scored by morphologic criteria using a light microscope.

Statistical Analysis

Results are expressed as average±SD. Statistical differences were determined by an analysis of two-tailed Student's t-test. Values of $p<0.05$ were considered to be statistically significant.

Clinical Protocol

A Phase VII a, non-Randomized, Open Label, Single Dose, Dose-Escalation, Safety Study of 4F-benzoyl-TN14003 was conducted in patients with Multiple Myeloma (MM) receiving G-CSF for inducing mobilization of progenitor stem cells from the Bone Marrow to the peripheral blood.

All eligible patients received, in an ambulatory setting, as part of their planned therapy: Cyclophosphamide—(the generic name for Cytoxan, Neosar), 4 gr/m² according to the accepted MM practice. G-CSF (neupogen) was initiated 5 days later and continued until the end of stem cell collection, administered SC at 5 μg/kg per day every day after 18:00. Monitoring the WBC and platelets was done after 7 and 10 days, and until stem cell collection. Stem cell collection was performed according to the protocol of WBC over 1,000 cells.

4F-benzoyl-TN14003 was injected after 10 days, as a single dose of 30, 100, 300 or 900 μg/Kg. The follow-up post injection included counting WBC and platelets levels at points of 30 min, 1 hr, 2 hr, 4 hr, 8 hr, 24 hr.

The label "4FB-TN140" as it appears throughout the figures, is used to indicate 4F-benzoyl-TN14003 (SEQ ID NO: 1). "PLAT" represents blood platelet levels.

Example 1

Production of Colonies and Platelets

Figure 1B:
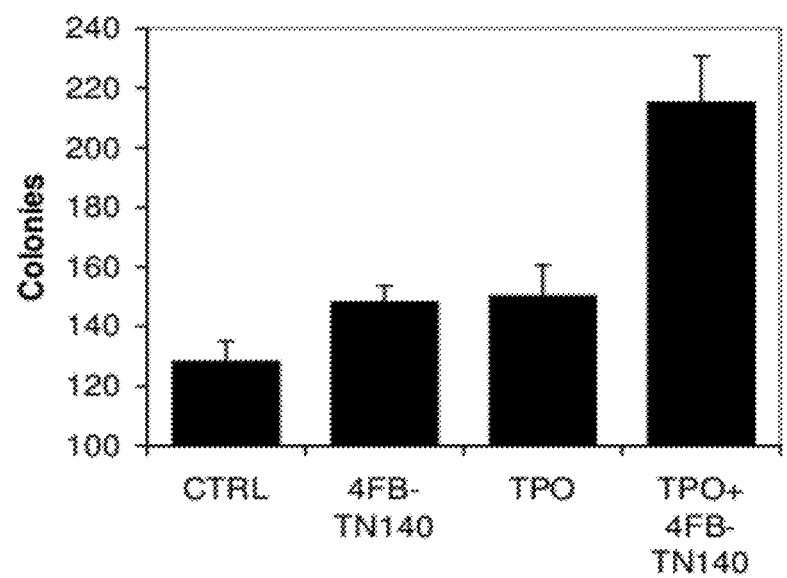
FIG. 1B demonstrates that 4F-benzoyl-TN14003 enhances the number of colony forming cells by itself and in combination with Thrombopoietin.

As can be seen in FIG. 1 and Tables 2 and 3,4F-benzoyl-TN14003 and Thrombopoietin induce platelets production in the blood (FIG. 1A, Table 2) and colony forming cells (hematopoietic precursor cells, "HPC") in the bone marrow (FIG. 1B, Table 3). It was also found that these agents cooperate together to further stimulate platelet numbers in the blood and production of progenitors in the bone marrow.

Thus, 4F-benzoyl-TN14003 potentiates the activity of TPO in enhancing platelets levels in vivo.

In FIG. 1, "CTRL" indicates phosphate-buffered saline (PBS)-treated mice, "PLAT" indicates blood platelet levels, "Colonies" indicates the number of colony forming cells (hematopoietic precursor cells) in the bone marrow and "TPO" indicates thrombopoietin-treated mice.

TABLE 2

Effect of 4F-benzoyl-TN14003 and TPO on platelet counts

| P value | % increase | SD | Platelets (×10³) | Treatment |
|---|---|---|---|---|
|  |  | 123 | 1172 | Control |
| 0.00509 | 32 | 263 | 1551 | 4F-benzoyl-TN14003 |
| 0.000589 | 32 | 133 | 1556 | TPO |
| 0.008486 | 63 | 43 | 1912 | TPO + 4F-benzoyl-TN14003 |

TABLE 3

Effect of 4F-benzoyl-TN14003 and TPO on HPC counts

| P value | SD | Colonies | Treatment |
|---|---|---|---|
|  | 6.9 | 128.2 | Control |
| 0.1 | 5.5 | 148.2 | 4F-benzoyl-TN14003 |
| 0.2 | 15.5 | 150.2 | TPO |
| 0.01 | 19 | 215.2 | TPO + 4F-benzoyl-TN14003 |

Figure 2:
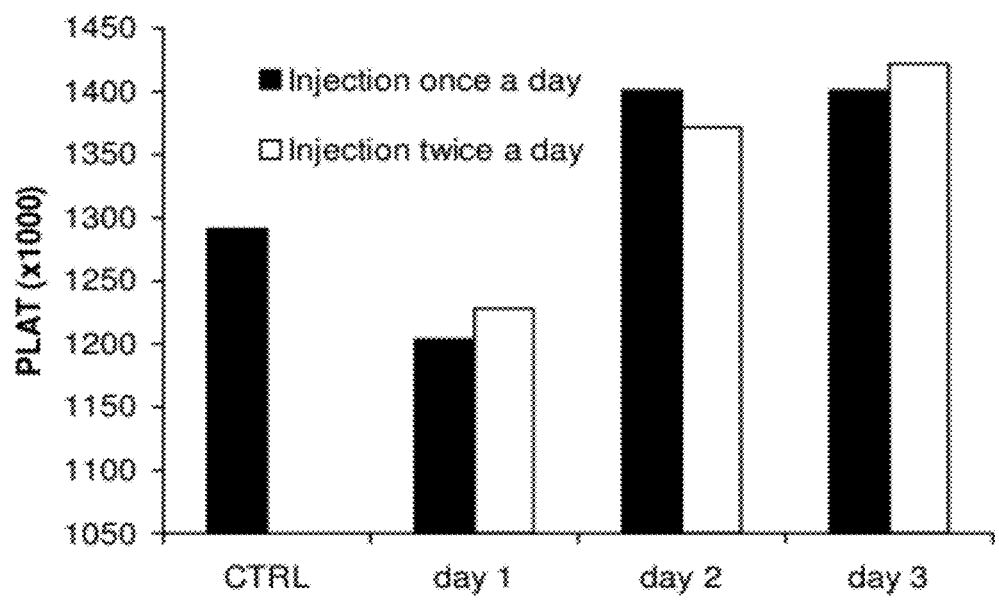
FIG. 2 demonstrates that one injection of 4F-benzoyl-TN14003 (5 mg/Kg) is sufficient to enhance the levels of platelets in blood.

In the experiments described in FIG. 2, mice were injected subcutaneously with 4F-benzoyl-TN14003 at a dose of 5 mg/kg, administered either as a once daily injection or divided into two doses administered b.i.d. Blood platelet levels were measured 1, 2 or 3 days later. As can be determined from FIG. 2, a single injection of the peptide was sufficient to induce a significant elevation in blood platelet levels.

Figure 3:
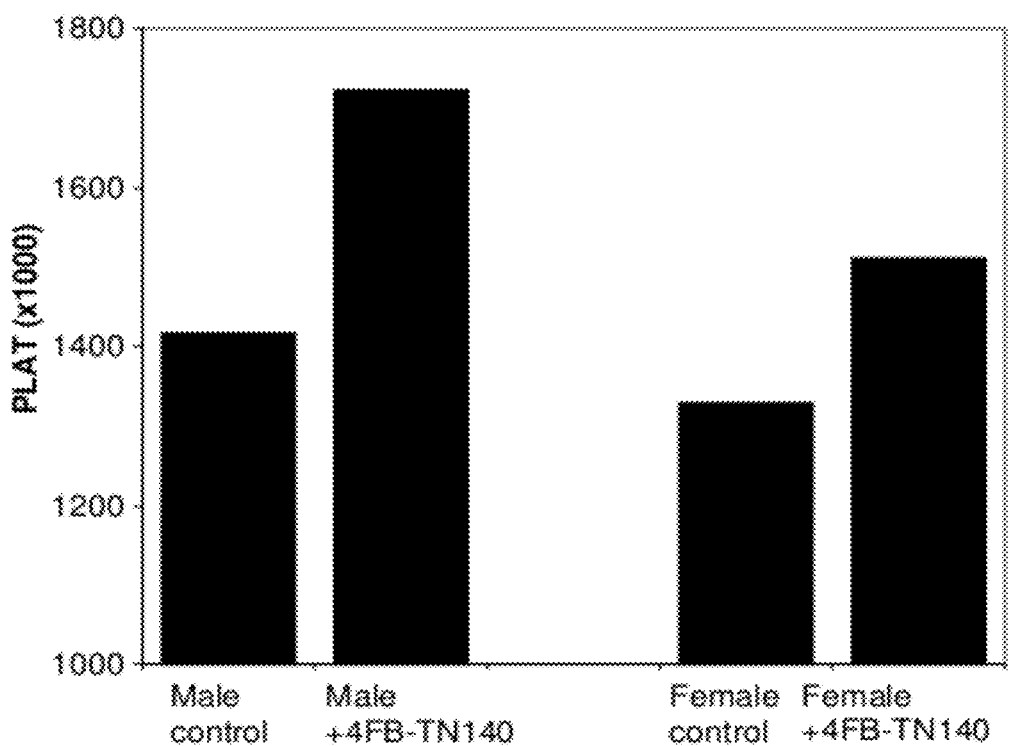
FIG. 3 demonstrates that one injection of 4F-benzoyl-TN14003 (5 mg/Kg) is sufficient to enhance the levels of platelets in blood of both male and female mice.

As can be seen in FIG. 3, this effect was observed in both male and female mice, as the peptide enhanced blood platelet levels measured 3 days post administration in male and female animals. In FIG. 3, "Male control" and "Female control" indicate PBS-treated male and female mice, respectively; "Male+4FB-T140" and "Female+4FB-T140" indicate male or female mice treated with 4F-benzoyl-TN14003 (5 mg/kg)

Example 2

Prevention of Chemotherapy-Induced Thrombocytopenia

Figure 4:
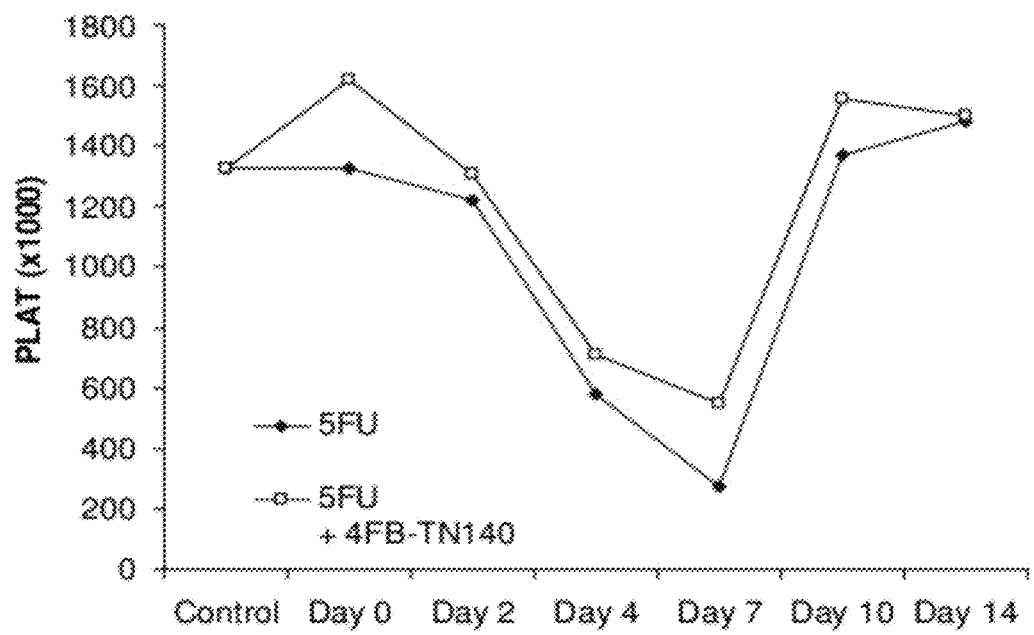
FIG. 4 demonstrates that injection of 4F-benzoyl-TN14003 (5 mg/Kg) for 5 days pre treatment of mice with 5FU, wherein the treatment with 4F-benzoyl-TN14003 is continued following 5FU treatment, enhances the levels of platelets in blood before and after treatment with 5FU.

The platelet modulating effects were then examined in a chemotherapy-induced thrombocytopenia model in mice. In these experiments, 5-fluorouracil ("5FU") at 150 mg/kg dissolved in saline was injected intraperitoneally to all mice (on day 0). Some of the mice were further treated with 4F-benzoyl-TN14003 (5 mg/Kg, once daily S.C. injections) for 5 days before treatment with 5FU, and Mice were further treated daily with 4F-benzoyl-TN14003 (5 mg/Kg) one day after 5FU and the treatment was continued until the end of the experiment. Blood samples were collected 1 hr following administration of 4F-benzoyl-TN14003 or control (PBS) injection. As can be seen in FIG. 4, administration of 4F-benzoyl-TN14003 enhanced the levels of platelets in blood before and after treatment with 5FU. In FIG. 4, diamonds represent control (PBS treated) mice; open squares represent 4F-benzoyl-TN14003 treated mice.

Figure 5:
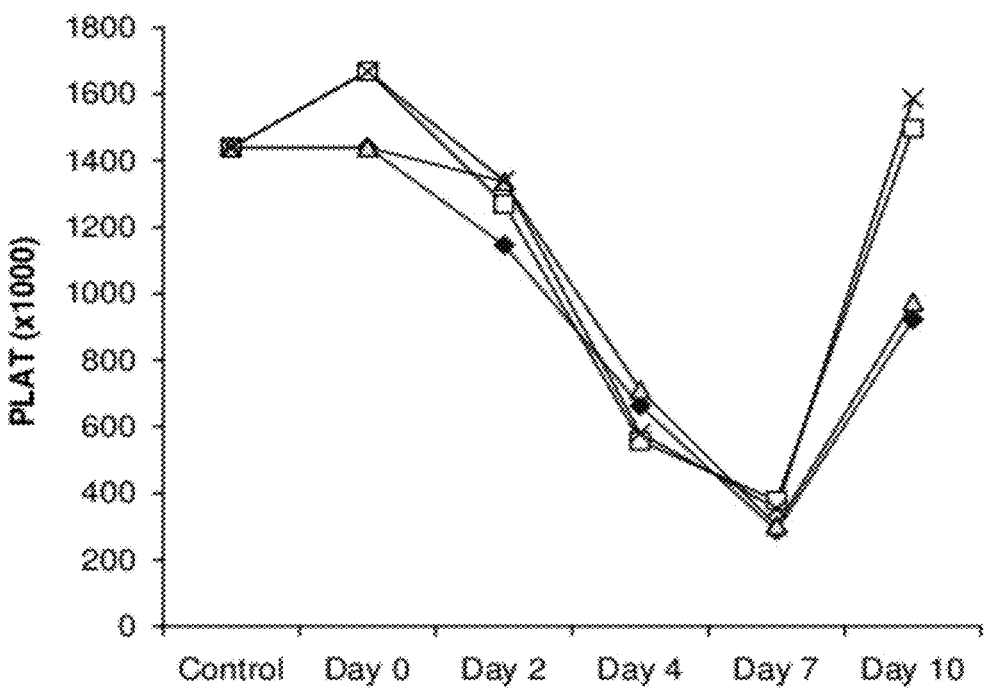
FIG. 5 demonstrates that injection of 4F-benzoyl-TN14003 (5 mg/Kg) for 5 days pre treatment of mice with 5FU wherein the treatment with 4F-benzoyl-TN14003 (5 mg/Kg) is continued following 5FU treatment enhances the levels of platelets in blood before and after treatment with 5FU, whereas treatment with G-CSF, one day after injection of 5FU, alone or in combination with 4F-benzoyl-TN14003 had no effect on platelet levels.

Next, the effect of the peptide on mice treated with 5FU with or without G-CSF was examined. G-CSF administration (as daily S.C. injections, 5 μg/mouse) was initiated one day after 5FU treatment and continued until the end of the experiment. 5FU and 4F-benzoyl-TN14003 administration and blood sample collection were as specified above for FIG. 4. As shown in FIG. 5, 4F-benzoyl-TN14003 enhanced the levels of platelets in blood before and after treatment with 5FU, when administered alone or in combination with G-CSF. Treatment with G-CSF had no effect on blood platelet levels and did not alter the 4F-benzoyl-TN14003-elevation of platelet levels. In FIG. 5, diamonds represent control (PBS treated) mice; open squares represent 4F-benzoyl-TN14003 treated mice; triangles represent G-CSF treated mice; and crosses represent mice treated with G-CSF and 4F-benzoyl-TN14003.

Figure 6:
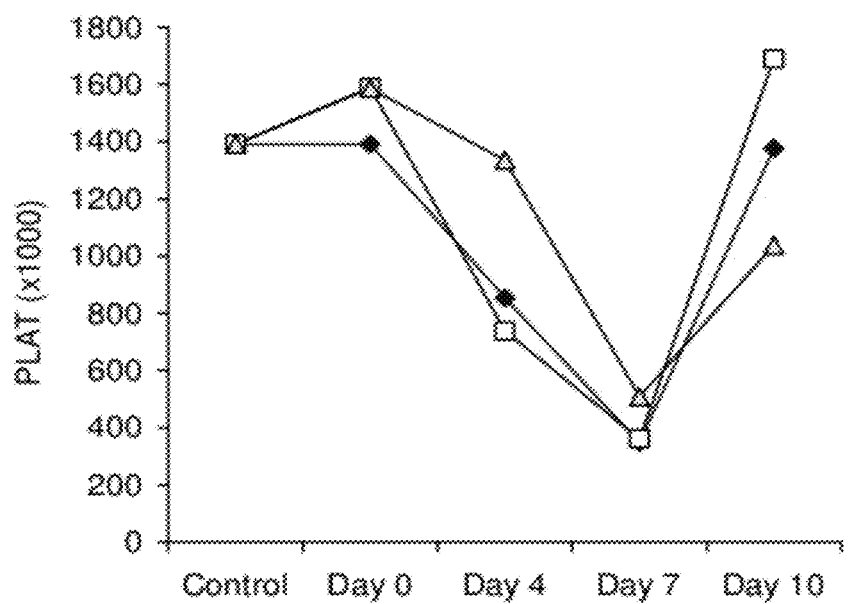
FIG. 6 demonstrates that injection of 4F-benzoyl-TN14003 (5 mg/Kg) for 5 days pre treatment of mice with 5FU wherein the treatment with 4F-benzoyl-TN14003 (5 mg/Kg) is continued following 5FU treatment enhances the levels of platelets in blood before and after treatment with 5FU, whereas administration of TPO (0.5 µg/mouse) for 3 days before 5FU treatment is inferior to treatment with 4F-benzoyl-TN14003.

The activity of the peptide in the chemotherapy-induced thrombocytopenia model was then compared to that of TPO. In the TPO group, mice were treated with a single dose of TPO (0.5 μg/mouse) for 3 days before treatment with 5FU. 5FU and 4F-benzoyl-TN14003 administration and blood sample collection were as specified above for FIG. 4. As can be seen in FIG. 6, both TPO and 4F-benzoyl-TN14003 elevated blood platelet levels before or after 5FU administration. After 10 days of administration, platelet levels were higher in 4F-benzoyl-TN14003-treated mice than in TPO-treated mice or control mice. In FIG. 6, diamonds represent control (PBS treated) mice; open squares represent 4F-benzoyl-TN14003 treated mice; and triangles represent TPO treated mice.

Example 3

Acute Elevation of Platelets in Thrombocytopenic Patients

Figure 7A:
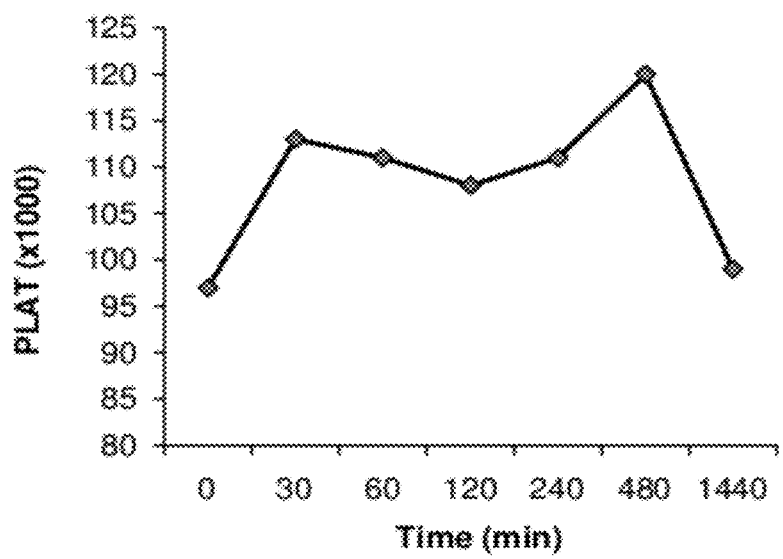
FIG. 7 demonstrates that injection of 4F-benzoyl-TN14003 (0.9 mg/Kg) once into human patients stimulates an immediate increase in the number of platelets in the blood (FIG. 7A—patient 1.
FIG. 7B—patient 2).
Figure 7B:
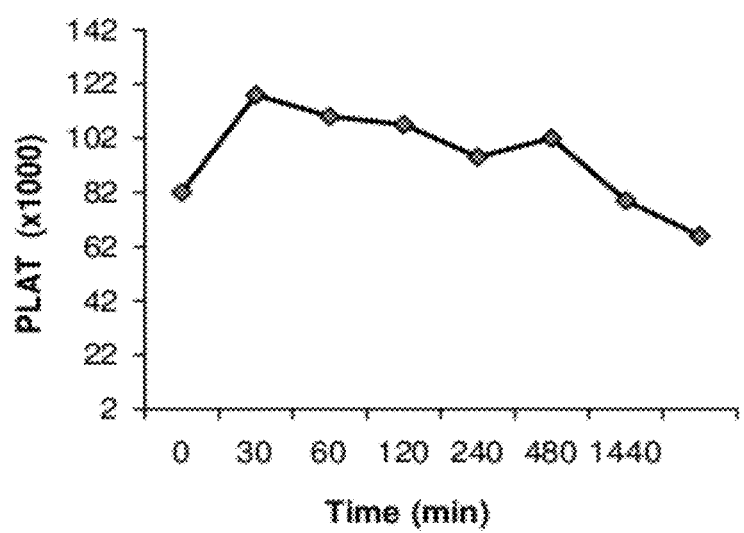

MM patients undergoing chemotherapy with Cyclophosphamide, received G-CSF according to a clinical protocol for inducing HPC mobilization for subsequent harvesting and transplantation. 10 days after Cyclophosphamide and G-CSF treatment, the patients received 4F-benzoyl-TN14003 injected at a dose of 0.9 mg/kg. As can be seen in FIG. 7, 4F-benzoyl-TN14003 stimulated an immediate increase in the number of platelets in the blood, which could be detected 30 minutes after administration and was still observed several hours later (after 1, 2, 4 or 8 hours). In FIG. 7, the "0 min" time point represents blood platelet levels at the time of injection of 4F-benzoyl-TN14003.

REFERENCES

Avniel, S. et al., *J. Invest. Dermatol.* 2006, 126(2): 468-76.

Junzhi Li, Chun Yang, Yuping Xia, Amy Bertino, John Glaspy, Michael Roberts and David J. Kuter. Thrombocytopenia caused by the development of antibodies to thrombopoietin. *Blood.* 2001 98:3241-3248

Kaushansky K, Lok S, Holly R D, et al. Promotion of megakaryocyte progenitor expansion and differentiation by the c-Mp1 ligand thrombopoietin. *Nature.* 1994; 369: 568-571

Princen, K. and Schols, D., *Cytokine Grow. Fac. Rev.* 2005, 16(6): 659-677.

Rossi, D. and Zlotnik, A., *Ann. Rev. Immun.* 2000, 18: 217-242.

Tamamura, H. and Fujii, N., *Expert Opin. Ther. Targets,* 2005, 9(6): 1267-1282.

Tamamura, H. et al., *Org. Biomol. Chem.* 2003, 1: 3663-3669.

Tamamura, H. et al., *Biochem. Biophys. Res. Commun.* 1998, 253(3): 877-882.

William J. Lane, Sergio Dias, Koichi Hattori, Beate Heissig, Margaret Choy, Sina Y. Rabbany, Jeanette Wood, Malcolm A. S. Moore and Shahin Rafii. Stromal-derived factor 1-induced megakaryocyte migration and platelet production is dependent on matrix metalloproteinases. *Blood,* 15 Dec. 2000, Vol. 96, No. 13, pp. 4152-4159

The foregoing description of the specific embodiments will so fully reveal the general nature of the invention that others can, by applying current knowledge, readily modify and/or adapt for various applications such specific embodiments without undue experimentation and without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. The means, materials, and steps for carrying out various disclosed functions may take a variety of alternative forms without departing from the invention.

The invention claimed is:

1. A method for transiently elevating the levels of platelets in peripheral blood of a thrombocytopenic human subject in need thereof, comprising administering to the human subject an effective amount of a peptide of an amino acid sequence as set forth in SEQ ID NO:1 so as to transiently elevate the levels of platelets in the thrombocytopenic human subject.

2. The method of claim 1 wherein the thrombocytopenia of the thrombocytopenic human subject is characterized by platelet counts of less than 20,000/μL.

3. The method of claim 1 wherein the thrombocytopenia of the thrombocytopenic human subject is characterized by a platelet count of less than 10,000/μL.

4. The method of claim 1, wherein the peptide is administered to said subject in combination with at least one cytokine that stimulates platelets production.

5. The method of claim 4, wherein said peptide is administered in combination with thrombopoietin or a thrombopoietin agonist.

6. The method of claim 1 wherein said peptide is administered in the form of a pharmaceutical composition further comprising at least one cytokine that stimulates platelets production.

* * * * *